United States Patent
Liebeschuetz et al.

(10) Patent No.: US 6,878,725 B2
(45) Date of Patent: Apr. 12, 2005

(54) SERINE PROTEASE INHIBITORS

(75) Inventors: John Walter Liebeschuetz, Bollington (GB); Christopher William Murray, Swavesey (GB); Stephen Clinton Young, Heaton Moor (GB); Nicholas Paul Camp, Bracknell (GB); Stuart Donald Jones, Macclesfield (GB); William Alexander Wylie, Carrickfergus (GB); John Joseph Masters, Fishers, IN (US); Michael Robert Wiley, Indianapolis, IN (US); Scott Martin Sheehan, Carmel, IN (US); David Birenbaum Engel, Bloomington, IN (US); Brian Morgan Watson, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/030,189

(22) PCT Filed: Jun. 12, 2001

(86) PCT No.: PCT/GB01/02541

§ 371 (c)(1),
(2), (4) Date: Feb. 4, 2002

(87) PCT Pub. No.: WO01/96296

PCT Pub. Date: Dec. 20, 2001

(65) Prior Publication Data

US 2003/0078438 A1 Apr. 24, 2003

(51) Int. Cl.$^7$ ............... A61K 31/445; C07D 401/12; C07D 401/14
(52) U.S. Cl. ............ 514/318; 514/169; 514/320; 514/323; 514/324; 514/326; 544/333; 546/193; 546/197; 546/199; 546/201; 546/202; 546/209; 546/210; 548/400
(58) Field of Search ............... 514/269, 318, 514/320, 322, 323, 324, 326; 544/333; 546/193, 197, 199, 201, 202, 209, 210; 548/400

(56) References Cited

U.S. PATENT DOCUMENTS

| 5,346,907 | A | 9/1994 | Kerwin et al. |
| 6,262,069 | B1 * | 7/2001 | Liebeschuetz et al. ...... 514/310 |
| 6,545,055 | B1 | 4/2003 | Zhu et al. |
| 2002/0151724 | A1 * | 10/2002 | Liebeschuetz et al. ...... 548/400 |

FOREIGN PATENT DOCUMENTS

| EP | 796866 A1 | 9/1997 |
| WO | WO 91/00725 | 1/1991 |
| WO | WO 97/49404 | 12/1997 |
| WO | WO 98/47876 | 10/1998 |
| WO | WO 99/00121 | 1/1999 |
| WO | WO 99/00126 | 1/1999 |
| WO | WO 99/00127 | 1/1999 |
| WO | WO 99/00128 | 1/1999 |
| WO | WO 99/11657 | 3/1999 |
| WO | WO 99/11658 | 3/1999 |
| WO | WO 00/39092 | 7/2000 |
| WO | WO 00/39111 | 7/2000 |
| WO | WO 00/39117 | 7/2000 |
| WO | WO 00/39118 | 7/2000 |
| WO | WO 00/71493 | 11/2000 |
| WO | WO 00/71507 | 11/2000 |
| WO | WO 00/71508 | 11/2000 |
| WO | WO 00/76971 | 12/2000 |
| WO | WO 00/76970 | 12/2002 |
| WO | WO 00/77027 | 12/2002 |

OTHER PUBLICATIONS

Claims of U.S. Appl. No. 10/030,186.*

Jones, Stuart D, et al., Bioorganic & Medicinal Chemistry Letters 11 (2001) 733–736.

* cited by examiner

*Primary Examiner*—Celia Chang
(74) *Attorney, Agent, or Firm*—Martin A. Hay

(57) ABSTRACT

Compounds of formula (I)

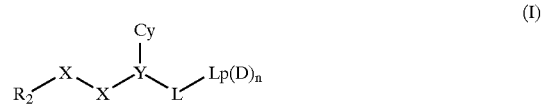

in which $R_2$, X, Y, Cy, L and $Lp(D)_n$ have the meanings given in the specification, are inhibitors of the serine protease, Factor Xa and are useful in the treatment of cardiovascular disorders.

28 Claims, No Drawings

SERINE PROTEASE INHIBITORS

This invention relates to compounds which are inhibitors of serine proteases and to pharmaceutical compositions thereof and their use in the treatment of the human or animal body.

The serine proteases are a group of proteolytic enzymes which have a common catalytic mechanism characterized by a particularly reactive Ser residue. Examples of serine proteases include trypsin, tryptase, chymotrypsin, elastase, thrombin, plasmin, kallikrein, Complement C1, acrosomal protease, lysosomal protease, cocoonase, α-lytic protease, protease A, protease B, serine carboxypeptidase II, subtilisin, urokinase, Factor VIIa, Factor IXa, and Factor Xa. The serine proteases have been investigated extensively over a period of several decades and the therapeutic value of inhibitors of serine proteases is well understood.

Serine protease inhibitors play a central role in the regulation of a wide variety of physiological process including coagulation, fibrinolysis, fertilization, development, malignancy, neuromuscular patterning and inflammation. It is well known that these compounds inhibit a variety of circulating proteases as well as proteases that are activated or released in tissue. It is also becoming clear that serine protease inhibitors inhibit critical cellular processes, such as adhesion, migration, free radical production and apoptosis. In addition, animal experiments indicate that intravenously administered serine protease inhibitors, variants or cells expressing serine protease inhibitors, provide a protective effect against tissue damage.

Serine protease inhibitors have also been predicted to have potential beneficial uses in the treatment of disease in a wide variety of clinical areas such as oncology, neurology, haematology, pulmonary medicine, immunology, inflammation and infectious disease.

In particular serine protease inhibitors may be beneficial in the treatment of thrombotic diseases, asthma, emphysema, cirrhosis, arthritis, carcinoma, melanoma, restenosis, atheroma, trauma, shock and reperfusion injury.

Thus for example an inhibitor of Factor Xa has value as a therapeutic agent as an anticoagulant, e.g. in the treatment and prevention of thrombotic disorders. The use of a Factor Xa inhibitor as an anticoagulant is desirable in view of the selectivity of its effect. Many clinically approved anticoagulants have been associated with adverse events owing to the non-specific nature of their effects on the coagulation cascade.

Also, there are well-known associations of α1 protease inhibitor deficiency with emphysema and cirrhosis and C1 esterase inhibitor deficiency with angioedema.

It has now been found that certain aromatic compounds are particularly effective as inhibitors of serine proteases, especially proteases with negatively charged P1 specificity pockets, and most especially the serine protease Factor Xa. The Factor Xa inhibitors of this invention are potentially useful for the prophylaxis or treatment of thrombotic disorders such as amongst others venous thrombosis, pulmonary embolism, arterial thrombosis, myocardial ischaemia, myocardial infarction, and cerebral thrombosis. They potentially have benefit in the treatment of acute vessel closure associated with thrombolytic therapy and restenosis, e.g. after transluminal coronary angioplasty or bypass grafting of the coronary or peripheral arteries and in the maintenance of vascular access patency in long term hemodialysis patients.

Factor Xa inhibitors of this invention may, with benefit, form part of a combination therapy with an anticoagulant with a different mode of action or with a thrombolytic agent.

It has been reported in WO99/11658 and WO99/11657 that certain benzamidine and aminoisoquinoline derivatives carrying a bulky lipophilic side chain are excellent inhibitors of serine proteases. Unfortunately, it has since been found that benzamidine compounds of WO 99/11658 in general demonstrate poor oral bioavailability.

Surprisingly, it has now been found that certain other aromatic compounds also show inhibitory activity against serine proteases, in particular Factor Xa, despite the lack of the amidino or 1-aminoisoquinoline functionality previously believed to be crucial for activity as a factor Xa inhibitor. Many of these compounds also possess other structural features that further distinguish them from the compounds of WO99/11658 and WO99/11657.

Where compounds of the invention have been tested, they have generally demonstrated superior oral bioavailability in comparison with benzamidines disclosed in WO 99/11658. Also, it has been found that the compounds of the invention perform excellently in the prothrombin time assay (PT) when compared to aminoisoquinolines of similar factor Xa activity and structure. The PT assay is a coagulation assay and it is widely accepted that direct acting Factor Xa inhibitors which perform well in the PT assay are more likely to be good antithrombotics.

In WO99/09053 certain 2-aminobenzamide compounds are disclosed as potential motilin receptor antagonists and in U.S. Pat. No. 3,268,513 similar 2-aminobenzamide compounds are suggested as potential antibacterial agents. However, the novel compounds of the present invention have not before been suggested as potential serine protease inhibitors.

Thus viewed from an one aspect the invention provides a serine protease inhibitor compound of formula (I)

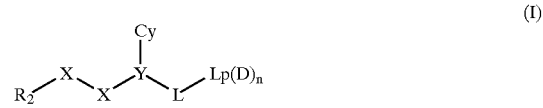

(I)

wherein:

$R_2$ is a 5 or 6 membered aromatic carbon ring optionally interrupted by a nitrogen, oxygen or sulphur ring atom, optionally being substituted in the 3 and/or 4 position (in relation to the point of attachment of X—X) by halo, nitro, thiol, haloalkoxy, hydrazido, alkylhydrazido, amino, cyano, haloalkyl, alkylthio, alkenyl, alkynyl, acylamino, tri or difluoromethoxy, carboxy, acyloxy, $MeSO_2$— or $R_1$, or the substituents at the 3 and 4 positions taken together form a fused ring which is a 5 or 6 membered carbocyclic or heterocyclic ring optionally substituted by halo, haloalkoxy, haloalkyl, cyano, nitro, amino, hydrazido, alkylthio, alkenyl, alkynyl or $R_{1j}$, and optionally substituted in the position alpha to the X—X group (i.e. 6 position for a six membered aromatic ring etc) by amino, hydroxy, halo, alkyl, carboxy, alkoxycarbonyl, cyano, amido, aminoalkyl, alkoxy or alkylthio with the proviso that $R_2$ cannot be aminoisoquinolyl;

each X independently is a C, N, O or S atom or a CO, $CR_{1a}$, $C(R_{1a})_2$ or $NR_{1a}$ group, at least one X being C, CO, $CR_{1a}$ or $C(R_{1a})_2$;

each $R_{1a}$ independently represents hydrogen, hydroxyl, alkoxy, alkyl, aminoalkyl, hydroxyalkyl, alkoxyalkyl, alkoxycarbonyl, alkylaminocarbonyl, alkoxycarbonylamino, acyloxymethoxycarbonyl or alkylamino optionally substituted by hydroxy, alkylamino, alkoxy, oxo, aryl or cycloalkyl;

$R_1$ is as defined for $R_{1a}$, provided that $R_1$ is not unsubstituted aminoalkyl;

Y (the α-atom) is a nitrogen atom or a $CR_{1b}$ group;

Cy is a saturated or unsaturated, mono or poly cyclic, homo or heterocyclic group, preferably containing 5 to 10 ring atoms and optionally substituted by groups $R_{3a}$ or $R_{3i}X_i$;

each $R_{3a}$ independently is $R_{1c}$, amino, halo, cyano, nitro, thiol, alkylthio, alkylsulphonyl, alkylsulphenyl, triazolyl, imidazolyl, tetrazolyl, hydrazido, alkylimidazolyl, thiazolyl, alkylthiazolyl, alkyloxazolyl, oxazolyl, alkylsulphonamido, alkylaminosulphonyl, aminosulphonyl, haloalkoxy, haloalkyl, a group of the formula —$C(X^3)N(R^{11})R^{12}$ (wherein $X^3$ is O or S; and $R^{11}$ and $R^{12}$ are independently selected from hydrogen, methyl or ethyl or together with the nitrogen atom to which they are attached form a pyrrolidin-1-yl, piperidin-1-yl or morpholino group), or —$OCH_2O$— which is bonded to two adjacent ring atoms in Cy;

$X_i$ is a bond, O, NH or $CH_2$;

$R_{3i}$ is phenyl, pyridyl or pyrimidyl optionally substituted by $R_{3a}$;

$R_{1b}$, $R_{1c}$ and $R_{1j}$ are as defined for $R_{1a}$, and -L-Lp(D)$_n$ is of the formula:

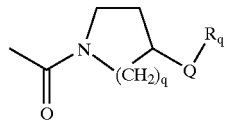

wherein:
q is 1 or 2;
Q is —O— or —NH—;

and $R_q$ is $R_c$ which is pyridyl, pyrimidin-4-yl, pyridazin-3-yl, pyridazin-4-yl or phenyl (which phenyl or pyridyl group may bear a fluoro, chloro, alkyl, $CONH_2$, $SO_2NH_2$, dialkylaminosulphonyl, methoxy, methylthio, alkylsulphonyl, alkylaminosulphonyl, alkylaminocarbonyl, amino, alkoxycarbonyl, acetylamino, cyano, ethoxy, nitro, hydroxy, alkylsulphonylamino, triazolyl or tetrazolyl substituent);

or a physiologically-tolerable salt thereof, e.g. a halide, phosphate or sulphate salt or a salt with ammonium or an organic amine such as ethylamine or meglumine.

According to another aspect, the present invention provides a serine protease inhibitor compound of formula (I)

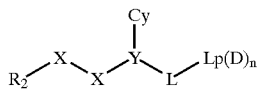

(I)

wherein:

$R_2$ is a 5 or 6 membered aromatic carbon ring optionally interrupted by a nitrogen, oxygen or sulphur ring atom, optionally being substituted in the 3 and/or 4 position (in relation to the point of attachment of X—X) by halo, nitro, thiol, haloalkoxy, hydrazido, alkylhydrazido, amino, cyano, haloalkyl, alkylthio, alkenyl, alkynyl, acylamino, tri or difluoromethoxy, carboxy, acyloxy, $MeSO_2$— or $R_1$, or the substituents at the 3 and 4 positions taken together form a fused ring which is a 5 or 6 membered carbocyclic or heterocyclic ring optionally substituted by halo, haloalkoxy, haloalkyl, cyano, nitro, amino, hydrazido, alkylthio, alkenyl, alkynyl or $R_{1j}$, and optionally substituted in the position alpha to the X—X group (i.e. 6 position for a six membered each X independently is a C, N, O or S atom or a CO, $CR_{1a}$, $C(R_{1a})_2$ or $NR_{1a}$ group, at least one X being C, CO, $CR_{1a}$ or $C(R_{1a})_2$;

each $R_{1a}$ independently represents hydrogen, hydroxyl, alkoxy, alkyl, aminoalkyl, hydroxyalkyl, alkoxyalkyl, alkoxycarbonyl, alkylaminocarbonyl, alkoxycarbonylamino, acyloxymethoxycarbonyl or alkylamino optionally substituted by hydroxy, alkylamino, alkoxy, oxo, aryl or cycloalkyl;

$R_1$ is as defined for $R_{1a}$, provided that $R_1$ is not unsubstituted aminoalkyl;

Y (the α-atom) is a nitrogen atom or a $CR_{1b}$ group;

Cy is a saturated or unsaturated, mono or poly cyclic, homo or heterocyclic group, preferably containing 5 to 10 ring atoms and optionally substituted by groups $R_{3a}$ or phenyl optionally substituted by $R_{3a}$;

each $R_{3a}$ independently is $R_{1c}$, amino, halo, cyano, nitro, thiol, alkylthio, alkylsulphonyl, alkylsulphenyl, triazolyl, imidazolyl, tetrazolyl, hydrazido, alkyl imidazolyl, thiazolyl, alkyl thiazolyl, alkyl oxazolyl, oxazolyl, alkylsulphonamido, alkylaminosulphonyl, aminosulphonyl, haloalkoxy and haloalkyl;

$R_{1b}$, $R_{1c}$ and $R_{1j}$ are as defined for $R_{1a}$, and -L-Lp(D)$_n$ is of the formula:

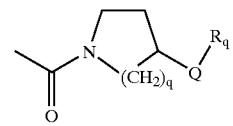

wherein:
q is 1 or 2;
Q is —O— or —NH—;

and $R_q$ is $R_c$ which is pyridyl or phenyl (which phenyl may bear a fluoro, chloro, methyl, $CONH_2$, $SO_2NH_2$, methylaminosulphonyl, dimethylaminosulphonyl, methylsulphonylamino, methoxy or methylsulphonyl substituent);

or a physiologically-tolerable salt thereof.

In the compounds of the invention, where the alpha atom is carbon it preferably has the conformation that would result from construction from a D-α-aminoacid $NH_2$—$CR_{1b}$ (Cy)—COOH where the $NH_2$ represents part of X—X. Likewise the fourth substituent $R_{1b}$ at an alpha carbon is preferably a methyl or hydroxymethyl group or hydrogen.

In the compounds of the invention, unless otherwise indicated, aryl groups preferably contain 5 to 10 ring atoms optionally including 1, 2 or 3 heteroatoms selected from O, N and S; alkyl, alkenyl or alkynyl groups or alkylene moieties preferably contain up to 6 carbons, e.g. $C_{1-6}$ or $C_{1-3}$; cyclic groups preferably have ring sizes of 3 to 8 atoms; and fused multicyclic groups preferably contain 8 to 16 ring atoms.

Examples of particular values for $R_{1a}$ are: hydrogen, ethyl or ethyl. $R_{1a}$ is preferably a hydrogen atom.

The linker group from the $R_2$ group to the alpha atom is preferably selected from —CH=CH—, —CONH—, —$CONR_{1a}$—, —NH—CO—, —NH—$CH_2$—, —$CH_2$—NH—, —$CH_2O$—, —$OCH_2$—, —COO—, —OC=O— and —$CH_2CH_2$—. Preferably, the X moiety nearest to the alpha atom is an NH or O atom, most preferably a NH group. The X moiety alpha to the aromatic ring is preferably a carbon based group such as $CH_2$ or CO, preferably CO. Thus a particularly preferred linker X—X is —CONH—. In an alternative embodiment the linker is preferably a —$OCH_2$— group.

Examples of particular values for $R_{1b}$ are: hydrogen, (1–4C) alkyl, such as methyl or hydroxy(1–4C)alkyl, such as hydroxymethyl. $R_{1b}$ is preferably a hydrogen atom. The alpha atom (Y) is preferably a CH or $C(CH_3)$ group, especially CH.

Preferably, the group L-Lp(D)$_n$ is selected from the following formulae:

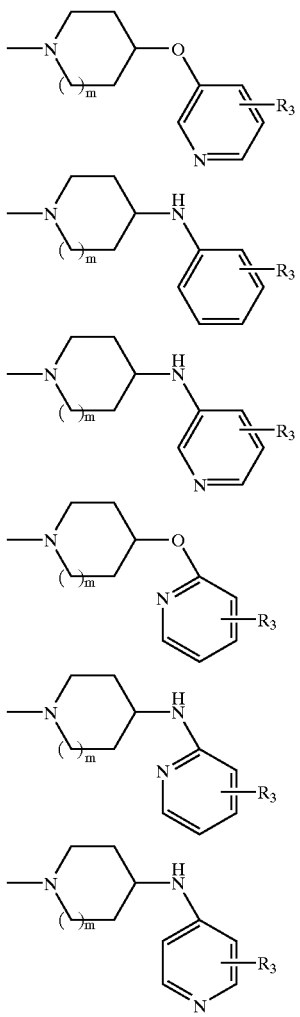

wherein:

m represents 0 or 1; and when R$_3$ is present as a substituent on an aromatic ring, it is selected from hydrogen, alkylsulphonyl, aminosulphonyl, alkylaminosulphonyl, alkylaminocarbonyl, amino, amido, alkoxycarbonyl, acetylamino, chloro, fluoro, cyano, methoxy, ethoxy, nitro, hydroxy, alkylsulphonylamino, triazolyl and tetrazolyl.

One group of formula L-Lp(D)$_n$ is that of formula

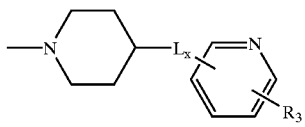

in which L$_x$ represents O or NH.

For example specific groups of formula L-Lp(D)$_n$ include the following formulae:

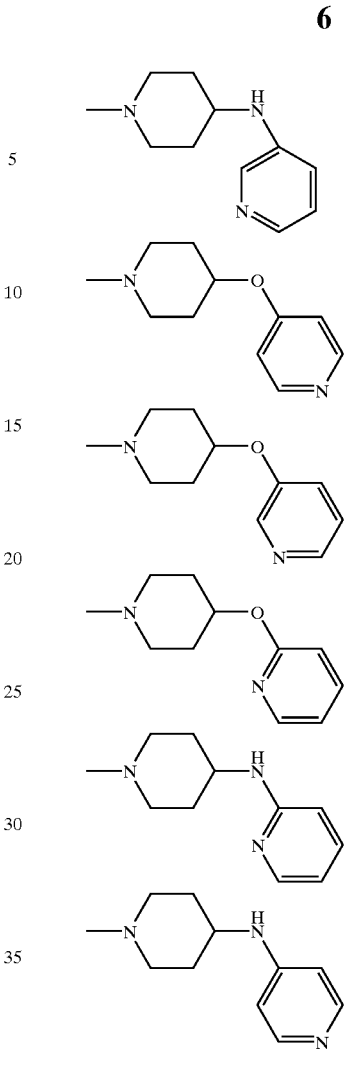

In the group represented by

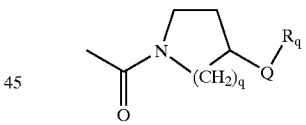

q is preferably 2.

Q may be —O—. Compounds of formula (I) in which Q is —O— have been found to exhibit good oral absorption.

In another aspect Q is —NH—. Compounds of formula (I) in which Q is —NH— have been found to exhibit good anti-coagulent activity.

R$_q$ is R$_c$, and R$_c$ may be, for example, pyridyl or phenyl (which phenyl may bear a fluoro, chloro, methyl, CONH$_2$, SO$_2$NH$_2$, methylaminosulphonyl, dimethylaminosulphonyl, methylsulphonylamino, methoxy, methylthio or methylsulphonyl substituent).

Examples of particular values for R$_c$ are phenyl, 2-fluorophenyl, 3-fluorophenyl, 4-fluorophenyl, 3-methoxyphenyl, 4-methoxyphenyl, 2-methylsulfonylphenyl, 2-methylthiophenyl, pyrid-2-yl, pyrid-3-yl or pyrid-4-yl. Further examples for R$_c$ are 6-methylpyrid-2-yl or 2-cyanopyrid-4-yl.

R$_c$ is preferably pyrid-2-yl, pyrid-3-yl, pyrid-4-yl, pyridazin-3-yl, pyridazin-4-yl, pyrimid-4-yl or phenyl.

R$_c$ may be, for example, pyridyl or phenyl, especially pyrid-3-yl or phenyl.

More preferably $R_c$ is pyrid-2-yl, pyrid-3-yl or pyrid-4-yl.

Cy is preferably an optionally $R_{3a}$ substituted: phenyl, pyridyl, thienyl, thiazolyl, naphthyl, piperidinyl, furanyl, pyrrolyl, isoxazolyl, isothiazolyl, pyrazolyl, oxazolyl, imidazolyl, 1,2,4-thiadiazolyl, 1,3,4-thiadiazolyl, pyrimidinyl, pyridazinyl, quinolyl, isoquinolyl, benzofuryl, benzothienyl or cycloalkyl group, or a phenyl group substituted by $R_{3i}X_i$ in which $X_i$ is a bond, O, NH or $CH_2$ and $R_{3i}$ is phenyl or pyridyl optionally substituted by $R_{3a}$.

The cyclic group attached to the alpha carbon may thus be an optionally $R_{3a}$ substituted phenyl, pyridyl (such as pyrid-2-yl, pyrid-3-yl or pyrid-4-yl), thienyl (such as thien-2-yl or thien-3-yl), thiazolyl (such as thiazol-2-yl, thiazol-4-yl or thiazol-5-yl), naphthyl (such as naphth-1-yl), piperidinyl (such as piperidin-4-yl) or cycloalkyl, such as a cyclohexyl group.

Examples of particular values for $R_{3a}$ are:
hydrogen;
hydroxyl;
for alkoxy: methoxy or ethoxy;
for alkyl optionally substituted by hydroxy, alkylamino, alkoxy, oxo, aryl or cycloalkyl: alkyl, such as methyl or ethyl, or alkylaminoalkyl, such as methylaminomethyl or dimethylaminomethyl;
for hydroxyalkyl optionally substituted by hydroxy, alkylamino, alkoxy, oxo, aryl or cycloalkyl: hydroxymethyl or carboxy;
for alkoxyalkyl: methoxymethyl;
for alkoxycarbonyl: methoxycarbonyl or ethoxycarbonyl;
for alkylaminocarbonyl: methylaminocarbonyl or dimethylaminocarbonyl;
for aminoalkyl optionally substituted by hydroxy, alkylamino, alkoxy, oxo, aryl or cycloalkyl: aminomethyl, $CONH_2$ or $CH_2CONH_2$;
for alkylamino optionally substituted by hydroxy, alkylamino, alkoxy, oxo, aryl or cycloalkyl: (1–6C) alkanoylamino, such as acetylamino;
for alkoxycarbonylamino: methoxycarbonylaminno, ethoxycarbonylamino or t-butoxycarbonylamino;
amino;
for halo: fluoro, chloro or bromo;
cyano;
nitro;
thiol;
for alkylthio: methylthio($CH_3S$—);
for alkylsulphonyl: methylsulphonyl ($CH_3SO_2$—) or ethylsulphonyl ($CH_3CH_2SO_2$—);
for alkylsulphenyl: methylsulphenyl ($CH_3SO$—);
for alkylsulphonamido: methylsulphonylamido or ethylsulphonylamido;
for alkylaminosulphonyl: methylaminosulphonyl or ethylaminosulphonyl;
aminosulphonyl;
for haloalkoxy: trifluoromethoxy;
for haloalkyl: trifluoromethyl;
for a group of formula —$C(X^3)N(R^{11})R^{12}$: pyrrolidin-1-ylcarbonyl, piperidin-1-ylcarbonyl or morpholin-1-ylcarbonyl; and
—$OCH_2O$— which is bonded to two adjacent ring atoms in Cy.

Examples of particular values for $R_{1c}$ are:
hydrogen;
hydroxyl;
for alkoxy: methoxy or ethoxy;
for alkyl optionally substituted by hydroxy, alkylamino, alkoxy, oxo, aryl or cycloalkyl: alkyl, such as methyl or ethyl, or alkylaminoalkyl, such as methylaminomethyl or dimethylaminomethyl;

for hydroxyalkyl: hydroxymethyl;
for alkoxyalkyl: methoxymethyl;
for alkoxycarbonyl: methoxycabonyl or ethoxycarbonyl;
for alkylaminocarbonyl: methylaminocarbonyl or dimethylaminocarbonyl;
for alkoxycarbonylamino: methoxycarbonylamino, ethoxycarbonylamino or t-butoxycarbonylamino;
for alkylamino optionally substituted by hydroxy, alkylamino, alkoxy, oxo, aryl or cycloalkyl: (1–6C) alkanoylamino, such as acetylamino; and
for aminoalkyl substituted by hydroxy, alkylamino, alkoxy, oxo, aryl or cycloalkyl: aminomethyl, $CONH_2$ or $CH_2CONH_2$.

Preferably $R_{3a}$ is hydrogen, hydroxyl, methoxy, methyl, amino, fluoro, chloro, ethylsulphonylamino, amido or methylaminocarbonyl.

Examples of particular values for Cy are phenyl, 4-aminophenyl, 4-amidophenyl, 4-(N-methyl)amidophenyl, 4-(N,N-dimethyl)amidophenyl, 2-chlorophenyl, 2-methylphenyl, 2-fluorophenyl, 3-fluorophenyl, 4-fluorophenyl, 4-hydroxphenyl, 2-methoxyphenyl, 4-methoxyphenyl, 4-carboxyphenyl, 3-ethylsulphonylaminophenyl, thien-2-yl, thien-3-yl, thiazol-4-yl, thiazol-5-yl, 2-methylthiazol-4-yl, pyrid-2-yl, pyrid-3-yl, pyrid-4-yl, piperidin-4-yl, 1-methylpiperidin-4-yl, cyclohexyl and naphth-1-yl. Other examples are: 4-carbamoylphenyl; furan-2-yl; furan-3-yl; imidazol-2-yl; thiazol-2-yl; 2-aminothiazol-4-yl; isoquinolin-5-yl; isoquinolin-8-yl; quinolin-5-yl; and quinolin-8-yl. Further examples are: 2-trifluoromethylphenyl; 2-methylthiophenyl; 2-methylsulphonylphenyl; 3-bromophenyl; 3-cyanophenyl; and benzo[b]thiophen-3-yl.

Particular mention is made of the following values for Cy:

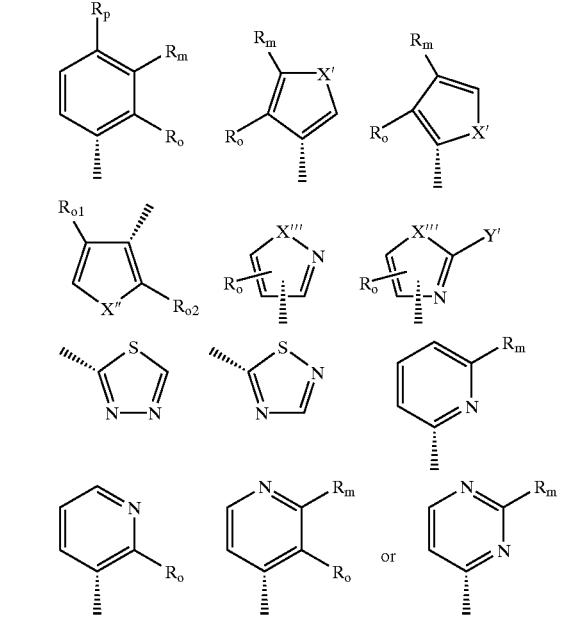

wherein:
X' is selected from O, S and NMe;
X'' is selected from O and S;
X''' is selected from O, S, NH and NMe;
Y' is selected from hydrogen, amino and methyl;
$R_o$ is selected from hydrogen, methyl, fluoro, chloro, trifluoromethyl, methoxy, methylthio, methylsulphinyl and methylsulphonyl;
$R_m$ is selected from hydrogen, methyl, fluoro, chloro, trifluoromethyl, methoxy, methylthio, methylsulphinyl, methylsulphonyl, carboxy, methoxycarbonyl and a group of the formula —C($X^3$)N($R^{11}$)$R^{12}$ (wherein $X^3$ is O or S, and $R^{11}$ and $R^{12}$ are independently selected from hydrogen, methyl or ethyl or together with the nitrogen atom to which they are attached form a pyrrolidin-1-yl, piperidin-1-yl or morpholino group);

$R_p$ is selected from hydrogen and fluoro; or $R_o$ and $R_m$ or $R_m$ and $R_p$ form an —OCH$_2$O— group; or $R_o$ and $R_m$ together with the ring to which they are attached form a 5 or 6 membered aryl or heteroaryl ring (wherein the heteroary ring contains 1 or 2 heteroatoms selected from nitrogen, oxygen and sulfur); and one of $R_{o1}$ and $R_{o2}$ is hydrogen and the other is $R_o$.

Preferably, Cy is selected from phenyl (optionally substituted by methyl, ethyl, prop-2-yl, phenoxy, hydroxy, ethoxy, benzyloxy, prop-2-yloxy, nitro, amino, acetylamino, methylsufonylamino, dimethylamino, chloro, methoxy, trifluoromethyl, methylthio, methylsulfonyl, tert-butylthio, tert-butylsulfonyl, aminosulfonyl or carbamoyl), pyridyl, thienyl, furanyl, imidazolyl, thiazolyl (optionally substituted by amino or methyl), napthyl, isoquinolinyl and quinolinyl.

Preferably Cy is selected from phenyl, 2-chlorophenyl, 2-methoxyphenyl, 4-carbamoylphenyl, pyrid-2-yl, pyrid-3-yl, pyrid-4-yl, thien-2-yl, thien-3-yl, furan-2-yl, furan-3-yl, imidazol-2-yl, thiazol-2-yl, thiazol-4-yl, 2-amino-thiazol-4-yl, thiazol-5-yl, naph-1-thyl, isoquinolin-5-yl, isoquinolin-8-yl, quinolin-4-yl, quinolin-5-yl and quinolin-8-yl.

More preferably Cy is selected from phenyl, 2-chlorophenyl, 2-methoxyphenyl, 4-carbamoylphenyl, pyrid-2-yl, thien-2-yl, thien-3-yl, furan-2-yl, furan-3-yl, imidazol-2-yl, thiazol-2-yl, thiazol-4-yl, thiazol-5-yl and quinolin-4-yl.

A value for Cy of particular interest is phenyl.

Referring to the group $R_2$, examples of a 5 or 6 membered aromatic carbon ring optionally interrupted by a nitrogen, oxygen or sulphur ring atom are phenyl; pyrrolyl, such as 2-pyrrolyl; pyridyl, such as 3-pyridyl; pyrazinyl, such as 2-pyrazinyl; furyl, such as 2-furyl; and thienyl, such as 2-thienyl or 3-thienyl. Preferably the ring is interrupted (i.e. a carbon atom is replaced) by at most one heteroatom. More preferably the ring is phenyl, 2-thienyl or 2-pyrrolyl. Most preferably, the ring is phenyl.

When the ring is phenyl, the group $R_2$ may be a group of formula

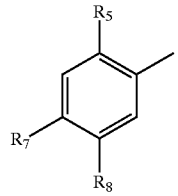

in which $R_5$ is amino, hydroxy or hydrogen, and $R_6$ and $R_7$ which may be the same or different represent halo, nitro, thiol, cyano, haloalkyl, haloalkoxy, amido, hydrazido, amino, alkylthio, alkenyl, alkynyl or $R_1$ or taken together form a 5 or 6 membered fused carbocyclic ring or 5 membered heterocyclic ring, which may itself be substituted by $R_{1j}$, amino, halo, cyano, nitro, thiol, alkylthio, haloalkyl, haloalkoxy.

When the substituents at the 3 and 4 positions taken together form a fused ring which is a 5 or 6 membered carbocyclic or heterocyclic ring, examples of the resultant bicyclic ring are naphthyl, such as 2-naphthyl; benzimidazolyl, such as benzimidazol-5-yl or benzimidazol-6-yl; isoquinolinyl, such as isoquinolin-7-yl; indolyl, such as indol-2-yl, indol-5-yl or indol-6-yl; indazolyl, such as indazol-5-yl; indazol-6-yl; 3,4-methylenedioxyphenyl; dihydroindolyl, such as 2,3-dihydroindol-6-yl; benzothiazolyl, such as benzothiazol-2-yl or benzothiazol-6-yl; benzo[b]thiophenyl, such as benzo[b]thiophen-2-yl; benzofuryl, such as benzofur-2-yl; imidazo[1,2-a]pyrimidinyl, such as imidazo[1,2-a]pyrimidin-2-yl; tetrahydroimidazo[1,2-a]pyrimidinyl, such as tetrahydroimidazo[1,2-a]pyrimidin-2-yl; and benzisoxazolyl, such as benzisoxazol-5-yl.

Preferably $R_2$ is phenyl, thien-2-yl, naphthyl, indol-2-yl, indol-6-yl, benzo[b]furan-5-yl, benzo[b]thiophen-2-yl or benzimidazol-2-yl, optionally substituted as defined hereinabove.

$R_2$ preferably represents:

(i) phenyl optionally being substituted in the 3 and/or 4 position by halo, nitro, thiol, haloalkoxy, hydrazido, alkylhydrazido, amino, cyano, haloalkyl, alkylthio, alkenyl, alkynyl, acylamino, tri or difluoromethoxy, carboxy, acyloxy, MeSO$_2$— or $R_1$, and optionally substituted at the 6 position by amino, hydroxy, halo, alkyl, carboxy, alkoxycarbonyl, cyano, amido, aminoalkyl, alkoxy or alkylthio;

(ii) naphth-2-yl optionally substituted at the 6 or 7 position by halo, haloalkoxy, haloalkyl, cyano, nitro, amino, hydrazido, alkylthio, alkenyl, alkynyl or $R_{1j}$ and optionally substituted at the 3 position by amino, hydroxy, halo, alkyl, carboxy, cyano, amido, aminoalkyl, alkoxy or alkylthio;

(iii) isoquinolin-7-yl, indol-5-yl, indol-6-yl, indazol-5-yl, indazol-6-yl, benzothiazol-6-yl or benzisoxazol-5-yl optionally substituted at the 3 position by halo, haloalkoxy, haloalkyl, cyano, nitro, amino, hydrazido, alkylthio, alkenyl, alkynyl or $R_{1j}$;

(iv) benzimidazol-5-yl or benzothiazol-6-yl optionally substituted at the 2 position by amino;

(v) thien-2-yl or thien-3-yl optionally substituted at the 4 or 5 position by halo, haloalkoxy, haloalkyl, cyano, nitro, amino, hydrazido, alkylthio, alkenyl, alkynyl or $R_1$;

(vi) 3,4-methylenedioxyphenyl, 2,3-dihydroindol-6-yl, 3,3-dichloro-2-oxo-indol-6-yl or 1-methyl-3-aminoindazol-5-yl;

(vii) benzothiazol-2-yl, imidazo[1,2-a]pyrimidin-2-yl or tetrahydroimidazo[1,2-a]pyrimidin-2-yl;

(viii) pyrazol-2-yl optionally substituted at the 5 position by halo, haloalkoxy, haloalkyl, cyano, nitro, amino, hydrazido, alkylthio, alkenyl, alkynyl or $R_1$;

(ix) pyrid-2-yl optionally substituted at the 5 position by halo, haloalkoxy, haloalkyl, cyano, nitro, amino, hydrazido, alkylthio, alkenyl, alkynyl or $R_1$;

(x) pyrid-3-yl optionally substituted at the 6 position by halo, haloalkoxy, haloalkyl, cyano, nitro, amino, hydrazido, alkylthio, alkenyl, alkynyl or $R_1$;

(xi) benzofur-2-yl optionally substituted at the 3 position by amino, hydroxy, halo, alkyl, carboxy, cyano, amido, aminoalkyl, alkoxy or alkylthio and at the 5 or 6 position by halo, haloalkoxy, haloalkyl, cyano, nitro, amino, hydrazido, alkylthio, alkenyl, alkynyl or $R_{1j}$;

(xii) indol-2-yl optionally substituted on the indole nitrogen atom by alkyl and optionally substituted at the 5 or 6 position by halo, haloalkoxy, haloalkyl, cyano, nitro, amino, hydrazido, alkylthio, alkenyl, alkynyl or $R_{1j}$;

(xiii) indol-6-yl substituted at the 5 position by amino, hydroxy, halo (such as fluoro or chloro), alkyl, carboxy, alkoxycarbonyl, cyano, amido, aminoalkyl, alkoxy or alkylthio and optionally substituted at the 3 position by halo (such as chloro), haloalkoxy, haloalkyl, cyano, nitro, amino, hydrazido, alkylthio, alkenyl, alkynyl or $R_{1j}$; or (xiv) benzo[b]thiophen-2-yl optionally substituted at the 3 position by amino, hydroxy, halo, alkyl, carboxy, cyano, amido, aminoalkyl, alkoxy or alkylthio and at the 5 or 6 position by halo, haloalkoxy, haloalkyl, cyano, nitro, amino, hydrazido, alkylthio, alkenyl, alkynyl or $R_{1j}$.

Examples of particular values for substituents that may be present on $R_2$ are:

for halo: fluoro, chloro, bromo or iodo;
nitro;
thiol;
for haloalkoxy: difluoromethoxy or trifluoromethoxy;
hydrazido;
for alkylhydrazido: methylhydrazido;
amino;
cyano;
for haloalkyl: trifluoromethyl;
for alkylthio: methylthio;
for alkenyl: vinyl;
for alkynyl: ethynyl;
for acylamino: acetylamino;
carboxy;
for acyloxy: acetoxy;
hydroxy;
for alkyl: methyl or ethyl;
amido ($CONH_2$);
for aminoalkyl: aminomethyl; and
for alkoxy: methoxy or ethoxy.

Preferably $R_2$ is optionally substituted by 1 or 2 substituents selected from fluoro, chloro, amino, methyl, ethyl and methoxy.

Examples of particular values for $R_1$ are:
hydrogen;
hydroxy;
for alkoxy: methoxy or ethoxy;
for alkyl optionally substituted by hydroxy, alkylamino, alkoxy, oxo, aryl or cycloalkyl: alkyl, such as methyl or ethyl, alkylaminoalkyl, such as dimethylaminomethyl, or alkanoyl, such as acetyl;
for hydroxyalkyl: hydroxymethyl;
for alkoxyalkyl: methoxymethyl;
for alkoxycarbonyl: methoxycarbonyl;
for alkylaminocarbonyl: methylaminocarbonyl;
for alkylamino: methylamino, ethylamino or dimethylamino;
for hydroxyalkyl substituted by hydroxy, alkylamino, alkoxy, oxo, aryl or cycloalkyl: carboxyl or carboxymethyl; and
for aminoalkyl substituted by hydroxy, alkylamino, alkoxy, oxo, aryl or cycloalkyl: amido ($CONH_2$) or amidomethyl.

Examples of particular values for $R_{1j}$ are:
hydrogen;
hydroxy;
for alkoxy: methoxy or ethoxy;
for alkyl optionally substituted by hydroxy, alkylamino, alkoxy, oxo, aryl or cycloalkyl: alkyl, such as methyl or ethyl, or alkanoyl, such as acetyl;
for hydroxyalkyl: hydroxymethyl;
for alkoxyalkyl: methoxymethyl;
for alkoxycarbonyl: methoxycarbonyl;
for alkylamino: methylamino, ethylamino or dimethylamino;
for hydroxyalkyl substituted by hydroxy, alkylamino, alkoxy, oxo, aryl or cycloalkyl: carboxyl or carboxymethyl; and
for aminoalkyl substituted by hydroxy, alkylamino, alkoxy, oxo, aryl or cycloalkyl: amido ($CONH_2$) or amidomethyl.

More preferably $R_2$ represents:

(i) phenyl optionally being substituted in the 3 and/or 4 position by fluoro, chloro, bromo, iodo, nitro, difluoromethoxy, trifluoromethoxy, amino, cyano, trifluoromethyl, methylthio, vinyl, carboxy, acetoxy, $MeSO_2$—, hydroxy, methoxy, ethoxy, methyl, methoxycarbonyl, methylamino, ethylamino or amido, and optionally substituted at the 6 position by amino, hydroxy, fluoro, methoxycarbonyl, cyano or aminomethyl (preferably phenyl substituted in the 4 position by chloro, amino, vinyl, methylamino, methyl or methoxy, optionally at the 3 position with amino or hydroxy, and optionally at the 6 position with amino or hydroxy);

(ii) naphth-2-yl optionally substituted at the 6, position by hydroxy and optionally substituted at the 3 position by amino or hydroxy;

(iii) isoquinolin-7-yl, indol-5-yl, indol-6-yl, indazol-5-yl, indazol-6-yl, benzothiazol-6-yl or benzisoxazol-5-yl optionally substituted at the 3 position by chloro, bromo, amino, methyl or methoxy (preferably indol-6-yl optionally substituted at the 3 position by chloro, bromo, methyl or methoxy);

(iv) benzimidazol-5-yl or benzothiazol-6-yl optionally substituted at the 2 position by amino;

(v) thien-2-yl or thien-3-yl optionally substituted at the 4 or 5 position by methylthio, methyl or acetyl;

(vi) 3,4-methylenedioxyphenyl, 2,3-dihydroindol-6-yl, 3,3-dichloro-2-oxo-indol-6-yl or 1-methyl-3-aminoindazol-5-yl;

(vii) benzothiazol-2-yl, imidazo[1,2-a]pyrimidin-2-yl or tetrahydroimidazo[1,2-a]pyrimidin-2-yl;

(viii) pyrazol-2-yl substituted at the 5 position by methyl;

(ix) pyrid-2-yl optionally substituted at the 6 position by chloro;

(x) pyrid-3-yl optionally substituted at the 4 position by chloro;

(xi) benzofur-2-yl optionally substituted at the 3 position by chloro, methyl or methoxy, at the 5 or 6 position by methyl and at the 6 position by methoxy;

(xii) indol-2-yl optionally substituted on the indole nitrogen atom by methyl and optionally substituted at the 5 or 6 position by fluoro, chloro, bromo, methyl or methoxy;

(xiii) indol-6-yl substituted at the 5 position by chloro, fluoro or hydroxy and optionally substituted at the 3 position by chloro or methyl; or (xiv) benzo[b]thiophen-2-yl optionally substituted at the 3 position by fluoro, chloro or methyl, and optionally substituted at the 5 or 6 position by fluoro, chloro, methyl, hydroxy, or methoxy.

Examples of particular values for $R_2$ are:
(i) phenyl, 2-aminophenyl, 3-aminophenyl, 2-amino-3-fluorophenyl, 2-amino-4-fluorophenyl, 2-amino-4-chlorophenyl, 2-amino-3-bromophenyl, 2-amino-3-nitrophenyl, 2-amino-4-nitrophenyl, 3,4-dimethoxy-5-aminophenyl, 2-amino-4-methylphenyl, 2-amino-3-methylphenyl, 2-amino-3-methoxyphenyl, 3,4-diaminophenyl, 3,5-diaminophenyl, 3-amino-4-fluorophenyl, 3-amino-4-chlorophenyl, 3-amino-4-bromophenyl, 3-amino-4-hydroxyphenyl, 3-amino-4-carboxymethylphenyl, 3-amino-4-methylphenyl, 3-amino-4-methoxyphenyl, 2-fluorophenyl, 4-fluoro-3-cyanophenyl, 3-chlorophenyl, 3-chloro-4-hydroxphenyl, 3-chloro-5-hydroxyphenyl, 4-chlorophenyl, 4-chloro-2-hydroxyphenyl, 4-chloro-3-hydroxyphenyl, 4-chloro-3-methylphenyl, 4-chloro-3-methoxyphenyl, 4-bromophenyl, 4-bromo-3-methylphenyl, 4-iodophenyl, 2-cyanophenyl, 3-cyanophenyl, 4-cyanophenyl, 3-cyano-5- aminophenyl, 2-hydroxphenyl, 2-hydroxy-4-methoxyphenyl, 3-hydroxphenyl, 3-hydroxy-4-methylphenyl, 2,4-dihydroxyphenyl, 3,4-dihydroxyphenyl, 3-hydroxy-4-methoxyphenyl, 4-difluoromethoxyphenyl, 4-trifluoromethoxphenyl, 4-trifluoromethylphenyl, 4-methylthiophenyl, 4-methoxycarbonylphenyl, 4-acetoxyphenyl, 4-methanesulfonylphenyl, 3-methylphenyl, 3-methyl-5-aminophenyl, 4-methylphenyl, 4-vinylphenyl, 4-methoxyphenyl, 4-ethoxyphenyl, 4-methoxy-3-chlorophenyl, 4-methoxy-3-methylphenyl, 3-methylaminophenyl, 4-methylaminophenyl, 4-ethylaminophenyl or 2-aminomethylphenyl;

(ii) naphth-2-yl, 3-aminonaphth-2-yl, 3-hydroxynaphth-2-yl or 6-hydroxynaphth-2-yl;

(iii) isoquinolin-7-yl, indol-5-yl, indol-6-yl, 3-chloroindol-6-yl, 3-bromoindol-6-yl, 3-methylindol-6-yl, 3-methoxyindol-6-yl, indazol-5-yl, 3-aminoindazol-5-yl, indazol-6-yl, benzothiazol-6-yl, 3-aminobenzisoxazol-5-yl;

(iv) benzimidazol-5-yl, 2-aminobenzimidazol-5-yl, or benzothiazol-6-yl;

(v) thien-2-yl, 5-methylthien-2-yl, 5-methylthio-thien-2-yl, 5-acetylthien-2-yl or thien-3-yl;

(vi) 3,4-methylenedioxyphenyl, 2,3-dihydroindol-6-yl, 3,3-dichloro-2-oxo-indol-6-yl or 1-methyl-3-aminoindazol-5-yl;

(vii) benzothiazol-2-yl, imidazo[1,2-a]pyrimidin-2-yl or tetrahydroimidazo[1,2-a]pyrimidin-2-yl;

(viii) 5-methylpyrazol-2-yl;

(ix) 5-chloropyrid-2-yl;

(x) pyrid-3-yl, 6-chloropyrid-3-yl;

(xi) benzofur-2-yl, 5-chlorobenzofur-2-yl, 3-methylbenzofur-2-yl, 5-methylbenzofur-2-yl, 6-methoxybenzofur-2-yl;

(xii) indol-2-yl, 5-fluoroindol-2-yl, 5-chloroindol-2-yl, 5-methylindol-2-yl, 5-methoxindol-2-yl, 6-methoxyindol-2-yl and 1-methyl-indol-2-yl, (xiii) 5-fluoroindol-6-yl; or (xiv) benzo[b]thiophen-2-yl, 5-chloro-benzo[b]thiophen-2-yl or 6-chlorobenzo[b]thiophen-2-yl.

$R_2$ may, for example, be selected from one of the formula (A') to (H'):

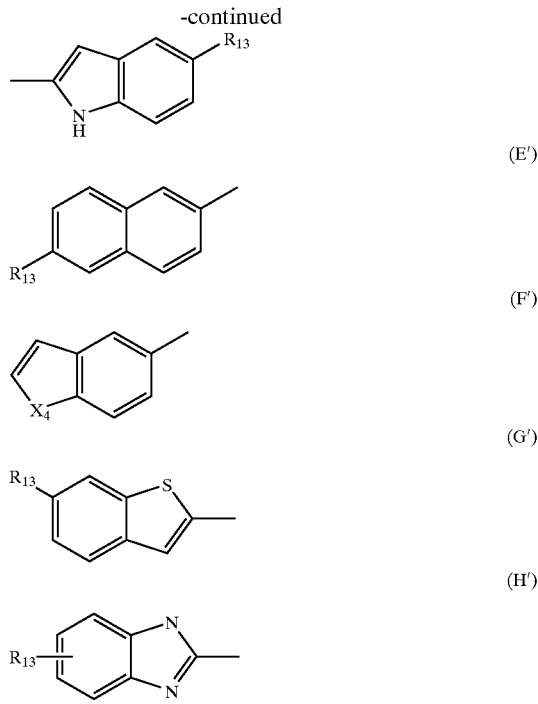

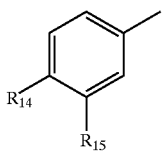

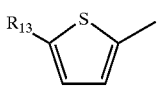

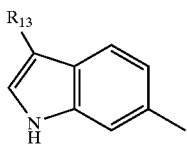

wherein $X_4$ is O or S, $R_{13}$ is selected from hydrogen, chloro or methyl and $R_{14}$ is selected from hydrogen, methyl, ethyl, fluoro, chloro, and methoxy and $R_{15}$ is selected from hydrogen, methyl, fluoro, chloro and amino.

Preferably $R_2$ is of the formula (A') (wherein $R_{14}$ is selected from hydrogen, methyl, ethyl, fluoro, chloro, and methoxy and $R_{15}$ is selected from hydrogen, methyl, fluoro, chloro and amino) or of the formula (B') (wherein $R_{13}$ is chloro) or of the formula (C') (wherein $R_{13}$ is selected from hydrogen, methyl and chloro) or of the formula (D') (wherein $R_{13}$ is selected from hydrogen, methyl, fluoro and chloro) or of the formula (E') (wherein $R_{13}$ is hydrogen) or of the formula (G') (wherein $R_{13}$ is chloro).

More preferably $R_2$ is 4-methoxyphenyl, 5-chloroindol-2-yl, 3-chloroindol-6-yl, indol-6-yl or 3-methylindol-6-yl.

$R_2$ is preferably of the formula (A') and $R_{14}$ and $R_{15}$ are as defined hereinabove. More preferably $R_2$ is of the formula (A') and $R_{14}$ is methoxy and $R_{15}$ is hydrogen.

It is preferred that at least one of $R_6$ and $R_7$ be other than hydrogen and that $R_6$, if present, is preferably a substituent containing one or more polar hydrogens such as hydroxy, amino, alkylamino, alkylaminoalkyl, aminocarbonyl, alkylaminocarbonyl, hydrazo and alkylhydrazo; alternatively $R_6$ and $R_7$ are joined together in the formation of a naphthyl or indolyl or azaindolyl or diazaindolyl group.

It is especially preferred that $R_6$ be amino and $R_7$ be chloro, bromo, methyl, methoxy or vinyl; or that $R_6$ and $R_7$ taken together form an indolyl ring with the NH at the 6-position or taken together form a naphthyl ring.

Compounds of particular interest are 1-(indol-6-carbonyl-D-phenylglycinyl)-4-(4-pyridoxy)piperidine and 1-[indole-6-carbonyl-D,L-(2-chlorophenyl)glycinyl]-4-(pyridin-4-yloxy)piperidine, and their physiologically-tolerable salts, especially compounds in the D-conformation. Compounds in this group have been found to have good oral exposure and a desirable pharmacological/toxicological profile.

The compounds of the invention may be prepared by conventional chemical synthetic routes or by routes as illustrated by the following examples.

The compounds of the formula (I) may be prepared by forming the —X—X— bond from appropriate intermediates. For example, when —X—X— is —CONH— or —CO—NR$_{1a}$—, by reacting a compound of the formula (10): H$_2$N—Y-(Cy)-L-Lp(D)$_n$ with a compound of the formula R$_2$—COOH, under conditions known for the formation of an amide bond. The reaction is conveniently carried out in the presence of a benzotriazole-based reagent such as 1-hydroxybenzotriazole or 1-hydroxy-7-azabenzotriazole, in an inert organic solvent such as dimethylformamide and/or methylene chloride. The reaction mixture is usually taken to 0° C. and then a dehydrating agent such as dicyclohexylcarbodiimide or 1-(3-dimethylaminopropyl)-3-ethylcarbodiimide added. Other suitable reagents and solvents are known in the art. Other suitable reagents and solvents are known in the art. For example, an acid of formula R$_2$COOH may be converted into an acid halide, such as an acid chloride, and then reacted with the compound of formula (10) in the presence of a base, such as pyridine. Another reagent is diethyl cyanophosphonate.

Compounds wherein —X—X— is —NHCO— or —NHCH$_2$— may be formed from the appropriate intermediates using reaction conditions for the formation of an amide bond as described above and if necessary subsequent reduction of the resulting amide bond. Alternatively, a compound of formula (10) may be reacted with a compound of formula R$_2$CHO to form an intermediate of the formula (I) wherein —X—X— is —C═N—, which is then reduced with a reducing agent such as sodium cyanoborohydride.

Compounds of the formula (I) wherein —X—X— is of the formula —CH$_2$NH— may be prepared by reducing the corresponding compound of the formula (I) wherein —X—X— is —CONH—.

When —X—X— is —CH═CH—, the compounds of the formula (I) may be prepared using the Wittig or Horner-Emmons reactions. The corresponding compound in which —X—X— is —CH$_2$CH$_2$— can be formed by reduction of the —CH═CH— group, for example with hydrogen over a palladium-on-carbon catalyst.

An —X—X— bond of the formula —COO— or —OC(O)— may be formed by reacting the appropriate hydroxy and activated carboxylic acid (e.g. acid chloride or reactive ester) intermediates under conditions known for ester bond formation. Alternatively, a hydroxy and a carboxylic acid intermediate could be reacted together in the presence of a diethylazodicarboxylate/triphenylphosphine.

An —X—X— bond of the formula —CH$_2$O— or —OCH$_2$— may be formed by reacting the appropriate hydroxy intermediate with the appropriate alkyl halide in the presence of a base. Conditions for the formation of an ether bond are known in the art.

These reactions can also be used to form intermediates, which contain one of the above —X—X— bonds.

Compounds of the formula (I) in which Q is O may also be prepared by coupling a compound of the formula (11):

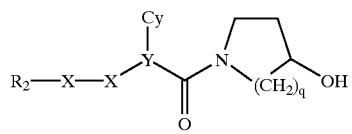

with a compound of formula (12)

HO—R$_q$

The reaction is conveniently performed in the presence of a coupling agent, such as 2-triphenylphosphonium 4,4-dimethyltetrahydro-1,2,5-thiadiazolidine 1,1-dioxide (Reference: J. Castro et al. J. Org. Chem. 1994, 59, 2289–2291) or triphenylphosphine/diethyl diazodicarboxylate (DEAD). Convenient solvents include aromatic hydrocarbons, such as benzene, and ethers, such as tetrahydrofuran. The coupling is conveniently effected at a temperature in the range of from −25 to 10° C.

The intermediates of formula (11) are believed to be novel, and are provided as a further aspect of the invention.

The intermediates of formula (11) in which X—X is CONH may be prepared by reacting a compound of formula (13)

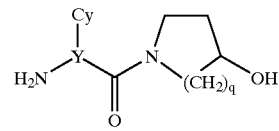

with a compound of formula R$_2$—COOH, under conditions known for the formation of an amide bond, for example as described hereinabove for forming a compound of formula (I).

The compounds of formula (13) may be prepared by reacting an appropriate N-protected glycine of formula (14)

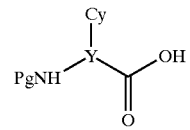

in which Pg represents an amino protecting group, such as benzyloxycarbonyl, with a compound of formula (15)

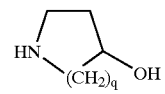

under amide bond forming conditions, followed by removing the protecting group Pg.

Compounds of the formula (I) in which Q is NH may also be prepared by reacting a compound of the formula (16):

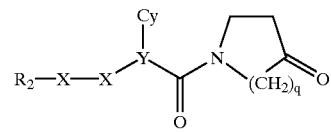

with an amine of formula (17)

H$_2$N—R$_q$ and reducing the resultant imine. The reaction with the amine and reduction may be effected sequentially or in one step (reductive amination). Convenient reducing agents include borohydrides, such as NaBH$_4$ or NaHB(OAc)$_3$, or hydrogen in the presence of a Group VIII metal catalyst, such as palladium on charcoal. Convenient solvents include lower alkanols, such as methanol or ethanol and optionally as co-solvents, halogenated hydrocarbons, such as dichloromethane or 1,2-dichloroethane.

The intermediates of formula (16) are believed to be novel, and are provided as a further aspect of the invention.

Compounds of formula (16) may be prepared by oxidising a compound of formula (11), for example using oxalyl chloride/dimethylsulfoxide in dichloromethane.

The reaction of a ketone of formula (16) with an amine of formula (17) may also be applied to the preparation of intermediates of formula (18) and (19)

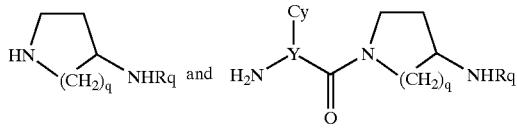

with any reactive groups being provided with appropriate protection (for example using a t-butoxycarbonyl or benzyl protecting group).

Intermediates of formula (18) may also be prepared by reacting a protected compound of formula (20)

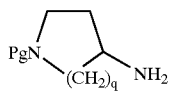

in which Pg represents a protecting group, such a t-butoxycarbonyl, with a compound of formula (21)

$Z_a$-$R_q$ in which $Z_a$ represents a halogen atom, such as a chlorine or bromine atom, in the presence of a palladium catalyst, followed by removal of the protecting group Pg.

The oxidation reaction used to prepare compounds of formula (16) may also be applied to the preparation of intermediates of formula (22)

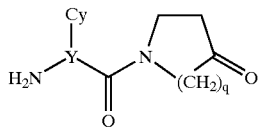

with the amino group being provided with appropriate protection during the oxidation (for example with a benzyloxycarbonyl or t-butoxycarbonyl protecting group).

A compound of formula (10) may be prepared by reacting a compound of formula (14) with a compound of formula (24)

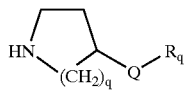

under amide bond-forming conditions to afford a compound of formula (25)

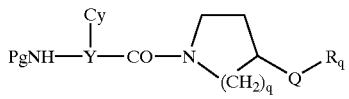

followed by removal of the protecting group Pg.

A compound of formula (24) may be prepared by deprotecting a compound of formula (26)

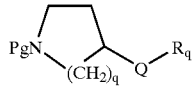

in which Pg represents a protecting group, such as t-butoxycarbonyl.

A comound of formula (26) may be prepared by reacting a compound of formula

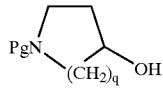

with a compound of formula (21) in the presence of a base, such as sodium hydride.

A compound of formula (25) in which Q is O may be prepared by reacting a compound of formula (27)

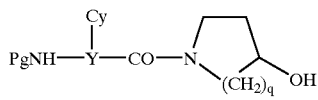

with a compound of formula (12) as described for the reaction of a compound of formula (11) with a compound of formula (12).

Hence the present invention also provides a process for the preparation of a compound of formula (I) comprising:
a) when —X—X is —CONH—, reacting a compound of formula (10) with a compound of formula $R_2$—COOH, under amide bond-forming conditions;
b) when Q is O, reacting a compound of formula (11) with a compound of (12); or
c) when Q is NH, reacting a compound of formula (16) with a compound of formula (17);
wherein $R_2$, X, Y, Cy, q and $R_q$ are as hereinabove defined and formulae (10), (11), (12), (16) and (17) are as hereinabove defined, followed if a salt is required, by forming a physiologically acceptable salt.

An amino acid of formula (23)

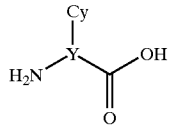

or an N-protected glycine of formula (14) may be prepared (for example) by one or more of the following methods:
(i) from aryl or heteroaryl aldehydes via the Strecker synthesis or modifications thereof, via Bucherer-Bergs hydantoin synthesis, or via the Ugi methodology ("Isonitrile Chemistry", Ugi I. Ed.; Academic: New York, 1971;145–1999, "Multicomponent Reactions with Isocyanides", Domling, A.; Ugi, I. *Angew. Chem. Int. Ed.* 2000, 39, 3168; "Amino Acid Derivatives by Multicomponent Reactions", Dyker, G. *Angew, Chem. Int. Ed. Engl.* 1997, 36, 1700; and also see "A new Class of Convertible Isocyanides in the Ugi Four-Component Reaction", Lindhorst, T.; Bock H.; Ugi, I. *Tetrahedron*, 1999, 55, 7411.) with removal and replacement of protecting groups;

(ii) from styrenes via Sharpless methodology (J. Am. Chem. Soc. 1998,120, 1207–1217)
(iii) from aryl boronic acids via Petasis methodology (Tetrahedron, 1997, 53, 16463–16470) with removal and replacement of protecting groups;
(iv) from aryl and heteroaryl acetic acids—via Evan's azidation (Synthesis, 1997, 536–540) or by oximation, followed by reduction and addition of protecting groups; or
(v) from existing aryl glycines by manipulation of functional groups, for example, alkylation of hydroxy groups, palladium assisted carbonylation of triflates derived from hydroxy groups and further manipulation of the carboxylic esters to give carboxylic acids by hydrolysis, carboxamides by activation of the carboxylic acid and coupling with amines, amines via Curtius reaction on the carboxylic acid, or alkylsulphonyl compounds by oxidation of alkylthio compounds; or
(vi) from aliphatic, carbocylic and non-aromatic heterocyclic aldehydes and ketones using a Horner-Emmons reaction with N-benzyloxycarbonyl)-α-phosphonoglycine trimethyl ester (Synthesis, 1992, 487–490);
(vii) from oximes of formula

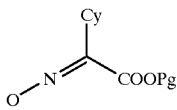

in which Pg is a carboxy protecting group, by reduction. (Oximes in which Cy is a heteroaryl group may be prepared from compounds of formula

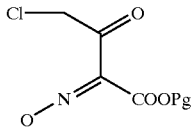

Alternatively, oximes may be prepared by nitrosation of a compound of formula Cy-CH$_2$—COOPg, or by reaction of hydroxylamine with a compound of formula Cy-CO—COOPg; or by any other method known in the art.

A starting material for the preparation of a compound of formula (I), where the alpha atom is nitrogen, may be produced, for example, by reaction of a beta protected hydrazine (such protection to be chosen as to be compatible with the subsequent reagents to be employed) with phosgene, diphosgene, triphosgene or N,N'carbonyl diimidazole to give a reactive compound of the type PGNHN(Cy)COCl or PGNHN(Cy)CO-imidazole (wherein PG is a protecting group).

This intermediate may be used as has been described above for the carboxylic starting reagents where the alpha atom is carbon.

The skilled person will be aware that at certain stages in the synthesis of a compound of formula (I) it may be necessary to protect a reactive functional group in the molecule to prevent unwanted side-reactions.

The protection of amino and carboxylic acid groups is described in McOmie, Protecting Groups in Organic Chemistry, Plenum Press, NY, 1973, and Greene and Wuts, Protecting Groups in Organic Synthesis, 2nd. Ed., John Wiley & Sons, NY, 1991. Examples of carboxy protecting groups include $C_1$–$C_6$ alkyl groups such as methyl, ethyl, t-butyl and t-amyl; aryl($C_1$–$C_4$)alkyl groups such as benzyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, benzhydryl and trityl; silyl groups such as trimethylsilyl and t-butyldimethylsilyl; and allyl groups such as allyl and 1-(trimethylsilylmethyl)prop-1-en-3-yl.

Examples of amine protecting groups (PG) include acyl groups, such as groups of formula RCO in which R represents $C_{1-6}$ alkyl, $C_{3-10}$ cycloalkyl, phenyl $C_{1-6}$ alkyl, phenyl, $C_{1-6}$ alkoxy, phenyl $C_{1-6}$ alkoxy, or a $C_{3-10}$ cycloalkoxy, wherein a phenyl group may be optionally substituted, for example by one or two of halogen, $C_1$–$C_4$ alkyl and $C_1$–$C_4$ alkoxy.

Preferred amino protecting groups include benzyloxycarbonyl (CBz), t-butoxycarbonyl (Boc) and benzyl.

In another aspect the invention relates to a process for preparing a compound of formula I comprising deprotecting a compound of formula (I'):

$$R^{2'}\text{—}X\text{—}X\text{—}Y(Cy')\text{-L-Lp(D)}_n{'} \quad \quad (I)'$$

Wherein $R^{2'}$ is $R^2$ (as hereinabove defined) or protected $R^2$, Cy' is Cy (as hereinabove defined) or protected Cy and Lp(D)$_n$' is Lp(D)$_n$ (as hereinabove defined) or protected Lp(D)$_n$; providing at least one protecting group is present.

If necessary physiologically tolerable salts can be formed using methods known in the art.

It will be understood that the compounds of formula (I) may be isolated in the form of salts or solvates (which may or may not be physiologically tolerable), and that all such salts and solvates are therefore included within the scope of the present invention.

All novel intermediates described herein are provided as further aspects of the invention.

The compounds of the invention may be administered by any convenient route, e.g. into the gastrointestinal tract (e.g. rectally or orally), the nose, lungs, musculature or vasculature or transdermally. The compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. Preferably the compositions will be sterile and in a solution or suspension form suitable for injection or infusion. Such compositions form a further aspect of the invention.

The following are examples of pharmaceutical compositions of compounds according to the invention.

| Formulation 1 Hard gelatin capsules are prepared using the following ingredients: | |
|---|---|
| | Quantity (mg/capsule) |
| Active Ingredient | 250 |
| Starch, dried | 200 |
| Magnesium stearate | 10 |
| Total | 460 mg |

The above ingredients are mixed and filled into hard gelatin capsules in 460 mg capsules.

Formulation 2
Tablets each containing 60 mg of active
ingredient are made as follows:

| | |
|---|---|
| Active Ingredient | 60 mg |
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

Viewed from this aspect the invention provides a pharmaceutical composition comprising a serine protease inhibitor according to the invention together with at least one pharmaceutically acceptable carrier or excipient. The pharmaceutical composition may also optionally comprise at least one further antithrombotic and/or thrombolytic agent.

Viewed from a further aspect the invention provides the use of a serine protease inhibitor according to the invention for the manufacture of a medicament for use in a method of treatment of the human or non-human animal body (e.g. a mammalian, avian or reptilian body) to combat (i.e. treat or prevent) a condition responsive to said inhibitor.

Viewed from a further aspect the invention provides a method of treatment of the human or non-human animal body (e.g. a mammalian, avian or reptilian body) to combat a condition responsive to a serine protease inhibitor (e.g. a condition such as a thrombotic disorder responsive to a factor Xa inhibitor) said method comprising administering to said body an effective amount of a serine protease inhibitor according to the invention.

The dosage of the inhibitor compound of the invention will depend upon the nature and severity of the condition being treated, the administration route and the size and species of the patient. However in general, quantities of from 0.01 to 100 $\mu$mol/kg bodyweight will be administered.

All publications referred to herein are hereby incorporated by reference.

The invention will now be described further with reference to the following non-limiting Examples.

Experimental

Abbreviations used follow IUPAC-IUB nomenclature. Additional abbreviations are HPLC or Hplc, high-performance liquid chromatography; rpHPLC, reverse phase HPLC; THF, tetrahydrofuran; HOAc, acetic acid; DMSO, dimethyl sulfoxide (perdeuterated if for NMR); EtOAc, ethyl acetate; EtOH, ethanol; DMF, dimethylformamide; DCM, dichloromethane; HOAt, 1-hydroxy-7-azabenzotriazole; HATU, [O-(7-azabenzotriazol-1-yl)-1,1,3,3-tetramethyluronium hexafluorophosphate]; Fmoc, 9-fluorenylmethoxycarbonyl; HOBt, 1-hydroxybenzotriazole; TBTU, 2-[1H-(benzotriazol-1-yl)]-1,1,3,3-tetramethyluronium-tetrafluoroborate; EDCI, 1-(3-dimethylaminopropyl)-3-ethylcarbodiimide hydrochloride; DIPEA, diisopropylethylamine; Boc, tertiary butyloxycarbonyl; DIPCI, diisopropylcarbodiimide; DBU, 1,8-diazabicyclo[5.4.0]undec-7-ene; DECP, diethylcyanophosphonate; TEA, triethylamine; Rink linker, p-[(R,S)-α-[1-(9H-fluoren-9-yl)methoxyformamido]-2,4-dimethoxybenzyl]phenylacetic acid; TFA, trifluoroacetic acid; MALDI-TOF, Matrix assisted laser desorption ionisation—time of flight mass spectrometry, RT, retention time. Amino acid derivatives, resins and coupling reagents were obtained, for example, from Novabiochem (Nottingham, UK) and other solvents and reagents from Rathburn (Walkerburn, UK) or Aldrich (Gillingham, UK) and were used without further purification. All solution concentrations are expressed as % Vol./% Vol. unless otherwise stated.

IR means an infrared spectrum was obtained. $^1$NMR, 1H-NMR, or 1H NMR means a proton magnetic resonance spectrum consistent with the structure was obtained.

In general in this specification, "D-" or "R-" in the name of a product indicates the product was made beginning with a chiral starting material, for example D-phenylglycine; however, racemization may have occurred, and the enantiomeric purity may not have been determined.

Purification:

Purification was by gradient reverse phase Hplc on a Waters Deltaprep 4000 at a flow rate of 50 mL/min using a Deltapak C18 radial compression column (40 mm×210 mm, 10–15 mm particle size). Eluant A consisted of aqueous TFA (0.1%) and eluant B of 90% CH$_3$CN in aqueous TFA (0.1%) with gradient elution (Gradient 1: 0 min 20% B, then 20% to 100% over 36 min; Gradient 2: 0 min 5% B for 1 min, then 5% B to 20% B over 4 min, then 20% to 60% over 32 min; or Gradient 3: 0 min 20% B, then 20% to 100% over 15 min). Fractions were analysed by analytical Hplc and MALDI-TOF before pooling those with >95% purity for lyophilisation.

Analysis:

Analytical Hplc was on a Shimadzu LC6 gradient system equipped with an autosampler, a variable wavelength detector at a flow rate of 0.4 mL/ min. Eluents A and B as for preparative Hplc. Columns used were Techogell5 C18 (2×150 mm)(Hplc Technology), Magellan C8 column (2.1× 150 mm, 5 $\mu$m particle size) and Luna C18 (2.1×150 mm, 5 $\mu$M particle size) (Phenomenex). Purified products were further analysed by MALDI-TOF and $^1$NMR.

Preparation of Starting Materials and Intermediates

Intermediate substituted glycine compounds for starting materials and intermediates, including those in which the amino group and/or the carboxy group is protected, conveniently may be prepared using one of the procedures below, or by a similar procedure. It may be convenient or preferred to change the order of steps in the preparation of a compound of the invention and to use a similar procedure with a different intermediate. In particular, it may be convenient to use an acyl group R$_2$—CO— initially in a preparation, rather than an amino protecting group.

Abbreviations, in addition to others listed herein, include: TEMPO: 2,2,6,6-tetramethyl-1-piperidinyloxy, free radical; (DHQD)$_2$PHAL: hydroquinidine 1,4-phthalazinediyl diether; r.b. or rb, round bottomed; PPh$_3$, triphenylphosphine; Boc$_2$O or Boc anhydride: di-tert-butyl dicarbonate.

Preparation of Intermediates KE-1–KE-5

The following compounds were prepared according to the indicated method (Method KE-A) from the indicated starting materials, unless otherwise described.

Intermediate KE-1
Ethyl oxo-quinolin-8-ylacetate.

Method KE-A

To a stirring solution of 8-bromoquinoline (10.1 g, 48.5 mmol) in THF (500 mL) at −78° C. was added dropwise a 1.3 M solution of sec-butyl lithium (37.3 mL, 48.5 mmol) in cyclohexane. After 5 min, diethyl oxalate (8 mL, 58.3 mmol) was added; and the solution was allowed to slowly warm to room temperature overnight. The next morning, the reaction was quenched with the addition of saturated aqueous NH$_4$Cl; and the solvent was removed in vacuo. The residue was partitioned between ethyl acetate and satd aq. NaHCO$_3$; the layers were separated; and then the aqueous phase was washed with brine, dried with MgSO$_4$, filtered and concentrated in vacuo. The residue was chromatographed over silica gel, eluting with 20% ethyl acetate/hexanes through 25% ethyl acetate/hexanes. The product containing fractions were combined and concentrated in vacuo to give 5.88 g (53%) of the title compound.

1H-NMR
IS-MS, m/e 230.1 (M+1)

Intermediate KE-2
Ethyl oxo-quinolin-5-ylacetate.
Prepared from 5-bromoquinoline and diethyl oxalate using Method KE-A.
1H-NMR
IS-MS, m/e 230.0 (M+1)

Intermediate KE-3
Ethyl oxo-thiazol-5-ylacetate.
To a r.b. flask (500 cm$^3$) under argon, fitted with ethanol thermometer, septum cap, and dropping funnel, was added anhydrous ether (100 cm$^3$) with stirring. This was cooled to −78° C. and 2 M n-butyllithium (60 cm$^3$, 120 mmol) was added.

A solution of silyl thiazole (16 g, 16 cm$^3$, 100 mmol) in anhydrous ether (100 cm$^3$) was then added by dropping funnel over 30 minutes. This was allowed to stir for 1 hour to give a peach suspension. To this was added diethyl oxalate (16.3 cm$^3$, 17.5 g, 120 mmol) rapidly to give a brown solution, resulting in a temperature increase to −30° C. This was allowed to cool back to −78° C. and stirred for 30 minutes. Reaction monitored by $^1$H NMR (CDCl$_3$).

The brown solution was poured onto 5% hydrochloric acid solution (300 cm$^3$) with vigorous stirring for 30 minutes. Ether layer was separated and washed with saturated bicarbonate (ca. 80 cm$^3$), dried over magnesium sulphate, and concentrated in vacuo to give an orange oil. This was purified by flash chromatography (10% ethyl acetate/ hexane) to give a yellow oil (7.31 g, 39.47 mmol) [40% Yield].
$^1$H NMR (CDCl$_3$); 1.42 (3H, t), 4.45 (2H, q), 8.89 (1H, s), 9.10 (1H, s).

Intermediate KE-4
Ethyl oxo-thiazol-2-ylacetate.
Prepared from thiazole and diethyl oxalate using Method KE-A. In this case the temperature was held at −35° C. and n-butyllithium in hexane was used in place of sec-butyllithium in cyclohexane.
$^1$NMR
IS-MS, m/e 165.0 (M+1)

Intermediate KE-5
Ethyl oxo-isoquinolin-8-ylacetate.
Prepared from 8-bromoisoquinoline and diethyl oxalate using Method KE-A, substituting n-butyl lithium in hexanes for sec-butyl lithium in cyclohexane.

$^1$NMR
IS-MS, m/e 230.0 (M+1)

| Analysis for C$_{13}$H$_{11}$NO$_3$: |
| --- |
| Calcd: C, 68.11; H, 4.84; N, 6.11; |
| Found: C, 68.11; H, 5.00; N, 6.14. |

Preparation of Intermediates OX-1–OX-9
The following compounds were prepared according to the indicated method (Method OX-A or Method OX-B) from the indicated starting materials unless otherwise described.

Intermediate OX-1
Ethyl Hydroxyimino-pyridin-2-ylacetate.

Method OX-A

To a stirring solution of ethyl 2-pyridylacetate (12.6 g, 76.3 mmol) in acetic acid (19 ML) at 5° C. was added a solution of sodium nitrite (6.05 g, 87.7 mmol) in water (12 mL) at a rate sufficient to maintain the internal temperature below 15° C. After complete addition and an additional 30 min, an additional 30 mL of water were added. The resulting white precipitate was filtered, washed with water, satd aq. NaHCO$_3$, and again with water. The solid was then dried under vacuum to give 14.1 g (95%) of the title compound.
1H-NMR
IS-MS, m/e 194.9 (M+1)

| Analysis for C$_9$H$_{10}$N$_2$O$_3$: |
| --- |
| Calcd: C, 55.67; H, 5.19; N, 14.43; |
| Found: C, 55.79; H, 5.14; N, 14.13. |

Intermediate OX-2
Ethyl Hydroxyimino-pyridin-3-ylacetate.
Using the procedure of Tikk et al [Acta. Chimica, Hungarica, 114(3–4), 355], a mixture of ethyl hydroxyimino-pyridin-3-yl-acetate and n-butyl hydroxyimino-pyridin-3-yl-acetate was prepared from ethyl 3-pyridinylacetate and n-butyl nitrite.
1H-NMR
IS-MS, m/e 195 (M+1), 223.1 (M+1)

Intermediate OX-3
Ethyl Hydroxyimino-quinolin-8-ylacetate.

Method OX-B

To a stirring solution of ethyl oxo-quinolin-8-yl-acetate (5.5 g, 24 mmol) in ethanol (140 mL) was added sodium acetate (2.16 g, 26.4 mmol) followed by hydroxylamine hydrochloride (2.67 g, 38.4 mmol). The mixture was heated to reflux; and, after 7 h, the heating mantle was removed and the solution was allowed to stir overnight at room temperature. The next morning, the solvent was removed in vacuo and the residue was partitioned between ethyl acetate and satd aq. NaHCO$_3$. The layers were separated and the organic phase was washed with brine, dried with Na$_2$SO$_4$, filtered and concentrated in vacuo. The resulting foam was recrystalized from dichloromethane/hexanes to give an initial crop of 2.5 g of the title compound as an off-white solid, followed by 0.31 g of a second crop. The mother liquor was then concentrated in vacuo, the residue was dissolved in a minimal amount of dichloromethane. The solution was then chromatographed over silica gel, eluting with 30% ethyl acetate/hexanes, then 40% ethyl acetate/hexanes, and finally with ethyl acetate. The product containing fractions were combined and concentrated in vacuo to give 1.94 g of the title compound for a combined yield of 4.75 g (81%).
1H-NMR
IS-MS, m/e 245.0 (M+1)
Intermediate OX-4
Ethyl Hydroxyimino-quinolin-5-ylacetate.
Prepared from ethyl oxo-quinolin-5-yl-acetate using Method OX-B.
1H-NMR
IS-MS, m/e 245.0 (M+1)
Intermediate OX-5
Ethyl Hydroxyimino-thiazol-5-ylacetate.
To a r.b. flask (500 cm$^3$) was added the ethyl oxo-thiazol-5-ylacetate (6.30 g, 34.02 mmol) to ethanol (ca. 180 cm$^3$) with stirring. Sodium acetate (3.06 g, 37.30 mmol) and ydroxylamine hydrochloride (3.78 g, 54.43 mmol) were then added to give an off-white suspension. This was brought to reflux at 85° C. for 1 hour. Reaction monitored by TLC (60% hexane/ethyl acetate; s.m. r.f 0.5, prod. r.f. 0.3.). Reaction cooled and concentrated in vacuo. Product taken up in ethyl acetate (c.a. 200 cm$^3$) and washed with 5% hydrochloric acid solution. Ethyl acetate layer was dried over magnesium sulphate and evaporated to dryness to give a cream solid (6.372 g, 31.825 mmol) [94% Yield].
$^1$H NMR (CDCl$_3$); 1.40 (3H, m), 4.40 (2H, m), 8.06 (⅓H, s), 8.78 (⅓H, s), 8.95 (⅔H, 8.98 (⅔H, s).
Intermediate OX-6
Ethyl α-Oximino-thiazole-4-acetate.
To a 2 necked r.b. flask (100 cm$^3$) with ethanol thermometer, concentrated sulphuric acid (25 cm$^3$) was added and cooled to 0° C. with stirring. To this solution was added the ethyl α-oximino-2-aminothiazole-4-acetate (5.00 g, 23.231 mmol). Water (10 cm$^3$) was then added and cooled to −10° C. A solution of sodium nitrite (1.683 g, 24.393 mmol) in water (5 cm$^3$) was then added slowly over an hour keeping the temperature below −5° C.
To a separate r.b. flask (500 cm$^3$), water (180 cm$^3$) was added and cooled to 3° C. The reaction solution was poured in to the cold water with stirring and then cooled to −5° C. To this solution, 50% hypophosphoric acid (90 cm$^3$) was added dropwise over 10 minutes keeping the temperature at −5° C. The solution was allowed to warm to room temperature and stirred overnight. The product was extracted with diethyl ether (ca. 3×150 cm$^3$) and washed with water. The ether layer was concentrated in vacuo and treated to flash chromatography (50% ethyl acetate/n-hexane) to yield a orange oil upon concentration in vacuo (0.60 g, 3.00 mmol) [13% yield].
$^1$H NMR (CDCl$_3$) 1.35 (3H, m), 4.35 (2H, m), 8.4 (1H, s), 8.9 (1H, s), 14.4 (1H, s).
Intermediate OX-7
Ethyl α-Oximino-2-methylthiazole-4-acetate.
This was prepared from ethyl-γ-chloro-α-oximinoacetoacetate (1.44 g) using the method of Hatanaka et al. (*Journal of Medicinal Chemistry*, 1973, 16(9), 978–984) to yield the titled compound (0.64 g).
$^1$H NMR (CDCl$_3$) 1.35 (3H, t), 2.7 (3H, s), 4.35 (2H, q), 8.2 (1H, s).
Ethyl γ-Chloro-α-oximinoacetoacetate.
This was prepared from ethyl oximinoacetoacetate (1.73 g) using the method of Hatanaka et al. (*Journal of Medicinal Chemistry*, 1973, 16(9), 978–984) to yield the titled compound (1.44 g).
$^1$H NMR (CDCl$_3$) 1.25 (3H, t), 4.3 (2H, q), 4.55 (2H, s), 9.45 (1H, s), contains 20% starting material by NMR.

Ethyl Oximinoacetoacetate
This was prepared from ethyl acetoacetate (10.00 g) using the method of Fischer (*Organic Synthesis Coll.* Vol. 3, 513–516) to yield the titled compound (12.45 g).
$^1$H NMR (CDCl$_3$) 1.25 (3H, t), 2.35 (3H, s), 4.3 (2H, q), 8.8 (1H, br.).
Intermediate OX-8
Ethyl hydroxyimino-thiazol-2-ylacetate.
Prepared from ethyl oxo-thiazol-2-ylacetate using Method OX-B.
$^1$NMR
IS-MS, m/e 198.9(M−1)
Intermediate OX-9
Ethyl hydroxyimino-isoquinolin-8-ylacetate.
Prepared from ethyl oxo-isoquinolin-8-ylacetate using Method OX-B.
$^1$NMR
IS-MS, m/e 245.0(M+1)

| Analysis for $C_{13}H_{12}N_2O_3$: |
|---|
| Calcd: C, 63.93; H, 4.95; N, 11.47; |
| Found: C, 63.68; H, 4.60; N, 11.34. |

Preparation of Intermediates AL-1–AL-3
The following compounds were prepared according to the indicated method (Method AL-A or Method AL-B) from the indicated starting materials, unless otherwise described.
Intermediate AL-1
R-3-Bromo-(1-t-butoxycarbonylamino-2-hydroxyethyl)benzene.

Method AL-A

Sodium hydroxide (3.33 g, 83.25 mmol) was dissolved in water (220 mL), and 20 mL of the resulting solution was removed and added to potassium osmate (410 mg, 1.11 mmol). The remaining sodium hydroxide solution (200 mL) was added to stirred solution of t-butyl carbamate (9.9 g, 84.5 mmol) in n-propanol (110 mL) followed by freshly prepared t-butyl hypochlorite (9.65 mL; 83.5 mmol). After stirring for 5 min, the solution was cooled to 0° C. A solution of (DHQD)$_2$PHAL (1.30 g, 1.67 mmol) in n-propanol (110 mL) was added, followed by a solution of 3-bromostyrene (5 g, 27.31 mmol) in n-propanol (220 mL), followed by drop-wise addition of the potassium osmate/sodium hydroxide solution. The reaction was stirred overnight. Saturated aqueous sodium sulfite (150 mL) was added, and the reaction was stirred for 15 min. The aqueous layer was separated and extracted with ethyl acetate (3×200 mL). The combined organic layers were washed with brine and dried over MgSO$_4$. Removal of solvent under vacuum gave the crude product which was purified by chromatography (silica, 3:2 hexane:ethyl acetate then rechromatographed loading with toluene, gradient elution with hexane—4:1 hexane:ethyl acetate) to give the title product (4.18 g, 49%).
Melting Point=90–91° C.
$^1$H NMR (CDCl$_3$)
Intermediate AL-2
R-3-Methoxycarbonyl-(1-t-butoxycarbonylamino-2-hydroxyethyl)benzene.

Method AL-B

In a glass liner containing a stirrer bar was placed Pd(OAc)$_2$ (871 mg, 3.88 mmol), PPh$_3$ (1.96 g, 7.47 mmol, NaOAc (1.48 g, 18.04 mmol) and DMF (82 mL). To this stirred solution was added a solution of R-3-bromo-(1-t- butoxycarbonylamino-2-hydroxyethyl)benzene (4.27 g, 13.5 mmol) in MeOH (82 mL). The resulting solution was purged with nitrogen and placed in a stirred pressure vessel. The system was charged to 4.1 bar (60 psig) of CO and heated at 95° C. for 36 h. The mixture was cooled to room temperature, filtered through diatomaceous earth, and partitioned between ethyl acetate and water. The organic layer was washed with water (3x) and brine (1x) and dried over $MgSO_4$. Removal of solvent under vacuum gave the crude product which was purified by chromatography (silica gel, gradient elution with 30–35% ethyl acetate/hexane) to provide the title product (3.53 g, 89%).

Melting Point=73–75° C. with decomposition.
$^1$H NMR ($CDCl_3$).
API-MS, m/e=240 ($M-C_4H_9+1$).

Intermediate AL-3
R-3-Cyano-(1-t-butoxycarbonylamino-2-hydroxyethyl) benzene.

Prepared from 3-cyanostyrene using Method AL-A. 3-Cyanostyrene was prepared using the method described below.

Melting Point=76° C.
$^1$H NMR ($CDCl_3$).

Preparation of 3-Cyanostyrene.

To a stirred suspension of methyltriphenylphosphonium bromide (75 g, 209.71 mmol) in dry THF (750 mL) at 0° C. under nitrogen was added dropwise n-BuLi (83 mL, 2.5 M in hexanes, 207.50 mmol). The mixture was warmed to room temperature. 3-Cyanobenzaldehyde (25 g, 190.65 mmol) was added as a solid in 5 g batches, and the mixture was stirred at room temperature overnight. The reaction was quenched in water, and the solvent was removed under vacuum. The residue was dissolved in the minimal amount of THF, and triphenylphosphine oxide was precipitated using ether. The solid was filtered through diatomaceous earth, and the filtrate was concentrated. Distillation by Kugelrhor at 90° C./33 Pa (0.25 mm Hg) gave the product as a colorless oil (15.5 g, 62%).

Boiling Point=90° C. at 0.25 mmHg.
$^1$H NMR ($CDCl_3$).

Preparation of Intermediates PAE-1–PAE-18

The following compounds were prepared according to the indicated method (Method PAE-A, Method PAE-B, Method PAE-C, Method PAE-D or PAE-E) from the indicated starting materials, unless otherwise described.

Intermediate PAE-1
Boc-D,L-(2-pyridinyl)glycine Ethyl Ester.

Method PAE-A

To a solution of ethyl hydroxyimino-pyridin-2-yl-acetate (7.8 g, 40.15 g) in ethanol (175 mL) and glacial acetic acid (20 mL) was added 5% Pd/C, and the mixture was shaken in a hydrogenation apparatus under an atmosphere of hydrogen at 4.1 bar (45 psig) for 4 h. The mixture was filtered through diatomaceous earth and concentrated in vacuo. The residue was dissolved in THF/$H_2O$ (1/1, 240 mL) and treated with di-tert-butyl dicarbonate (14.23 g, 65.2 mmol) and sodium bicarbonate (27.4 g, 326 mmol). After stirring at room temperature for 2 h, the solution was concentrated in vacuo and the residue was partitioned between EtOAc and water. The organic phase was washed with brine, dried over magnesium sulfate, filtered and concentrated in vacuo. The crude material was purified via chromatography over silica gel, eluting with a stepwise gradient of 10–20% ethyl acetate in dichloromethane to give 8.11 g (72%) of the title compound as a yellow oil.

1H-NMR
IS-MS, m/e 281.1 (M+1)

Intermediate PAE-2
Boc-D,L-(3-pyridinyl)glycine Ethyl Ester.

Prepared from ethyl hydroxyimino-pyridin-3-ylacetate using Method PAE-A.

1H-NMR
IS-MS, m/e 281.1 (M+1)

Intermediate PAE-3
Boc-D,L-(8-quinolinyl)glycine Ethyl Ester.

Method PAE-B

To a stirring solution of ethyl hydroxyimino-quinolin-8-ylacetate (2.4 g, 9.8 mmol) in 50% aq. formic acid (50 mL) at 0° C. was added zinc dust (2 g, 31 mmol). After 1 min, the mixture was filtered through diatomaceous earth and the filtrate was loaded onto an SCX column. After washing the column with methanol, the product was eluted with a 3 to 1 mixture of dichloromethane and (2 N $NH_3$ in methanol). The product containing fractions were combined and concentrated in vacuo to give 2.24 g of light orange oil (IS-MS, m/e 231.0 (M+1)).

The oil (2.14 g, 9.3 mmol) was dissolved in THF (40 mL) and to this stirring solution was added triethylamine (1.4 mL, 10.2 mmol), followed by di-tert-butyl dicarbonate (2.1 g, 9.8 mmol). After 45 min, the solvent was removed in vacuo and the residue was partitioned between ethyl acetate and water. The organic phase was then washed with satd aq. $NaHCO_3$, dried with $Na_2SO_4$, filtered and concentrated in vacuo. The residue was dissolved in a minimum volume of dichloromethane and chromatographed over silica gel, eluting with 5% ethyl acetate in hexanes. The product containing fractions were combined and concentrated to give 2.5 g (81%) of the title compound.

1H-NMR
IS-MS, m/e 331.0 (M+1)

Intermediate PAE-4
Boc-D,L-(5-quinolinyl)glycine Ethyl Ester

Prepared from ethyl hydroxyimino-quinolin-5-ylacetate using Method PAE-B.

1H-NMR
IS-MS, m/e 331.0 (M+1)

Intermediate PAE-5
N-4-Methoxybenzoyl-N-2,4-dimethoxybenzyl-D,L-(2-trifluoromethylphenyl)glycine Methyl Ester.

Method PAE-C

To 2-trifluoromethylbenzaldehyde (1 g, 5.7 mmol) with stirring was added 2,4-dimethoxybenzylamine (0.86 mL, 5.7 mmol) and methanol (2 mL). After 5 min, the solution was diluted with toluene 100 mL and concentrated in vacuo (twice). The residue was then dissolved in anhydrous methanol (12 mL) and 1,1-dimethyl-2-(methoxycarbonyloxy) ethyl isonitrile [Tetrahedron, 55 (1999) 7411–7420] (0.9 g, 5.7 mmol) was added, followed by 4-methoxybenzoic acid (0.87 g, 5.7 mmol). After stirring for 72 h, the solvent was removed in vacuo and the residue was chromatographed over silica gel, eluting with a step gradient of 30% ethyl acetate in hexanes through 50% ethyl acetate in hexanes. The product containing fractions were combined and concentrated in vacuo; and then the residue was dissolved in ethyl acetate, washed with satd aq. $NaHCO_3$, dried with $Na_2SO_4$, filtered and concentrated to give 1.76 g (48%) of thick oil (NMR, IS-MS, m/e 633.0 (M+1)). The oil (0.5 g, 0.79 mmol) was then dissolved in toluene (5 mL) and concentrated in vacuo (twice) to give a white foam. The residue was then dissolved in THF (3 mL) and potassium tert-butoxide (0.11 g, 0.95 mmol) was added. After 15 min, 12 N HCl (0.079 mL, 0.95 mmol) was added and the solution was allowed to stand overnight in the refrigerator. The next morning, the solvent was removed and the residue was chromatographed over silica gel, eluting with 30% ethyl acetate in hexanes. The product containing fractions were combined and concentrated to give 0.32 g (79%) of the title compound.

1H-NMR

IS-MS, m/e 518.0 (M+1)

Intermediate PAE-6

BOC-D,L-(5-thiazolyl)glycine ethyl ester.

To a r.b. flask (250 cm$^3$), D,L-(5-thiazolyl)glycine ethyl ester (4.60 g, 24.7 mmol) was added to tetrahydrofuran (c.a. 100 cm$^3$) with stirring to give a yellow solution. BOC anhydride (5.439 g, 24.948 mmol) and triethyl amine (3.79 cm$^3$, 2.75 g, 27.17 mmol) were then added with stirring for 1 hour. Reaction monitored by TLC (60% hexane/ethyl acetate; s.m. r.f 0.05, prod. r.f. 0.5.). The reaction concentrated in vacuo and product taken up in ethyl acetate (c.a. 150 cm$^3$), washed with 5% hydrochloric acid solution (ca. 30 cm$^3$), and saturated bicarbonate (ca. 30 cm$^3$). Ethyl acetate layer was dried over magnesium sulphate and evaporated to dryness to give an orange oil (7.42 g, ~24.70 mmol) [~100% Yield].

$^1$H NMR (CDCl$_3$); 1.30 (3H, t), 1.48 (9H, s), 4.28 (2H, q), 5.68 (1H, br.), 7.88 (1H, s), 8.78 (1H, s).

D,L-(5-Thiazolyl)glycine Ethyl Ester.

To a r.b. flask (250 cm$^3$), was added 5-thiazolyloximinoacetic acid ethyl ester (6.37 g, 31.825 mmol) to ethanol (c.a. 80 cm$^3$) with stirring. 50% Formic acid solution (50 cm$^3$) was added with zinc dust (5.10 g, 81.83 mmol) and allowed to stir overnight. Reaction monitored by TLC (60% hexane/ethyl acetate; s.m. r.f 0.3, prod. r.f. 0.05.). Reaction solution filtered over diatomaceous earth and filtrate concentrated in vacuo. This was basified to pH 9 with anhydrous potassium carbonate and product taken up in 3:1 chloroform/isopropanol solution (c.a. 200 cm$^3$). This was washed with saturated bicarbonate (c.a. 50 cm$^3$), dried over magnesium sulphate and concentrated in vacuo to give a brown oil (4.60 g, 24.70 mmol) [78% Yield].

1H NMR (CDCl$_3$); 1.25 (3H, t), 1.95 (2H, br.), 4.22 (2H, q), 4.85 (1H, s), 7.80 (1H, s), 8.70 (1H, s).

Intermediate PAE-7

N-Boc-D,L-(4-thiazolyl)glycine ethyl ester

To a solution of D,L-(4-thiazolyl)glycine ethyl ester (0.460 g, 2.470 mmol) in tetrahydrofuran (20 cm$^3$), was added di-tert-butyl dicarbonate (0.530 g, 2.470 mmol) and triethylamine (0.344 cm$^3$, 2.470 mmol). This was allowed to stir for 1 hour and the solution concentrated in vacuo. The oil was taken up in ethyl acetate (c.a. 50 cm$^3$) washed with 0.5% hydrochloric acid solution (c.a. 20 cm$^3$), and saturated sodium bicarbonate solution (c.a. 20 cm$^3$). This was then dried over magnesium sulphate and concentrated in vacuo to yield an orange oil (0.709 g, 2.477 mmol) [~100% yield].

$^1$H NMR (CDCl$_3$) 1.15 (3H, t), 1.35 (9H, s), 4.1 (2H, m), 5.45 (1H, d), 5.75 (1H, d), 7.3 (1H, d), 8.7 (1H, d).

D,L-(4-Thiazolyl)glycine Ethyl Ester.

This was prepared from ethyl-α-oximino-thiazole-4-acetate (0.60 g) using the method of Hatanaka et al. (*Journal of Medicinal Chemistry*, 1973, 16(9), 978–984) to yield the titled compound (0.46 g).

$^1$H NMR (CDCl$_3$) 1.25 (3H, t), 1.8–2.3 (2H, br.), 4.1 (2H, m), 4.75 (1H, s), 7.25 (1H, d), 8.7 (1H, d).

Intermediate PAE-8

N-Boc-D,L-(2-methylthiazol-4-yl)glycine Ethyl Ester

To a solution of D,L-(2-methylthiazol-4-yl)glycine ethyl ester (0.397 g, 1.982 mmol) in tetrahydrofuran (20 cm$^3$), was added di-tert-butyl dicarbonate (0.475 g, 2.180 mmol) and triethylamine (0.304 cm$^3$, 2.180 mmol). This was allowed to stir for 1 hour and the solution concentrated in vacuo. The oil was taken up in ethyl acetate (c.a. 50 cm$^3$) washed with 0.5% hydrochloric acid solution (c.a. 20 cm$^3$), and saturated sodium bicarbonate solution (c.a. 20 cm$^3$). This was then dried over magnesium sulphate and concentrated in vacuo to yield a yellow oil (0.654 g, 2.177 mmol) [~100% yield].

$^1$H NMR (CDCl$_3$) 1.1 (3H, s), 1.35 (9H, s), 2.6 (3H, s), 4.15 (3H, m), 5.3 (1H, d), 5.7 (1H, s), 7.0 (1H, s).

D,L-(2-Methylthiazol-4-yl)glycine Ethyl Ester.

This was prepared from ethyl-α-oximino-2-methylthiazole-4-acetate (0.62 g) using the method of Hatanaka et al. (*Journal of Medicinal Chemistry*, 1973, 16(9), 978–984) to yield the titled compound (0.40 g).

$^1$H NMR (CDCl$_3$) 1.15 (3H, t), 1.95 (2H, br.), 2.6 (3H, s), 4.15 (2H, m), 4.65 (1H, s), 6.95 (1H, s).

Intermediate PAE-9

Boc-R-(4-Hydroxyphenyl)glycine Methyl Ester

To a stirred mixture of R-(4-hydroxyphenyl)glycine methyl ester hydrochloride (14 g) and sodium bicarbonate (11.7 g) in THF (150 mL) and water (50 mL), was added in one portion, di-t-butyl dicarbonate (15.9 g). The mixture was stirred rapidly to allow thorough mixing for 4 h. Hexane (75 mL) was added and the organic layer separated and washed with satd sodium bicarbonate solution, then brine and then dried with magnesium sulphate. The drying agents was filtered off and washed with a little THF and evaporated to dryness, finishing with a high vacuum pump to remove the last traces of di-t-butyl dicarbonate. Yield 19.7 g, 96%.

$^1$H NMR

R-(4-Hydroxyphenyl)glycine Methyl Ester Hydrochloride.

To a dry 250 mL three necked round bottom flask, equipped with a low temperature thermometer, a septum for nitrogen coverage and another for introduction of thionyl chloride by syringe, was added R-4-hydroxyphenylglycine (12.5 g) and dry methanol (24 mL). The mixture was stirred (magnetic stirrer) and cooled to an internal temperature of −20° C. using cardice/acetone. Using a syringe, thionyl chloride was added dropwise to the cooled mixture over a period of 10 min. (Care: the reaction of thionyl chloride with methanol is very exothermic and rate of addition should be such that the thionyl chloride is efficiently stirred into the mixture and that the temperature does not rise above −20° C. Once the addition was complete the mixture was allowed to warm to room temperature overnight (16–18 h). Dry ether (150 mL) was added and the white ppt. that formed was filtered off, washed with a little more ether and dried. Yield 15.5 g, 95%.

$^1$H NMR

Intermediate PAE-10

Boc-R-(4-Trifluoromethanesulphonyloxyphenyl)glycine Methyl Ester Hydrochloride.

To a stirred solution of Boc-R-(4-hydroxyphenyl)glycine methyl ester (19 g) in dichloromethane (400 mL) was added 2,6-lutidine (9.44 mL) and 4-dimethylaminopyridine (1.65 g) and the mixture cooled in an ice bath. Trifluoromethanesulphonic anhydride (13.74 mL) was added over a period of 5 min, and then the reaction left to warm to room temperature over 4 h. The organic solution was washed with water (2×150 mL), 1 N HCl (2×150 mL), and then saturated sodium bicarbonate (150 mL). The organics were dried with magnesium sulphate and then evaporated to an oil. The mixture was purified using flash chromatography ($SiO_2$ 250 g, eluting with 1:1 hexane/dichloromethane and then neat dichloromethane). Pure product fractions were combined and evaporated, finishing with a high vacuum pump to remove all traces of solvent, to give a white solid, 19 g, 77%.

$^1$H NMR

Intermediate PAE-11

Boc-R-(4-Methoxycarbonylphenyl)glycine Methyl Ester.

Method PAE-D

Boc-R-4-trifluoromethanesulphonyloxyphenylglycine methyl ester (15 g), methanol (32.6 mL), bis-1,3-diphenylphosphinylpropane (448 mg), palladium (II) acetate (255 mg), triethylamine (10.2 mL) and dimethylformamide (72 mL) were placed in the glass liner of pressure (Parr) reactor and the reactor assembled. The vessel was pressurised to ~0.68 bar (10 psig) with nitrogen and the gas released (repeated five times to remove all oxygen from the system). Carbon monoxide gas was then carefully introduced (use extreme care—the gas cylinder is pressurised to far beyond the bursting disc pressure of the Parr, ideally use a pressure regulator to reduce the pressure to ~6.8 bar, 100 psig) to ~1.4 bar (20 psig) and released three times (into the back of a fume hood). Carbon monoxide was then added to ~6.8 bar (100 psig) and the stirrer started. The vessel was slowly heated to 65° C. internal temperature and then stirred at 65° C. overnight. (At the early stages more carbon monoxide was added to maintain ~6.8 bar, 100 psig.) A sample was removed after 18 h and examined by tlc. When complete, the reaction was cooled to ~30° C., the gas released and the vessel flushed five times with nitrogen as before. The reaction mixture was partitioned between ethyl acetate and water, and the organic layer washed with 1 M hydrochloric acid and then saturated sodium bicarbonate. The solution was dried with $MgSO_4$ and evaporated. Flash chromatography of the resulting oil gave the product, pure by tlc, 10.6 g, 90%.

$^1$H NMR

Intermediate PAE-12

Boc-R-(4-Benzyloxycarbonylphenyl)glycine Methyl Ester

Prepared from Boc-R-4-trifluoromethanesulphonyloxy phenylglycine methyl ester and benzyl alcohol using Method PAE-D.

$^1$H NMR

Intermediate PAE-13

Boc-R-(4-Carboxyphenyl)glycine Methyl Ester.

Boc-R-(4-benzyloxycarbonylphenyl)glycine methyl ester (500 mg) was dissolved in THF containing Pd/C 10% (100 mg) and hydrogenated at 1 atm for 2 h. Removal of the catalyst by filtration and evaporation of solvent gave Boc-R-(4-carboxyphenyl)glycine methyl ester (330 mg, 87%).

$^1$H NMR

Intermediate PAE-14

Boc-R-(4-carboxamidophenyl)glycine Methyl Ester.

Method PAE-E

To a solution of Boc-R-(4-carboxyphenyl)glycine methyl ester (3.5 g) in DMF (30 mL) was added EDCI (2.60 g, 1.36 mmol) and HOBt (1.4 g, 10.4 mmol), and the mixture stirred for 10 min before cooling in an ice bath and bubbling in ammonia gas for 5 min. The mixture was stirred for 2 h at room temperature and then diluted with ethyl acetate and washed with water. The aqueous solution was extracted with a little ethyl acetate and the combined organics washed with brine. The organic solution was evaporated to an oil which was purified by flash chromatography ($SiO_2$-dichloromethane/ethyl acetate 0–25%) to give Boc-R-(4-carboxamidophenyl)glycine methyl ester (1.7 g, 48%).

$^1$H NMR

Intermediate PAE-15

Boc-R-(4-methylcarboxamidophenyl)glycine Methyl Ester.

Prepared from Boc-R-(4-carboxyphenyl)glycine methyl ester and methylamine using Method PAE-E.

$^1$H NMR

Intermediate PAE-16

N-4-Methoxybenzoyl-N-2,4-dimethoxybenzyl-D,L-(quinolin-4-yl)glycine Methyl Ester.

Prepared from quinoline-4-carboxaldehyde using Method PAE-C.

$^1$H NMR

Intermediate PAE-17

Ethyl Boc-D,L-thiazol-2-ylglycine.

Prepared from ethyl hydroxyimino-thiazol-2-ylacetate using Method PAE-B. In this case, reaction with Zn/formic acid was conducted over 15 min.

$^1$NMR

IS-MS, m/e 287.0 (M+1)

Intermediate PAE-18

Ethyl Boc-D,L-isoquinolin-8-ylglycine.

Prepared from ethyl hydroxyimino-isoquinolin-8-ylacetate using Method PAE-B. In this case, reaction with Zn/formic acid was conducted over 30 min, followed by concentration and partitioning of the residue between 3/1 chloroform/isopropanol and satd aq. $NaHCO_3$. The Boc protection was carried out as previously described. Purification was performed using silica gel chromatography (Biotage Quad System) eluting with 10% ethyl acetate in methylene chloride.

$^1$NMR

IS-MS, m/e 331.0 (M+1)

Analysis for $C_{18}H_{22}N_2O_4$:

Calcd: C, 65.44; H, 6.71; N, 8.48;
Found: C, 65.05; H, 6.67; N, 8.49.

Preparation of Intermediates PAA-1–PAA-28

The following compounds were prepared according to the indicated method (Method PAA-A, Method PAA-B, Method PAA-C, Method PAA-D, Method PAA-E or Method PAA-F) from the indicated starting materials, unless otherwise described.

Intermediate PAA-1

Boc-D,L-(2-chlorophenyl)glycine.

Method PAA-A

2-Chlorobenzaldehyde (20 mmol, 2.252 mL) and 2,4-dimethoxybenzylamine (20 mmol, 3.004 mL) were added together and stirred for 2 hours. DCM (5 mL) was added and any water separated and removed. tert-Butyl isonitrile (20 mmol, 2.262 mL) was added and stirred for 10 min, followed by acetic acid (20 mmol, 1.145 mL). Stirring was continued for 3 days. The reaction mixture was then treated with TFA (30 mL) and triethylsilane (5 mL). After 3 h the mixture was evaporated to dryness, 6 M HCl (100 mL) added, and the whole refluxed overnight at 130° C., stirring rapidly. The mixture was allowed to cool and extracted with EtOAc (50 mL×2); the aqueous fraction was evaporated to dryness and treated with 2 M NaOH solution. The mixture was extracted with EtOAc (50 mL×2); excess boa anhydride (5.2 g) in dioxane (20 mL) was added to the aqueous fraction and stirred overnight. The mixture was extracted with diethyl ether (100 mL×2), acidified to pH 1 (conc HCl) and extracted with EtOAc (50 mL×2). The combined organic fractions were washed with water and evaporated to dryness under high vacuum. The product Boc-2-chlorophenylglycine (4.252 g, 74.5%)

$^1$H NMR (CD$_3$CN/D$_2$O) 7.3 (4H, m); 5.5 (1H, s); 1.3 (9H, s). MS 286 (M+1)

Intermediate PAA-1'
(R)-Benzyloxycarbonyl-(2-chlorophenyl)glycine.
Prepared from 2-chlorostyrene using the method of Sharpless et al J.A.C.S. (1998) Vol120 No.6 1207–1217.

Intermediate PAA-1, alternative preparation
Boc-D,L-(2-chlorophenyl)glycine.
Prepared from 2-chlorobenzaldehyde using method PAA-F. In this case, the reaction temperature was not controlled upon addition of 2-chlorobenzaldehyde and the reaction was allowed to stir for 2 h. Extraction of the intermediate aminonitrile was performed with ethyl ether in place of ethyl acetate and was further purified by addition of HCl gas to the ethereal extracts followed by decantation of the mother liquor to isolate the semisolid hydrochloride salt. BOC protection of the amino acid was performed from 0° C. to room temperature over a period of one hour and the final extraction was performed with ethyl acetate in place of ethyl ether.

$^1$H-NMR
IS-MS m/e 284 (M−1)

Intermediate PAA-2
Boc-D,L-(3-fluorophenyl)glycine.
Prepared from 3-fluorobenzaldehyde using method PAA-A.
$^1$H NMR (CD$_3$CN/D$_2$O) 7.3 (1H, m), 7.1(3H, m); 5.2 (1H, s); 1.3 (9H, s). MS 270 (M+1)

Intermediate PAA-3
Boc-D,L-(4-fluorophenyl)glycine.
Prepared from 4-fluorobenzaldehyde using Method PAA-A.
$^1$H NMR (CD$_3$CN/D$_2$O) 7.3 (2H, m); 6.9 (2H, m), 5.0 (1H, s); 1.3 (9H, s). MS 270 (M+1)

Intermediate PAA-4
Boc-D,L-(2-methylphenyl)glycine.
Prepared from 2-methylbenzaldehyde using Method PAA-A.
$^1$H NMR (CD$_3$CN/D$_2$O) 7.3 (4H, m); 5.5 (1H, s); 2.5 (3H, s); 1.3 (9H, s). MS 266 (M+1)

Intermediate PAA-5
Boc-D,L-(3-thienyl)glycine.
Prepared from 3-thiophenecarboxaldehyde using Method PAA-A.
$^1$H NMR (CD$_3$CN/D$_2$O) 7.5 (2H, m); 7.1 (1H, d); 5.3 (1H, s); 1.3 (9H, s). MS 258 (M+1)

Intermediate PAA-6
Boc-D,L-(2-fluorophenyl)glycine.
Was obtained by treating D,L-2-fluorophenylglycine (Aldrich) with Boc anhydride (1.1 eq) and 2 M NaOH (1 eq) in ethanol. Aqueous work up as described above yielded the protected amino acid.
$^1$H NMR Intermediate PAA-7
Boc-D,L-(2-methoxyphenyl)glycine.
Prepared from 2-methoxybenzaldehyde using Method PAA-A.
$^1$H NMR Intermediate PAA-7, alternative preparation
Boc-D,L-(2-methoxyphenyl)glycine.
Prepared from 2-methoxybenzaldehyde using method PAA-F. In this case, the reaction was cooled to 0° C. before addition of 2-methoxybenzaldehyde and was then allowed to stir at room temperature overnight. Extraction of the intermediate aminonitrile was performed with ethyl ether in place of ethyl acetate and was further purified by addition of 1 M HCl in ethyl ether followed by filtration of the crystalline hydrochloride salt. BOC protection of the amino acid was performed from 0° C. to room temperature over a period of three hours, and the final extraction was performed with dichloromethane in place of ethyl ether.

$^1$H-NMR
IS-MS m/e 280.1 (M−1)

| Analysis for C$_{14}$H$_{19}$NO$_5$ |
|---|
| Calcd: C, 59.78; H, 6.81; N, 4.98; |
| Found: C, 59.68; H, 6.78; N, 4.95. |

Intermediate PAA-8
Boc-D,L-(2-trifluoromethyl)phenylglycine.
Prepared from 2-trifluoromethylbenzaldehyde using Method PAA-A.
$^1$H NMR Intermediate PAA-8, alternative preparation
Boc-D,L-(2-trifluoromethylphenyl)glycine.
Prepared from 2-trifluoromethylbenzaldehyde using method PAA-F. In this case, the reaction temperature was not controlled upon addition of 2-trifluoromethylbenzaldehyde and the reaction was allowed to stir for 2 h. Extraction of the intermediate aminonitrile was performed with ethyl ether in place of ethyl acetate and was further purified by addition of HCl gas to the ethereal extracts followed by decantation of the mother liquor to isolate the semisolid hydrochloride salt. BOC protection of the amino acid was performed from 0° C. to room temperature over a period of one hour and the final extraction was performed with ethyl acetate in place of ethyl ether.

$^1$H-NMR
IS-MS m/e 318 (M−1)

Intermediate PAA-9
Boc-D,L-(8-quinolinyl)glycine.

Method PAA-B

To a stirring solution of Boc-D,L-(8-quinolinyl)glycine ethyl ester (2.29 g, 6.93 mmol) in 1,4-dioxane (11 mL) was added a solution of LiOH hydrate (0.32 g, 7.6 mmol) in water. After 2 h, the solvents were removed in vacuo and the residue was dissolved in water and washed with diethyl ether. The aqueous phase was then acidified to pH 3 with solid citric acid and extracted with ethyl acetate. The organic phase was then washed with brine, dried with Na$_2$SO$_4$, filtered and concentrated to give 2.06 g (98%) of the title compound.

1H-NMR
IS-MS, m/e 303.0 (M+1)

Intermediate PAA-10
Boc-D,L-(S-quinolinyl)glycine.
Prepared from Boc-D,L-(5-quinolinyl)glycine ethyl ester using Method PAA-B.
1H-NMR
IS-MS, m/e 303.0 (M+1)

Intermediate PAA-11

Boc-D-(3-bromophenyl)glycine.

Prepared from R-3-bromo-(1-t-butoxycarbonylamino-2-hydroxyethyl)benzene using Method PAA-C.

Melting Point=130–132° C. with decomposition

1H NMR (CDCl$_3$)

API-MS, m/e=286 (M−CO$_2$H+1)

Intermediate PAA-12

Boc-D-(3-methoxycarbonylphenyl)glycine.

Method PAA-C

To a stirred solution of R-3-methoxycarbonyl-(1-t-butoxycarbonylamino-2-hydroxyethyl)benzene (338 mg, 1.14 mmol) in acetone (7.2 mL) was added 5% NaHCO$_3$ (3 mL). The reaction mixture was cooled to 0° C. To the stirred suspension was added KBr (14 mg, 0.12 mmol), TEMPO (181 mg, 1.16 mmol) and NaOCl dropwise (2.81 mL, 5.25%). After 1 h at 0° C., TEMPO (136 mg, 0.88 mmol) and NaOCl (1.09 mL; 5.25%) were added. The reaction was stirred for a further 0.5 h at 0° C. and 5% NaHCO$_3$ (4.3 ml) was added. The reaction was allowed to warm to room temperature overnight. Acetone was removed under vacuum and the crude product was partitioned between ethyl acetate and water. The aqueous layer was washed with ethyl acetate (2×) and acidified to pH 5 with 10% citric acid and extracted with ethyl acetate (4×). The combined organic extracts were dried over MgSO$_4$. Removal of solvent under vacuum gave the product (305 mg, 86%).

$^1$H NMR (CDCl$_3$)

API-MS, m/e=254 (M−C$_4$H$_9$+1)

Intermediate PAA-13

Boc-D-(3-cyanophenyl)glycine.

Prepared from R-3-cyano-(1-t-butoxycarbonylamino-2-hydroxyethyl)benzene using Method PAA-C.

$^1$H NMR (CDCl$_3$)

API-MS, m/e=221 (M−C$_4$H$_9$+1)

Intermediate PAA-14

Boc-D-(3-ethanesulfonylaminophenyl)glycine.

To a stirring solution of 3-(ethanesulfonylaminophenyl)glycine (20 g, 77.43 mmol) and sodium carbonate (8.2 g, 77.43 mmol) in 3:1 THF:water (200 mL) at 0° C., was added di-tert-butyl dicarbonate (18.5 g, 85.17 mmol). After stirring for 30 min, the cold bath was removed; and after an additional 30 min at room temperature the solvent was removed; and the residue was partitioned between ethyl acetate and water. The aqueous layer was acidified to pH 2 with KHSO$_4$ and extracted twice with ethyl acetate. The combined ethyl acetate extracts were washed with water, dried with Na$_2$SO$_4$, filtered and concentrated in vacuo to give 17.51 g (63%) of a white solid.

1H-NMR

IS-MS, m/e 357.0 (M−1)

Intermediate PAA-15

N-Boc-D,L-(5-thiazolyl)glycine.

To a r.b. flask (150 cm$^3$), was added Boc-D,L-(5-thiazolyl)glycine ethyl ester (7.00 g, 24.70 mmol) to ethanol (c.a. 100 cm$^3$) with stirring. 2 M Sodium hydroxide solution (25 cm$^3$, 50 mmol) was added and allowed to stir for 1 h. Reaction monitored by TLC (60% hexane/ethyl acetate; s.m. r.f 0.5, prod. r.f. 0.). Reaction concentrated in vacuo and product taken up in saturated bicarbonate (c.a. 50 cm$^3$) and washed with ethyl acetate (c.a. 30 cm$^3$). Aqueous layer was acidified to pH 2 with concentrated hydrochloric acid and product extracted with 3:1 chloroform/isopropanol solution (c.a. 3×60 cm$^3$). The organic layer was dried over magnesium sulphate and evaporated to dryness to give an orange solid (4.47 g, 17.30 mmol) [74% Yield].

$^1$H NMR (CDCl$_3$); 1.35 (9H, s) , 5.60 (1H, d), 5.83 (1H, d), 7.88 (1H, s), 8.80 (1H, s).

Intermediate PAA-16

N-Boc-D,L-(4-thiazolyl)glycine.

Method PAA-D

To a solution of N-Boc-D,L-(4-thiazolyl)glycine ethyl ester (0.700 g, 2.470 mmol) in methanol (c.a. 15 cm$^3$), was added 2 M sodium hydroxide (2.47 cm$^3$, 4.940 mmol) and allowed to stir for 90 min. The solution was concentrated in vacuo and taken up in water (c.a. 20 cm$^3$). The aqueous solution was washed with ethyl acetate (c.a. 20 cm$^3$), and then acidified to pH 2 with 5% hydrochloric acid solution (c.a. 50 cm$^3$). The product was extracted with ethyl acetate (c.a. 3×30 cm$^3$), dried over magnesium sulphate, and concentrated in vacuo to yield a pale yellow oil (0.582 g, 2.254 mmol) [91% yield].

$^1$H NMR (CDCl$_3$) 1.35 (9H, s), 5.5 (1H, d), 5.8 (1H, d), 7.35 (1H, d), 8.75 (1H, d), 9.8–10.2 (1H, br.).

Intermediate PAA-17

N-Boc-D,L-(2-methylthiazol-4-yl)glycine.

Prepared from N-Boc-D,L-(2-methylthiazol-4-yl)glycine ethyl ester using Method PAA-D.

$^1$H NMR (CDCl$_3$) 1.35 (9H, s), 2.6 (3H, s), 5.4 (1H, d), 5.9 (1H, s) , 7.1 (1H, s).

Intermediate PAA-18

N-Boc-D,L-(2-Benzyloxycarbonylamino-4-thiazolyl) glycine.

Is prepared from D,L-(2-benzyloxycarbonylamino-4-thiazolyl)glycine. The benzyloxycarbonyl protecting group is removed from the thiazolyl amino group at a convenient point in the preparation of a final compound using a conventional method, such as, for example, heating a solution of an intermediate in HBr/acetic acid at 60° C., followed by evaporation and a conventional isolation, such as by using SCX ion exchange chromatography.

D,L-(2-Benzyloxycarbonylamino-4-thiazolyl)glycine.

Was prepared by the method of Hardy, K.; Harrington, F. and Stachulski, A.—J. Chem. Soc. Perkin Trans I (1984) 1227–1235.

Intermediate PAA-19

Boc-R-(4-ethoxycarbonylphenyl)glycine.

To a solution of Boc-R-(4-methoxycarbonylphenyl)glycine methyl ester (692 mg) in THF (10 mL) was added a solution of lithium hydroxide hydrate (90 mg) in water (7 mL). The mixture immediately became cloudy and over 15 min cleared. After 30 min, tic showed the reaction to be complete. Ethyl acetate (20 mL) and water (20 mL) were added, and the aqueous layer separated. The aqueous solution was acidified with 2 M hydrochloric acid and extracted with ethyl acetate (3×20 mL). The organic solution was then washed with water×2 and brine×2, dried with MgSO$_4$ and evaporated to give the mono-ester (650 mg, 98%), pure by tlc.

$^1$H NMR

Intermediate PAA-20

Boc-R-(4-Methoxyphenyl)glycine.

Boc-R-(4-hydroxyphenyl)glycine methyl ester was converted to Boc-R-4-methoxyphenylglycine using the alkylation method described by Basak et al. (Tetrahedron Lett. 1998, 39 (27), 4883–4886), followed by hydrolysis of the methyl ester with lithium hydroxide in aqueous THF.

$^1$H NMR

Intermediate PAA-21

N-4-Methoxybenzoyl-N-2,4-dimethoxybenzyl-D,L-(2-trifluoromethylphenyl)glycine.

Prepared from N-4-methoxybenzoyl-N-2,4-dimethoxybenzyl-D,L-(2-trifluoromethylphenyl)glycine methyl ester using Method PAA-B (3 equivalents of LiOH hydrate).

¹H NMR
IS-MS, m/e 503.9 (m+1)
Intermediate PAA-22
N-4-Methoxybenzoyl-N-2,4-dimethoxybenzyl-D,L-(thien-2-yl)-glycine.

Method PAA-E

To a solution of 2-thiopheneboronic acid (5.0 g, 39.0 mmol, 1 equiv) in 275 mL of methylene chloride at rt was added 3,4-dimethoxybenzylamine (5.89 mL, 39.0 mmol, 1 equiv) followed by glyoxylic acid monohydrate 3.6 g, 39 mmol, 1 equiv). The reaction was allowed to stir for 56 hours at rt after which time the resultant precipitate was filtered and washed with methylene chloride to afford 9.3 g (78%) of N-2,4-dimethoxybenzyl-D,L-(thien-2-yl)glycine as an off-white solid (IS-MS, m/e 308 (m+1)).

A portion of the solid (5.0 g, 16.3 mmol, 1 equiv.) was dissolved in acetone (20 mL) and 1 N sodium hydroxide (20 mL) at rt. To this solution was simultaneously added anisoyl chloride (2.78 g, 16.3 mmol, 1 equiv.) in 20 mL of acetone and 2 N sodium hydroxide in dropwise fashion. After stirring at rt for 1 h, the reaction was cooled to 0° C. and was acidified to pH 2–3. Diethyl ether was added and the product was extracted into the organic phase. The combined organic phases were washed with brine, dried over sodium sulfate, filtered, and concentrated to afford 5.1 g (71%) of the titled compound as a white solid.

IS-MS, m/e 440 (m+1).
Intermediate PAA-23
N-Boc-N-2,4-dimethoxybenzyl-D,L-(thien-2-yl)glycine.

To solution of N-2,4-dimethoxybenzyl-D,L-(thien-2-yl) glycine (1.0 g, 3.2 mmol, 1 equiv) in 6 mL of acetone and 6 mL of water at rt was added triethylamine (0.97 mL, 7.0 mmol, 2.1 equiv.) followed by addition of 2-(tert-butoxycarbonyloxyimino)-2-phenylacetonitrile (BOC-ON) (0.76 g, 3.1 mmol, 0.95 equiv). After stirring at rt overnight, the reaction was diluted with water and washed with ether. The aqueous phase was then acidified with 0.5 M citric acid and the product was extracted into diethyl ether. The combined organic phases were washed with brine, dried over sodium sulfate, filtered, and concentrated to afford 0.38 g (29%) of the titled compound as a crude yellow oil.

IS-MS, m/e 408 (m+1).
Intermediate PAA-24
Boc-D,L-isoquinolin-8-ylglycine.

Prepared from ethyl Boc-D,L-isoquinolin-8-ylglycine using Method PAA-B. The product was precipitated from a basic aqueous solution by adjusting the pH to 3 with solid citric acid.
¹NMR
IS-MS, m/e 303.0 (M+1)

| Analysis for $C_{16}H_{18}N_2O_4 \cdot 0.5\ H_2O$: |
| --- |
| Calcd: C, 61.73; H, 6.15; N, 9.00; |
| Found: C, 61.62; H, 5.66; N, 8.84. |

Intermediate PAA-25
Boc-D,L-Naphthalen-1-ylglycine.

Method PAA-F
Part A: D,L-Naphthalen-1-ylglycine Hydrochloride.

To a solution of sodium cyanide (10.0 g, 0.22 mmol) in 40 mL of water was added ammonium chloride (11.4 g, 0.22 mmol), and the mixture was stirred until dissolution was complete. A solution of 1-naphthaldehyde (31.0 g, 0.22 mmol) in 40 mL of methanol was then added and the resultant mixture was allowed to stir at room temperature for two days. An additional 150 mL of water was then added and the crude product was extracted into EtOAc. The combined organic layers were washed with water, dried over Na₂SO₄, filtered and concentrated to afford a crude oil. The crude residue was chromatographed over silica gel, eluting with with 10:1 EtOAc:CH₂Cl₂, to give 35 g of a light brown oil. This material was then dissolved in 250 mL of 5 N HCl and was heated to reflux for 9 h. The reaction was allowed to cool to room temperature and the product was allowed to crystallize overnight. Filtration of the mixture afforded 13.6 g (29%) of the title compound as light brown crystals.
¹NMR
IS-MS, m/e 201.9 (M+1)
Part B: Boc-D,L-Naphthalen-1-ylglycine.

To a solution of D,L-naphthalen-1-ylglycine hydrochloride (13.6 g, 57.2 mmol) and 2 N sodium hydroxide (57 mL, 115 mmol) in 120 mL of 1,4-dioxane and 60 mL of water was added (Boc)₂O (15 g, 69 mmol). The reaction was allowed to stir at room temperature for 3 h after which time the solution was brought to pH 5 by addition of 1 N sulfuric acid. The product was then extracted into EtOAc; and the combined organic extracts were dried over Na₂SO₄, filtered, and concentrated to give 14 g (81%) of the title compound as a light brown foam.
¹NMR
IS-MS, m/e 300.1 (M–1)
Intermediate PAA-26
Boc-D,L-(2-methylthiophenyl)glycine.

To a solution of 2-(methylthio)benzaldehyde (15 g, 98.7 mmol) in 100 mL of ethanol was added ammonium carbonate (23.1 g, 296 mmol) and a solution of potassium cyanide (12 g, 148 mmol) in 100 mL water. The reaction was heated and stirred at 70° C. for 3 h after which time the reaction was concentrated under reduced pressure. The product was extracted into ethyl acetate; and the combined organic phases were washed with brine, dried over Na₂SO₄, filtered and concentrated. The resultant crude residue was taken up in 70 mL of ethyl acetate, and 70 mL of 5 N sodium hydroxide was added. The reaction was heated to reflux for three days after which time the ethyl acetate was removed under reduced pressure. To the aqueous mixture was sequentially added 100 mL of dioxane, Boc₂O (42 g, 192 mmol), and 100 mL of 2.5 N sodium hydroxide.

The reaction was then heated at reflux for 48 h. After cooling to room temperature, the reaction was diluted with water and the aqueous phase was washed with ethyl ether. The aqueous layer was then acidified to pH 2 and the product was extracted into ethyl acetate. The combined organic extracts were washed with brine, dried over MgSO₄, filtered, and concentrated to afford 21.7 g of a crude residue. Purification by silica gel chromatography (gradient elution, 97:2:1 to 95:4:1 dichloromethane:methanol:acetic acid) provided 5.0 g (17%) of the title compound.
¹H-NMR
ES-MS m/e 296 (M–1)
Intermediate PAA-27
Boc-D,L-(2-methylsulfonylphenyl)glycine.

To a solution of boc-D,L-(2-methylthiophenyl)glycine (4.5 g, 15.2 mmol) in 75 mL of methanol was added a solution of oxone (14 g, 23 mmol) in water. The reaction was stirred at room temperature for 2 h after which time the methanol was removed under reduced pressure. The product was extracted into ethyl acetate and the combined organic layers were washed with brine, dried over MgSO₄, filtered, and concentrated to afford 4.35 g (87%) of the title compound.

¹H-NMR

ES-MS m/e 230(M+1−C₅H₉O₂)

Intermediate PAA-28

Boc-D,L-(benzo[b]thiophen-3-yl)glycine.

May be prepared by the method of Kukolja, S. et al. *J. Med. Chem.* 1985, 28, 1886–1896.

General Experimental Procedures: Synthesis of Inhibitors

Method 1: Using a solid phase strategy on a Protein Technologies, Symphony Multiple Peptide Synthesiser by attachment of bis amino compounds to Peg-trityl chloride resin: Trityl chloride resin was typically treated with greater than 2 fold excess of the di-amine in dry DCM. The resin was further modified by the attachment of acids. Activation of Fmoc protected amino acid (2–5 eq) was by TBTU/DIPEA, all couplings (minimum 120 min.) were carried out in DMF. Deprotection of the Fmoc group was achieved with 20% piperidine in DMF. In the next stage other acid substituents were added as the HOBt or HOAt esters either by activation with HBTU/HATU or HATU/EDCI with or without Boc protection of amino groups. Cleavage of the products from the resin was by treatment (30 min, ambient) with 10% triethylsilane in TFA was followed by filtration, evaporation and trituration with diethyl ether.

Synthesis using the Symphony Multiple Peptide Synthesiser.

The Symphony Multiple Peptide Synthesiser is charged with DMF, DCM, TBTU in DMF (450 mM), DIPEA in DMF (900 mM), 20% piperidine in DMF. Resins are held in plastic reaction vessels that allow the introduction of reagents and solvents and nitrogen for agitation or air drying.

A typical synthesis cycle on the Symphony is as follows:

The reaction vessel containing the resin (0.1 mmol) is charged with the Fmoc protected amino acid (0.5 mmol); and then this is dissolved in DMF (2.5 mL), treated with TBTU (0.56 mmol, 1.25 mL) and DIPEA (1.1 mmol, 1.25 mL) and agitated with nitrogen for 2 hours (agitation times may vary). After coupling, the resin is washed with DMF (6×5 mL), then deprotected with 20% piperidine in DMF (2×5 mL for 1 min each, then 1×5 mL for 8 min); the resin is then washed with DMF (6×5 mL).

PREPARATION OF EXAMPLES 1–11

Preparation of Starting Materials

4-Methoxybenzoyl-D-phenylglycinyl-R,S-3-hydroxypyrrolidine.

D-Phenylglycinyl-R,S-3-hydroxypyrrolidine (3.42 g, 15.5 mmol) was dissolved in dichloromethane (100 mL) and placed under argon. Triethylamine (2.27 mL, 16.28 mmol) was added followed by 4-methoxybenzoyl chloride (2.78 g, 16.3 mmol) and the mixture stirred at room temperature for 3.5 h. The organic solution was washed with 0.5% hydrochloric acid (50 mL), satd sodium bicarbonate solution (50 mL) and brine (50 mL). The organic solution was dried (MgSO₄) and evaporated to an off-white solid, 4-methoxybenzoyl-D-phenylglycinyl-R,S-3-hydroxypyrrolidine, (5.49 g, 100%).

Hplc (Luna C18, Gradient 3, water/acetonitrile/TFA), rt, 11.7 min

LCMS M+1 355

¹NMR

4-Methoxybenzoyl-D-phenylglycinyl-4-hydroxypiperidine.

By a similar method to that above D-phenylglycinyl-4-hydroxypiperidine was converted to 4-methoxybenzoyl-D-phenylglycinyl-4-hydroxypiperidine.

Hplc (Luna C18, Gradient 3, water/acetonitrile/TFA), rt, 11.9 min

LCMS M+1 369

¹NMR

Example 1

1-(4-Methoxybenzoyl-D-phenylglycinyl)-3-(R,S)-(2-fluorophenoxy)pyrrolidine.

To a solution of 4-methoxybenzoyl-D-phenylglycinyl-R,S-3-hydroxypyrrolidine (400 mg, 1.13 mmol) in benzene (10 mL) at 10° C. was added 2-triphenylphosphonium 4,4-dimethyltetrahydro-1,2,5-thiadiazolidine 1,1-dioxide Reference: J. Castro et al., J. Org. Chem. 1994, 59, 2289–2291 (696 mg, 1.69 mmol) and 3-methoxyphenol (210 mg) and the mixture allowed to warm to room temperature overnight. The reaction mixture was diluted with ether (30 mL) and washed with dilute sodium bicarbonate solution. The organic solution was dried (MgSO₄) and concentrated. The residue was purified by by reverse phase preparative chromatography to give 1-(4-methoxybenzoyl-D-phenylglycinyl)-3-(R,S)-(3-methoxyphenoxy)pyrrolidine.

Hplc (Luna C18, Gradient 3, water/acetonitrile/TFA), rt, 11.75 min.

LCMS M+1 461

¹NMR (mixture of diastereomers).

Examples 2–10 were prepared according to the method of Example 1 using the indicated reagents:

Example 2

1-(4-Methoxybenzoyl-D-phenylglycinyl)-3-(R,S)-(3-methoxyphenoxy)pyrrolidine.

From 4-methoxybenzoyl-D-phenylglycinyl-R,S-3-hydroxypyrrolidine and 3-methoxyphenol:

Hplc (Luna C18, Gradient 3, water/acetonitrile/TFA), rt, 11.75 min.

LCMS M+1 461

¹NMR (mixture of diastereomers).

Example 3

1-(4-Methoxybenzoyl-D-phenylglycinyl)-4-(3-methoxyphenoxy)piperidine.

From 4-methoxybenzoyl-D-phenylglycinyl-4-hydroxypiperidine and 3-methoxyphenol:

Hplc (Luna C18, Gradient 3, water/acetonitrile/TFA), rt, 16.09 min

LCMS M+1 475

¹NMR

Example 4

1-(4-Methoxybenzoyl-D-phenylglycinyl)-4-(4-methoxyphenoxy)piperidine.

From 4-methoxybenzoyl-D-phenylglycinyl-4-hydroxypiperidine and 4-methoxyphenol:

Hplc (Luna C18, Gradient 3, water/acetonitrile/TFA), rt, 15.8 min.

LCMS M+1 475

¹NMR

Example 5

1-(4-Methoxybenzoyl-D-phenylglycinyl)-4-(3-fluorophenoxy)piperidine.

From 4-methoxybenzoyl-D-phenylglycinyl-4-hydroxypiperidine and 3-fluorophenol:

Hplc (Luna C18, Gradient 3, water/acetonitrile/TFA), rt, 12.75 min.

LCMS M+1 463

¹NMR

Example 6
1-(4-Methoxybenzoyl-D-phenylglycinyl)-4-(2-methanesulfonylphenoxy)piperidine.

From 4-methoxybenzoyl-D-phenylglycinyl-4-hydroxypiperidine and 2-methanesulphonylphenol:

Hplc (Luna C18, Gradient 3, water/acetonitrile/TFA), rt, 10.8 min.
LCMS M+1 523
$^1$NMR

Example 7
1-(4-Methoxybenzoyl-D-phenylglycinyl)-4-(2-methylmercaptophenoxy)piperidine.

From 4-methoxybenzoyl-D-phenylglycinyl-4-hydroxypiperidine and 2-methylmercaptophenol:

Hplc (Luna C18, Gradient 3, water/acetonitrile/TFA), rt, 12.7 min
LCMS M+1 491
$^1$NMR

Example 8
1-(4-Methoxybenzoyl-D-phenylglycinyl)-4-(2-fluorophenoxy)piperidine.

From 4-methoxybenzoyl-D-phenylglycinyl-4-hydroxypiperidine and 2-fluorophenol:

Hplc (Luna C18, Gradient 3, water/acetonitrile/TFA), rt, 15.8 min.
LCMS M+1 463
$^1$NMR

Example 9
1-(4-Methoxybenzoyl-D-phenylglycinyl)-4-(phenoxy)piperidine.

From 4-methoxybenzoyl-D-phenylglycinyl-4-hydroxypiperidine and phenol:

Hplc (Luna C18, Gradient 3, water/acetonitrile/TFA), rt, 16.8 min.
LCMS M+1 445

Example 10
1-(4-Methoxybenzoyl-D-phenylglycinyl)-4-(3-pyridoxy)piperidine.

From 4-methoxybenzoyl-D-phenylglycinyl-4-hydroxypiperidine and 3-hydroxypyridine:

Hplc (Luna C18, Gradient 3, water/acetonitrile/TFA), rt, 11.4 min
LCMS M+1 446
$^1$NMR

Example 11
1-(4-Methoxybenzoyl-D-phenylglycinyl)-4-(4-fluorophenoxy)piperidine.

To a solution of triphenylphosphine (285 mg, 1.09 mmol) in dry THF (5 mL) under argon at −15° C. was added slowly (below −10° C.) diethyl azodicarboxylate (DEAD) (208 mg, 1.19 mmol) and the solution stirred at less than −10° C. for 5 min. To this mixture was added a solution of 4-methoxybenzoyl-D-phenylglycinyl-4-hydroxypiperidine (400 mg, 1.08 mmol) and 4-fluorophenol (122 mg, 1.09 mmol) in dry THF (5 mL) over 5 min at less than −10° C. The reaction was warmed to room temperature and monitored by tlc (SiO$_2$—ethyl acetate). The reaction mixture was poured into water (5 mL) and extracted with dichloromethane (100 mL). The organic solution was washed with satd sodium bicarbonate (50 mL) and 0.5% hydrochloric acid (50 mL), dried (MgSO$_4$) and concentrated and the residue purified by flash chromatography, (SiO$_2$—30% ethyl acetate in hexane) to give 1-(4-methoxybenzoyl-D-phenylglycinyl)-4-(4-fluorophenoxy)piperidine (107 mg, 21%).

Hplc (Luna C18, Gradient 3, water/acetonitrile/TFA), rt, 16.0 min
LCMS M+1 463
$^1$NMR Preparation of Starting Materials of Formula (10) in Which Q is —O—:
Benzyloxycarbonyl-D-phenylglycinyl-R,S-3-hydroxypyrrolidine.

Benzyloxycarbonyl-D-phenylglycine (18.01 g, 63.1 mmol) and R,S-3-hydroxypyrrolidinol (5.0 g, 57.4 mmol) were suspended in dimethylformamide (300 mL). HOAt (8.61 g, 63.1 mmol) was added, the mixture stirred for 3 min, and then EDCI (12.1 g 63.1 mmol) was added with stirring and the mixture left overnight. The orange solution was concentrated in vacuo and the residue taken up in ethyl acetate (300 mL). The organic solution was washed with satd sodium bicarbonate (2×100 mL), 0.5% aqueous hydrochloric acid (50 mL) and brine (100 mL).

The organic solution was dried (MgSO$_4$) and evaporated in vacuo to give an orange solid. Flash chromatography (SiO$_2$ 1:1 dichloromethane:ethyl) acetate gave benzyloxycarbonyl-D-phenylglycinyl-R,S-3-hydroxypyrrolidine (11.4 g, 56%).

Hplc (Luna C18, Gradient 3, water/acetonitrile/TFA), rt, 12.7 min
LCMS M+1 355
$^1$NMR Benzyloxycarbonyl-D-phenylglycinyl-4-hydroxypiperidine.

By a similar method using benzyloxycarbonyl-D-phenylglycine and 4-hydroxypiperidine, benzyloxycarbonyl-D-phenylglycinyl-4-hydroxypiperidine was prepared.

Hplc (Luna C18, Gradient 3, water/acetonitrile/TFA), rt, 11.9 min
LCMS M+1 369
$^1$NMR D-Phenylglycinyl-R,S-3-hydroxypyrrolidine.

Benzyloxycarbonyl-D-phenylglycinyl-R,S-3-hydroxypyrrolidine, (5.49 g, 15.5 mmol) was dissolved in ethanol (120 mL) and Pd/C (10%, 100 mg) added. The mixture was hydrogenated at atmospheric pressure until complete by tlc (SiO$_2$ ethyl acetate—starting material Rf. 0.6, product 0.05). The catalyst was filtered using diatomaceous earth; and the resulting solution concentrated in vacuo to give D-phenylglycinyl-R,S-3-hydroxypyrrolidine as a yellow oil (3.54 g, 16.1 mmol).

D-Phenylglycinyl-4-hydroxypiperidine.

By a similar method benzyloxycarbonyl-D-phenylglycinyl-4-hydroxypiperidine was converted to D-phenylglycinyl-4-hydroxypiperidine.

Benzyloxycarbonyl-D-phenylglycinyl-4-(3-pyridoxy)piperidine.

To a solution of benzyloxycarbonyl-D-phenylglycinyl-4-hydroxypiperidine (500 mg, 1.36 mmol), 3-hydroxypyridine (129 mg, 1.36 mmol) and triphenylphosphine (356 mg, 1.36 mmol) in dry THF (20 mL) at 0° C. was slowly added diethyl azodicarboxylate (259 mg, 1.19 mmol) and the mixture stirred for 1 h at 0° C. and then 16 h at room temperature. Water (5 mL) was added and the mixture extracted with ethyl acetate (2×10 mL). The organic solution was washed with water and brine, dried (MgSO$_4$) and concentrated to an oil which was purified by flash chromatography, (SiO$_2$—hexane/ethyl acetate 1:1) to give benzyloxycarbonyl-D-phenylglycinyl-4-(3-pyridoxy)piperidine (490 mg, 65% which was contaminated with triphenylphosphine).

Benzyloxycarbonyl-D-phenylglycinyl-R,S-3-(3-pyridoxy) pyrrolidine.

A solution of benzyloxycarbonyl-D-phenylglycinyl-R,S-3-hydroxypyrrolidine (2.0 g, 8.64 mmol), 2-triphenylphosphonium 4,4-dimethyltetrahydro-1,2,5-thiadiazolidine 1,1-dioxide (Reference: J. Castro et al., J. Org. Chem. 1994, 59, 2289–2291) (3.479 g, 8.47 mmol) and 3-hydroxypyridine (0.805 g, 8.47 mmol) in benzene (30 mL) was stirred at room temperature for 18 h. The mixture was poured onto ether (50 mL), and the organic solution was washed with satd sodium bicarbonate (2×50 mL). The product was extracted into 5% hydrochloric acid which was then basified (pH 8) with 2 M sodium hydroxide solution and extracted with ether (3×100 mL). The organic solution was dried ($MgSO_4$) and evaporated to give benzyloxycarbonyl-D-phenylglycinyl-R,S-3-(3-pyridoxy) pyrrolidine.

D-Phenylglycinyl-4-(3-pyridoxy)piperidine.

Benzyloxycarbonyl-D-phenylglycinyl-4-(3-pyridoxy) piperidine (1.18 g, 2.64 mmol) was dissolved in ethanol (120 mL) containing Pd/C 10% (100 mg) and acetic acid (0.3 mL) and hydrogenated at atmospheric pressure for 8 h (incomplete by tlc). The catalyst was removed by filtration, and the solution evaporated to an oil. The oil was re-hydrogenated as before. The catalyst was removed by filtration and the solvent evaporated in vacuo to an oil which was taken up in dilute hydrochloric acid. The aqueous solution was washed with dichloromethane and then basified with solid sodium bicarbonate. Extraction with chloroform, drying ($MgSO_4$) and evaporation of the solvent in vacuo gave D-phenylglycinyl-4-(3-pyridoxy)piperidine (331 mg, 40%).

$^1$NMR

D-phenylglycinyl-R,S-3-(3-pyridoxy)pyrrolidine.

In a similar manner D-phenylglycinyl-R,S-3-(3-pyridoxy) pyrrolidine was prepared from benzyloxycarbonyl-D-phenylglycinyl-R,S-3-(3-pyridoxy)pyrrolidine by hydrogenation over Pd/C in ethanol.

$^1$NMR 1-t-Butoxycarbonyl-4-(2-pyridoxy)piperidine.

1-t-Butoxycarbonyl-4-piperidinol (5.0 g, 24.88 mmol) in dry dimethylformamide (60 mL) was treated with sodium hydride (60%, 2.99 g, 74.75 mmol) at room temperature under argon and then with 2-chloropyridine hydrochloride (4.1 g, 27.33 mmol). Then the mixture was heated at 80° C. overnight. After cooling, the reaction was carefully quenched with water (5 mL) and then diluted with more water (20 mL) and extracted with ethyl acetate (30 mL). The organic solution was washed with satd sodium bicarbonate, dried ($MgSO_4$) and evaporated to give 1-t-butoxycarbonyl-4-(2-pyridoxy)piperidine (4.96 g, 72%).

4-(2-Pyridoxy)piperidine Dihydrochloride.

1-t-Butoxycarbonyl-4-(2-pyridoxy)piperidine (6.5 g) was treated with a solution of hydrogen chloride in ethyl acetate (110 mL) for 7 h, and the mixture evaporated to give 4-(2-pyridoxy)piperidine dihydrochloride (7.4 g, 90%).

1-(Benzyloxycarbonyl-D-phenylglycinyl)-4-(2-pyridoxy) piperidine.

Benzyloxycarbonyl-D-phenylglycine (3.75 g, 13.14 mmol) was coupled to 4-(2-pyridoxy)piperidine dihydrochloride (3.0 g, 11.94 mmol) using EDCI (2.52 g, 13.14 mmol), HOAt (1.79 g, 13.13 mmol) and triethylamine (3.63 g, 35.87 mmol) to give, after work up with ethyl acetate and sodium bicarbonate solution, 1-(benzyloxycarbonyl-D-phenylglycinyl)-4-(2-pyridoxy)piperidine (4.9 g, 92%).

1-(D-phenylglycinyl)-4-(2-pyridoxy)piperidine.

1-(Benzyloxycarbonyl-D-phenylglycinyl)-4-(2-pyridoxy) piperidine (400 m g) was hydrogenated in ethanol with 5% Pd/C overnight. Removal of catalyst and evaporation of solvent gave 1-(D-phenylglycinyl)-4-(2-pyridoxy) piperidine (162 mg, 58%).

Using a similar method and the appropriate starting materials the following intermediates are or were also prepared (also, see preparations of intermediates below):

1-(D-phenylglycinyl)-4-(4-pyridoxy)piperidine
1-(D-phenylglycinyl)-3-R,S-(4-pyridoxy)pyrrolidinamide
1-(D-phenylglycinyl)-3-R,S-(2-pyridoxy)pyrrolidinamide Example 12

1-(Indole-6-carbonyl-D-phenylglycinyl)-4-(3-pyridoxy) piperidine.

A mixture of EDCI (169 mg, 0.88 mmol), HOAt (120 mg, 0.88 mmol) and indole-6-carboxylic acid (142 mg, 0.88 mmol) in DMF (5 mL) was stirred for 2 min and then added to a solution of D-phenylglycinyl-4-(3-pyridoxy)piperidine (229 mg, 0.735 mmol) and triethylamine (89 mg, 0.88 mmol) in DMF (20 mL). The mixture was stirred at room temperature for 3 h and excess solvent removed in vacuo. The residue was taken up in ethyl acetate (150 mL) and washed with satd sodium bicarbonate (50 mL). The solution was dried ($MgSO_4$), evaporated, and the residue purified by flash chromatography ($SiO_2$—ethyl acetate:methanol 0%–5%) to give 1-(indole-6-carbonyl-D-phenylglycinyl)-4-(3-pyridoxy)piperidine (122 mg, 41%).

Hplc (Luna C18, Gradient 3, water/acetonitrile/TFA), rt, 10.8 min.

LCMS M+1 455

$^1$NMR

The following Examples 13–16 were prepared using a similar procedure to that of Example 12:

Example 13

1-(3-Chloroindole-6-carbonyl-D-phenylglycinyl)-4-(3-pyridoxy)piperidine.

From D-phenylglycinyl-4-(3-pyridoxy)piperidine and 3-chloro-6-indolecarboxylic acid:

Hplc (Luna C18, Gradient 3, water/acetonitrile/TFA), rt 11.95 min

LMCS M+1 489

$^1$NMR

Example 14

1-(Indole-6-carbonyl-D-phenylglycinyl)-3-(R,S)-(3-pyridoxy)pyrrolidine.

From D-phenylglycinyl-R,S-3-(3-pyridoxy)pyrrolidine and 6-indolecarboxylic acid.

Hplc (Luna C18, Gradient 3, water/acetonitrile/TFA), rt, 6.4 min.

LCMS M+1 441

$^1$NMR (mixture of diastereomers).

Example 15

1-(3-Chloroindole-6-carbonyl-D-phenylglycinyl)-3-(R,S)-(3-pyridoxy)pyrrolidine.

From D-phenylglycinyl-R,S-3-(3-pyridoxy)pyrrolidine and 3-chloro-6-indolecarboxylic acid.

Hplc (Luna C18, Gradient 3, water/acetonitrile/TFA), rt, 7.2 min.

LCMS M+1 475

$^1$NMR (mixture of diastereomers).

Example 16

1-(3-Methylindole-6-carbonyl-D-phenylglycinyl)-3-(R,S)-(3-pyridoxy)pyrrolidine.

From D-phenylglycinyl-R,S-3-(3-pyridoxy)pyrrolidine and 3-methyl-6-indolecarboxylic acid.

Hplc (Luna C18, Gradient 3, water/acetonitrile/TFA), rt, 6.84 and 7.0 min.
LCMS M+1 455
$^1$NMR (mixture of diastereomers).

Example 17
1-(4-Methoxybenzoyl-D-phenylglycinyl)-4-(2-pyridoxy) piperidine.
1-(D-phenylglycinyl)-4-(2-pyridoxy)piperidine (162 mg, 0.52 mmol) was treated with triethylamine (58 mg, 0.573 mmol) and p-anisoyl chloride (93 mg, 0.545 mmol) in dry dichloromethane for 1 h. The reaction mixture was washed with sodium bicarbonate solution and brine, dried (MgSO$_4$) and evaporated to an oil. Flash chromatography gave the product 1-(4-methoxybenzoyl-D-phenylglycinyl)-4-(2-pyridoxy)piperidine (60 mg, 26%).
Hplc (Luna C18, Gradient 3, water/acetonitrile/TFA), rt, 8.94 min
LCMS M+Na 468
$^1$NMR The following Examples 18–28 were prepared using a similar procedure to that of Example 12 or Example 17, as indicated.

Example 18
1-(Indol-6-carbonyl-D-phenylglycinyl)-4-(2-pyridoxy) piperidine.
By the coupling of indol-6-carboxylic acid and 1-D-phenylglycinyl-4-(2-pyridoxy)piperidine using EDCI and HOAt.
LCMS M+1 455
$^1$NMR Example 19
1-(3-Chloroindol-6-carbonyl-D-phenylglycinyl)-4-(2-pyridoxy)piperidine TFA Salt.
By the coupling of 3-chloroindol-6-carboxylic acid and 1-D-phenylglycinyl-4-(2-pyridoxy)piperidine using EDCI and HOAt.
Hplc (Luna C18, Gradient 3, water/acetonitrile/TFA), rt, 10.29 min
LCMS M+1 489
$^1$NMR Example 20
1-(3-Chloroindol-6-carbonyl-D-phenylglycinyl)-4-(4-pyridoxy)piperidine TFA Salt.
By the coupling of 3-chloroindol-6-carboxylic acid and 1-D-phenylglycinyl-4-(4-pyridoxy)piperidine using EDCI and HOAt.
Hplc (Luna C18, Gradient 3, water/acetonitrile/TFA), rt, 8.16 min
LCMS M+1 489
$^1$NMR Example 21
1-(4-Methoxybenzoyl-D-phenylglycinyl)-4-(4-pyridoxy) piperidine TFA Salt.
By the coupling of p-anisoyl chloride and 1-D-phenyl-glycinyl-4-(4-pyridoxy)piperidine in dichloromethane with triethylamine.
Hplc (Luna C18, Gradient 3, water/acetonitrile/TFA), rt, 7.0 min
LCMS M+1 446
$^1$NMR Example 21a
1-(4-Methoxybenzoyl-D-phenylglycinyl)-4-(4-pyridoxy) piperidine.
An SCX column was washed with a solution of 5% acetic acid/methanol followed by methanol, and then 1-(4-methoxybenzoyl-D-phenylglycinyl)-4-(4-pyridoxy) piperidine trifluoroacetate was dissolved in methanol and loaded onto the column. After washing the column with methanol, the product was eluted with 50% 2 N ammonia/ methanol in dichloromethane; and the product containing fractions were combined and concentrated in vacuo to give the title compound.
$^1$NMR
IS-MS, m/e 446.3 (M+1)
HPLC Analysis (Method A): 95% t$_r$=21.04 min.

Example 22
1-(Indol-6-carbonyl-D-phenylglycinyl)-4-(4-pyridoxy) piperidine TFA Salt.
By the coupling of indol-6-carboxylic acid and 1-D-phenylglycinyl-4-(4-pyridoxy)piperidine with EDCI and HOAt.
Hplc (Luna C18, Gradient 3, water/acetonitrile/TFA), rt, 7.08 min
LCMS M+1 455
$^1$NMR Example 22a
1-(Indole-6-carbonyl-D-phenylglycinyl)-4-(4-pyridoxy) piperidine.
Prepared from 1-(indole-6-carbonyl-D-phenylglycinyl)-4-(4-pyridoxy)piperidine trifluoroacetate using the procedure described in Example 21a.
$^1$NMR
IS-MS, m/e 455.1 (M+1)
HPLC Analysis (Method A): 97.8% t$_r$=21.90 min.

Example 22b
1-(Indole-6-carbonyl-D-phenylglycinyl)-4-(4-pyridoxy) piperidine Hydrochloride.
To a stirring solution of 1-(indole-6-carbonyl-D-phenylglycinyl)-4-(4-pyridoxy)piperidine (0.525 g, 1.16 mmol) in dichlormethane (5 mL) was added a 1 M solution of HCl in diethyl ether (1.27 mL, 1.27 mmol), resulting in the precipitation of a white solid. The stirring suspension was diluted with anhydrous diethyl ether, sonicated and filtered to give 0.50 g (88%) of the title compound.
$^1$NMR
IS-MS, m/e 455.1 (M+1)

Analysis for $C_{27}H_{26}N_4O_3 \cdot 1.0$ HCl$\cdot 2.0$ H$_2$O$\cdot 0.5$ CH$_2$Cl$_2$:

Calcd: C, 58.00; H, 5.66; N, 9.84; Cl, 12.45;
Found: C, 58.07; H, 5.28; N, 9.60; Cl, 11.95.

HPLC Analysis (Method A): 100% t$_r$=22.52 min.

Example 23
1-(4-Methoxybenzoyl-D-phenylglycinyl)-3-R,S-(4-pyridoxy)pyrrolidinamide.
By the coupling of p-anisoyl chloride and 1-(D-phenylglycinyl)-3-R,S-(4-pyridoxy)pyrrolidinamide in dichloromethane with triethylamine.
LCMS M+1 432
$^1$NMR

Example 24
1-(Indol-6-carbonyl-D-phenylglycinyl)-3-R,S-(4-pyridoxy) pyrrolidinamide.

By the coupling indol-6-carboxylic acid and 1-(D-phenylglycinyl)-3-R,S-(4-pyridoxy)pyrrolidinamide with EDCI and HOAt.

LCMS M+1 441
[1]NMR

Example 25
1-(3-Chloroindol-6-carbonyl-D-phenylglycinyl)-3-R,S-(4-pyridoxy)pyrrolidinamide.

By the coupling 3-chloroindol-6-carboxylic acid and 1-(D-phenylglycinyl)-3-R,S-(4-pyridoxy)pyrrolidinamide with EDCI and HOAt.

LCMS M+1 475
[1]NMR

Example 26
1-(4-Methoxybenzoyl-D-phenylglycinyl)-3-R,S-(2-pyridoxy)pyrrolidinamide.

By the coupling of p-anisoyl chloride and 1-(D-phenylglycinyl)-3-R,S-(2-pyridoxy)pyrrolidinamide in dichloromethane with triethylamine.

LCMS M+1 432
[1]NMR

Example 27
1-(3-Chloroindol-6-carbonyl-D-phenylglycinyl)-3-R,S-(2-pyridoxy)pyrrolidinamide.

By the coupling 3-chloroindol-6-carboxylic acid and 1-(D-phenylglycinyl)-3-R,S-(2-pyridoxy)pyrrolidinamide with EDCI and HOAt.

LCMS M+1 475
[1]NMR

Example 28
1-(Indol-6-carbonyl-D-phenylglycinyl)-3-R,S-(2-pyridoxy) pyrrolidinamide.

By the coupling indol-6-carboxylic acid and 1-(D-phenylglycinyl)-3-R,S-(2-pyridoxy)pyrrolidinamide with EDCI and HOAt.

LCMS M+1 441
[1]NMR

NO EXAMPLE 29–30

In the following examples the following additional abbreviations and meanings are included: CI-MS, chemical ionization mass spectrum; DMSO, dimethyl sulfoxide (perdeuterated if for NMR); EtOAc, ethyl acetate; EtOH, ethanol; IS-MS, ion spray mass spectrum; RPHPLC, reverse phase HPLC; SCX, strong cation exchange resin; THF, tetrahydrofuran; TLC, thin layer chromatography with $R_f$ as relative mobility;

Reagents were obtained from a variety of commercial sources.

IR means an infrared spectrum was obtained. [1]NMR, 1H-NMR, or 1H NMR means a proton magnetic resonance spectrum was obtained.

In general in this specification, "D-" or "R-" in the name of a product indicates the product was made beginning with a chiral starting material, for example D-phenylglycine; however, racemization may have occurred, and the enantiomeric purity may not have been determined.

HPLC Analysis (Method A): Vydac C18 (4.6×250 mm), elute with a linear gradient of 90/10 through 50/50 (0.1% TFA in water/0.1% TFA in acetonitrile) over 40 min, 1 mL/min.

(Method B): Waters Symmetry, C18 (4.6×250 mm) column. The elution system consisted of linear gradient from 95:5 (0.2% TFA in $H_2O$)/(0.2% TFA in $CH_3CN$) to 5:95 (0.2% TFA in $H_2O$)/(0.2% TFA in $CH_3CN$) over 20 min, followed by (0.2% TFA in $CH_3CN$) isocratic over 15 min. The flow rate was 1 ml/min. UV Detection was performed at 254 nm unless otherwise noted.

API-MS (atmospheric pressure chemical ionization mass spectra) were obtained on a PESciex API 150EX with a heated nebulizer and nitrogen as the reagent gas in positive ion mode.

CI-MS (Chemical ionization mass spectra) were obtained on a Shimadzu 5000 direct insertion mass spectrometer in chemical ionization mode utilizing methane as the reagent gas.

The following abbreviations are used throughout: CMA (chloroform:methanol:concentrated ammonium hydroxide, 80:18:2), THF (tetrahydrofuran), DEPC (diethyl cyanophosphonate).

Preparation of Intermediates A-1–A-6

The following compounds were prepared according to the indicated method (Method A-A or Method A-B) from the indicated starting materials, unless otherwise described.

Intermediate A-1
1-Boc-4-(pyridin-3-ylamino)piperidine.

Method A-A

3-Aminopyridine (940 mg, 10 mmol), 1-Boc-4-piperidone (2.0 g, 10 mmol), $NaBH(OAc)_3$ (3.1 g, 15 mmol), and acetic acid (120 mg) were combined in $CH_2Cl_2$ (20 mL). The reaction was stirred 5 h, and was then quenched with 1 M $NaHSO_4$. After stirring 10 min, the mixture was made basic with 10% $K_2CO_3$ and extracted with 4 portions of $CH_2Cl_2$. The organics were combined and evaporated under vacuum to provide 2.76 g of the crude product which was purified by chromatography ($SiO_2$, 200:10:1 $CH_2Cl_2$:MeOH:$NH_4OH$) to afford the title compound (1.05 g, 38%).

$^1$H NMR ($CDCl_3$)

TLC $R_f$=0.53 (15:1 $CH_2Cl_2$:MeOH, $SiO_2$, Analtech No. 02521)

Intermediate A-2
1-Benzyl-4-(pyridin-4-ylamino)piperidine.

Method A-B

Under $N_2$ purge, 1-benzyl-4-aminopiperidine (2.0 g, 10.5 mmol), 4-bromopyridine.HCl (2.3 g, 11.6 mmol), and sodium-t-butoxide (2.3 g, 23.1 mmol) were combined in 1,4-dioxane (40 mL). Tris(dibenzylidineacetone) dipalladium (960 mg, 1.05 mmol), and tri-t-butylphosphine (170 mg, 0.84 mmol) were added, and the reaction was allowed to stir at 80° C. for 3 h.

The reaction was cooled, diluted with EtOAc, filtered, washed with water, dried over $Na_2SO_4$ and evaporated to afford the crude product. Chromatography ($SiO_2$, 200:10:1 $CH_2Cl_2$:MeOH:$NH_4OH$) afforded the title compound (1.7 g, 60%) as an off white solid.

$^1$H NMR ($CDCl_3$)

CI-MS, m/e=268 (M+1)

Intermediate A-3
1-Benzyl-4-(pyridin-2-ylamino)piperidine.

Prepared from 2-bromopyridine and 1-benzyl-4-aminopiperidine using Method A-B.

¹H NMR (CD₃OD)
API-MS, m/e=268 (M+1)

Intermediate A-4
1-Boc-4-(Pyridin-4-yloxy)piperidine.

Prepared from 1-Boc-4-hydroxypiperidine and 4-fluoropyridine using methods substantially equivalent to those described for the synthesis of 1-Boc-4-(pyridin-2-yloxy)piperidine. The product was purified by chromatography over silica gel, eluting with ethyl acetate.
¹NMR
IS-MS, m/e 279.0 (M+1)

Intermediate A-5
1-Boc-4-(6-Methylpyridin-2-yloxy)piperidine.

Prepared from 1-Boc-4-hydroxypiperidine and 2-chloro-6-methylpyridine using methods substantially equivalent to those described for the synthesis of 1-Boc-4-(pyridin-2-yloxy)piperidine. The product was purified by chromatography over silica gel, eluting with a gradient of 0–15% ethyl acetate in hexanes.
¹NMR
IS-MS, m/e 293.0 (M+1)

Intermediate A-6
1-Boc-4-(2-Cyanopyridin-4-yloxy)piperidine.

Prepared from 1-Boc-4-hydroxypiperidine and 4-chloro-2-cyanopyridine using methods substantially equivalent to those described for the synthesis of 1-Boc-4-(pyridin-2-yloxy)piperidine. The product was purified by chromatography over silica gel, eluting with 25% ethyl acetate in hexanes.
¹NMR
IS-MS, m/e 304.0 (M+1)

| Analysis for $C_{16}H_{21}N_3O_3$ |
| --- |
| Calcd: C, 63.35; H, 6.98; N, 13.85; |
| Found: C, 63.27; H, 7.05; N, 13.68. |

Preparation of Intermediates B-1–B-6

The following compounds were prepared according to the indicated method (Method B-A or Method B-B) from the indicated starting materials, unless otherwise described.

Intermediate B-1
1-(Pyridin-3-ylamino)piperidine.

Method B-A

Concentrated hydrochloric acid (67 mL) was added to a stirring solution of 1-Boc-4-aminopyridin-3-ylpiperidine (11.0 g, 40 mmol), and ethanol (200 mL). After 3 h, the product mixture was evaporated to a solid under vacuum. The solid was dissolved in 1:1 water:methanol, and passed through a strong cation exchange resin {170 g, Dowex, 50Wx8–200 H⁺ form, pretreated with 20:1 methanol:AcOH (300 mL), then packed and flushed with methanol (300 mL), first eluted with methanol (1 L), and finally with 1:1 methanol:concentrated ammonium hydroxide (2 L)} to provide the crude product. The solution was evaporated under vacuum, and the residue was purified by treatment of a methanolic solution with charcoal, filtration, and recrystallization (toluene, ether). The product was vacuum dried at 40° C. to provide the title compound (5.1 g, 73%) as an off white solid.

Melting Point=128–132° C.
¹H NMR (CDCl₃)
CI-MS, m/e=178 (M+1)

Intermediate B-2
1-(Pyridin-4-ylamino)piperidine.

Method B-B

1-Benzyl-4-(pyridin-4-ylamino)piperidine (15.4 g, 58 mmol), and 20% Pd(OH)₂/C (5 g) were combined in ethanol (200 mL), and charged to 2.04 bar (30 psig) H₂ overnight. The catalyst was removed by suction filtration through diatomaceous earth; and, after evaporation under vacuum, the product was purified by recrystallization (toluene, methanol).

The supernate was evaporated, resubjected to hydrogenation and purification conditions, and combined with first fraction to provide the title compound (7.9 g, 77%) as an off white solid.
¹H NMR (CD₃OD)
CI-MS, m/e=178 (M+1)

Intermediate B-3
1-(Pyridin-2-ylamino)piperidine.

Prepared from 1-benzyl-4-(pyridin-2-ylamino)piperidine using Method B-B.
¹H NMR (CD₃OD)
API-MS, m/e=178 (M+1)

Intermediate B-4
4-(Pyridin-4-yloxy)piperidine dihydrochloride.

Prepared from 1-Boc-4-(pyridin-4-yloxy)piperidine using methods substantially equivalent to those described for the synthesis of 4-(pyridin-2-yloxy)piperidine dihydrochloride, using ethanol in place of ethyl acetate. The product was isolated by trituration with diethyl ether.
¹NMR
IS-MS, m/e 179.2 (M+1)

Intermediate B-5
4-(6-Methylpyridin-2-yloxy)piperidine Dihydrochloride.

Prepared from 1-Boc-4-(6-methylpyridin-2-yloxy) piperidine using methods substantially equivalent to those described for the synthesis of 4-(pyridin-2-yloxy)piperidine dihydrochloride, using ethanol in place of ethyl acetate. The product was isolated by trituration with diethyl ether.
¹NMR
IS-MS, m/e 193.1 (M−1)

Intermediate B-6
4-(2-Cyanopyridin-4-yloxy)piperidine.

Prepared from 1-Boc-4-(2-cyanopyridin-4-yloxy) piperidine using Method D-A.
¹NMR
IS-MS, m/e 204.1 (M+1)

Preparation of Intermediates C-1–C-10

The following compounds were prepared according to the indicated method (Method C-A, Method C-B or Method C-C) from the indicated starting materials, unless otherwise described.

Intermediate C-1
1-(Boc-D-phenylglycinyl)-4-(pyridin-3-ylamino)piperidine.

Method C-A

To a stirring solution of Boc-D-phenylglycine (2 g, 7.96 mmol), 4-(pyridin-3-yl)aminopiperidine (1.4 g, 7.96 mmol) and DECP (1.2 mL, 7.96 mmol) in DMF (20 mL) was added triethylamine (1.1 mL, 7.96 mmol). After stirring overnight, the solvent was removed in vacuo. The residue was dissolved in ethyl acetate and washed with satd aq. NaHCO₃ followed by brine. The organic phase was then dried with MgSO₄, filtered and concentrated. The product was then dissolved in a minimal amount of ethyl acetate and precipitated with hexanes. The precipitate was filtered and dried to give 1.76 g (54%) of the title compound.

1H-NMR

IS-MS, m/e 411.7 (M+1)

Intermediate C-2

1-[Boc-D,L-(pyridin-2-yl)glycinyl]-4-(pyridin-3-ylamino) piperidine.

Method C-B

To a stirring solution of ethyl Boc-D,L-(pyridin-2-yl) glycine (16.3 g, 58.2 mmol) in 1,4-dioxane (100 mL) was added a solution of LiOH hydrate (2.68 g, 64 mmol) in water (100 mL). After 2 h, another solution of LiOH hydrate (1.34 g, 32 mmol) in water (50 mL) was added. After another 2 h, the solvent was evaporated in vacuo to give 13.56 g of off-white solid.

A portion of the solid (3 g, 11.6 mmol) was dissolved in DMF (75 mL) and cooled to 0° C. To this solution was added diethyl cyanophosphonate (1.94 mL, 11.6 mmol), N,N-diisopropylethylamine (3.24 mL, 23.24 mmol) and then 4-(pyridin-3-ylamino)piperidine (2.1 g, 11.6 mmol); and the reaction was allowed to slowly warm to room temperature overnight. The next morning, the solvents were removed in vacuo and the residue was dissolved in ethyl acetate and washed with satd aq. NaHCO$_3$ and brine, then dried with Na$_2$SO$_4$, filtered, and concentrated in vacuo. The residue was then dissolved in a minimal volume of dichloromethane and chromatographed over silica gel, eluting with ethyl acetate, followed by a step gradient of 2% through 15% (2 N ammonia/methanol) in dichloromethane. The product containing fractions were combined and concentrated in vacuo to give 2.4 g (50%) of an off-white solid.

1H-NMR

IS-MS, m/e 412.3 (M+1)

Intermediate C-3

1-(Boc-D-phenylglycinyl)-4-(pyridin-4-ylamino)piperidine.

Method C-C 4-(Pyridin-4-ylamino)piperidine (1.4 g, 8.0 mmol) and Boc-D-phenylglycine (2.0 g, 8.0 mmol) were combined, and cooled to −15° C. in stirring CH$_2$Cl$_2$ (40 mL), under N$_2$ atmosphere. DEPC (1.6 mL, 9.6 mmol) was added, followed by triethylamine (1.1 mL, 8.0 mmol). The reaction was allowed to stir to room temperature as the ice-methanol bath thawed overnight. Water was added, and the mixture was extracted with 3 portions of CH$_2$Cl$_2$. The organics were combined, washed with brine, and evaporated to afford 2 g of the crude product, which was purified by chromatography (200:10:1, CH$_2$Cl$_2$:MeOH:NH$_4$OH), vacuum dried at 60° C. to afford the title compound (1.7 g, 52%).

$^1$H NMR (CDCl$_3$)

CI-MS, m/e=411 (M+1)

Intermediate C-4

1-(Boc-D-phenylglycinyl)-4-(pyridin-2-ylamino)piperidine.

Prepared from Boc-D-phenylglycine and and 4-(pyridin-2-ylamino)piperidine using Method C-C.

$^1$H NMR (CDCl$_3$)

API-MS, m/e=411 (M+1)

Intermediate C-5

1-[Boc-D,L-(pyridin-2-yl)glycinyl]-4-(pyridin-2-yloxy) piperidine.

Prepared from ethyl Boc-D,L-pyridin-2-ylglycine and and 4-(pyridin-2-yloxy)piperidine using Method C-B.

$^1$H NMR

IS-MS, m/e=413.3 (M+1)

Intermediate C-6

1-[Boc-D,L-(pyridin-2-yl)glycinyl]-4-(pyridin-4-yloxy) piperidine.

Prepared from ethyl Boc-D,L-pyridin-2-ylglycine and and 4-(pyridin-4-yloxy)piperidine using Method C-B.

$^1$H NMR

IS-MS, m/e=413.3 (M+1)

Intermediate C-7

1-(Boc-D,L-2-Chlorophenyl)glycinyl-4-(pyridin-4-yloxy) piperidine.

To a stirring suspension of Boc-D,L-2-chlorophenylglycine (7.23 g, 25.3 mmol) and 4-(pyridin-4-yloxy)piperidine dihydrochloride (5.3 g, 21.1 mmol)in DMF (150 mL) was added HOAt (3.45 g, 25.3 mmol), triethylamine (13 mL, 84 mmol), and finally EDCI (4.85 g, 25.3 mmol). After 3 days, the solvents were removed in vacuo and the residue was partitioned with satd aq. NaHCO$_3$. The layers were separated and the organic phase was washed with brine, dried over anhydrous Na$_2$SO$_4$, filtered, and concentrated in vacuo. The resulting solid was then dissolved in a minimal amount of chloroform and chromatographed over silica gel, eluting with 5% 2 N ammonia/methanol in chloroform. The product containing fractions were combined and concentrated to give 2.3 g (24%) of the title compound.

$^1$NMR

IS-MS, m/e 446.3 (M+1)

Intermediate C-8

1-[Boc-D,L-(Quinolin-8-yl)glycinyl]-4-(pyridin-4-yloxy) piperidine.

To a stirring suspension of Boc-D,L-(quinolin-8-yl) glycine (0.49 g, 1.62 mmol) and 4-(pyridin-4-yloxy) piperidine dihydrochloride (0.49 g, 1.94 mmol) in dichloromethane (25 mL) was added N,N-diisopropylethylamine (0.68 mL, 3.88 mmol) followed by HOAt (0.22 g, 1.62 mmol) and finally EDCI (0.31 g, 1.62 mmol). After stirring overnight, the solvents were removed in vacuo and the residue was partitioned between dichloromethane and satd aq. NaHCO$_3$. The organic phase was separated and washed with satd aq. NaHCO$_3$ followed by brine, then dried with MgSO$_4$, filtered and concentrated in vacuo to give 0.512 g (68%) of the title compound.

$^1$NMR

IS-MS, m/e 463.2 (M+1)

Intermediate C-9

1-(Boc-D-phenylglycinyl)-4-(6-methylpyridin-2-yloxy) piperidine.

Prepared from Boc-D-phenylglycine and 4-(6-methylpyridin-2-yloxy)piperidine dihydrochloride using Method C-A. The product was purified by chromatography over silica gel, eluting with a gradient of 0–5% methanol in dichloromethane.

$^1$NMR

IS-MS, m/e 426.0 (M+1)

Intermediate C-10

1-(Boc-D-Phenylglycinyl)-4-(2-cyanopyridin-4-yloxy) piperidine.

Prepared from Boc-D-phenylglycine and 4-(2-cyanopyridin-4-yloxy)piperidine using Method C-A. The product was purified by chromatography over silica gel, eluting with a gradient of 0–8% 2 N ammonia/methanol in dichloromethane.

$^1$NMR

IS-MS, m/e 435.0 (M−1)

Preparation of Intermediates D-1–D-11

The following compounds were prepared according to the indicated method (Method D-A or Method D-B) from the indicated starting materials, unless otherwise described.

Intermediate D-1
1-(D-Phenylglycinyl)-4-(pyridin-3-ylamino)piperidine.

Method D-A

To a stirring solution of 1-(Boc-D-phenylglycinyl)-4-(pyridin-3-ylamino)piperidine (1.76 g, 4.3 mmol) in dichloromethane (90 mL) was added TFA (10 mL). After stirring for 2 h, the solvent was removed in vacuo. The residue was dissolved in methanol and loaded onto an SCX column. The column was eluted with methanol, followed by a 30% solution of (2 N ammonia/methanol) in dichloromethane. The product containing fractions were combined and concentrated in vacuo to give 1.4 g (quantitative) of the title compound.
1H-NMR
IS-MS, m/e 311.3 (M+1)
Intermediate D-2
1-[D,L-(Pyridin-2-yl)glycinyl]-4-(pyridin-3-ylamino)piperidine.
Prepared from 1-[Boc-D,L-(pyridin-2-yl)glycinyl]-4-(pyridin-3-ylamino)piperidine using Method D-A. The title compound was further purified by chromatography over silica gel, eluting with a step gradient of 2% through 15% (2 N ammonia/methanol) in dichloromethane.
1H-NMR
IS-MS, m/e 312.4 (M+1)
Intermediate D-3
1-(D-Phenylglycinyl)-4-(pyridin-4-ylamino)piperidine.

Method D-B

Concentrated hydrochloric acid (4 mL), was added to an ice cooled stirring solution of 1-(Boc-D-phenylglycinyl)-4-(pyridin-4-ylamino)piperidine (1.7 g, 4.0 mmol) and anisole (1.5 mL) in methanol (5 mL). After stirring at room temperature for 3 h, the mixture was evaporated under vacuum, and partitioned between 10% $K_2CO_3$, and EtOAc. The basic mixture was extracted with 2:1 EtOAc, THF, dried over $K_2CO_3$, evaporated under vacuum, and vacuum dried at 50° C. to give the product (1.0 g, 80%) as an off white solid.
$^1$H NMR (CD$_3$OD)
CI-MS, m/e=311 (M+1)
Intermediate D-4
1-(D-Phenylglycinyl)-4-(pyridin-2-ylamino)piperidine.
Prepared from 1-(Boc-D-phenylglycinyl)-4-(pyridin-2-ylamino)piperidine using Method D-B.
$^1$H NMR (CD$_3$OD)
API-MS, m/e=311 (M+1)
Intermediate D-5
1-[D,L-(Pyridin-2-yl)glycinyl]-4-(pyridin-2-yloxy)piperidine.
Prepared from 1-[Boc-D,L-(pyridin-2-yl)glycinyl]-4-(pyridin-2-yloxy)piperidine using Method D-A.
$^1$H NMR
IS-MS, m/e=313.3 (M+1)
Intermediate D-6
1-[D,L-(Pyridin-2-yl)glycinyl]-4-(pyridin-4-yloxy)piperidine.
Prepared from 1-[Boc-D,L-(pyridin-2-yl)glycinyl]-4-(pyridin-4-yloxy)piperidine using Method D-A.
$^1$H NMR
IS-MS, m/e=313.3 (M+1)
Intermediate D-7
1-(D,L-2-Chlorophenyl)glycinyl-4-(pyridin-4-yloxy)piperidine.
Prepared from 1-(Boc-D,L-2-chlorophenyl)glycinyl-4-(pyridin-4-yloxy)piperidine using Method D-A.
$^1$NMR
IS-MS, m/e 345.9 (M+1)
Intermediate D-8
1-[D,L-(Quinolin-8-yl)glycinyl]-4-(pyridin-4-yloxy)piperidine.
Prepared from 1-[Boc-D,L-(quinolin-8-yl)glycinyl]-4-(pyridin-4-yloxy)piperidine using Method D-A.
$^1$NMR
Intermediate D-9
1-(D-Phenylglycinyl)-4-(6-methylpyridin-2-yloxy)piperidine.
Prepared from 1-(Boc-D-phenylglycinyl)-4-(6-methylpyridin-2-yloxy)piperidine using Method D-A.
$^1$NMR
IS-MS, m/e 326.0 (M+1)
Intermediate D-10
1-(D-Phenylglycinyl)-4-(2-cyanopyridin-4-yloxy)piperidine.
Prepared from 1-(Boc-D-phenylglycinyl)-4-(2-cyanopyridin-4-yloxy)piperidine using Method D-A.
$^1$NMR
IS-MS, m/e 337.1 (M+1)
Intermediate D-11
1-[D,L-(2-aminothiazol-4-yl)glycinyl]-4-(4-pyridoxy)piperazine.
To a solution of Boc-D,L-2-benzyloxycarbonylamino-4-thiazolylglycine (2.08 g, 5.1 mmol), HOAt (765 mg, 5.61 mmol), 4-(pyridin-4-yloxy)piperidine dihydrochloride(1.28 g, 5.1 mmol) and triethylamine (1.578 mL, 11.2 mmol) in DMF (41 mL) was added EDCI (1.08 g, 5.61 mmol) and the mixture stirred at room temperature for 19 h. The solvent was removed in vacuo, the residues taken up in chloroform: isopropyl alcohol (2:1) and washed with water, satd aqueous sodium bicarbonate, dried (MgSO$_4$) and concentrated in vacuo. The resulting orange-brown oil was dissolved in HBr-acetic acid (50%, 35 mL) and acetic acid (70 mL), and the solution was heated at 60° C. for 6 h, cooled and then concentrated in vacuo. The product was isolated using SCX ion exchange chromatography.
$^1$NMR Preparation of Intermediates E-1–I-1

The following compounds were prepared according to the indicated method (Method E-A, Method F-A, Method G-A, Method H-A) from the indicated starting materials, unless otherwise described.
Intermediate E-1
1-(Boc-D-phenylglycinyl)-4-hydroxypiperidine.

Method E-A

To a stirring solution of HOAT (10.24 g, 75.2 mmol) and EDCI (14.42 g, 75.2 mmol) in DMF (160 mL) was added a solution of Boc-D-phenylglycine (18.9 g, 75.2 mmol) in DMF (80 mL). After 10 min, 4-hydroxypiperidine (6.85 g, 67.7 mmol) was added. After stirring over night, the solvent was evaporated in vacuo and the residue was partitioned between ethyl acetate and water. The organic phase separated and washed with satd aq. NaHCO$_3$, followed by brine, dried over MgSO$_4$, flitered and concentrated in vacuo. Two-thirds of this material was dissolved in a minimum amount of dichloromethane and chromatographed over silica gel, eluting with a gradient of dichloromethane through 1:1 dichloromethane:ethyl acetate. The product containing fractions were combined and concentrated in vacuo to give 15.71 g (94%) of a white foam.

1H-NMR
IS-MS, m/e 335.1 (M+1)

| Analysis for $C_{18}H_{26}N_2O_4$: | |
|---|---|
| Calcd: | C, 64.65; H, 7.84; N, 8.37; |
| Found: | C, 64.40; H, 7.77; N, 8.12. |

Intermediate F-1
1-(D-Phenylglycinyl)-4-hydroxypiperidine.

Method F-A

To a stirring solution of 1-(Boc-D-phenylglycinyl)-4-hydroxypiperidine (5 g, 15 mmol) in dichloromethane (290 mL) was added anisole (8 mL) followed by trifluoroacetic acid (29 mL). After stirring for 4 h, the solvent was concentrated in vacuo and the residue was suspended with stirring in diethyl ether. After 1 h, the mixture was filtered and the solid was partitioned between ethyl acetate and satd aq. NaHCO$_3$. The organic phase was washed with brine, dried with MgSO$_4$, filtered and concentrated to give 0.41 g of white solid. The combined aqueous phase was back extracted with 3:1 chloroform:isopropanol; and this organic phase was separated, dried with MgSO$_4$, filtered and concentrated in vacuo to give 1.6 g of white solid. The two crops of solid were combined to give 2.02 g (90%) of the title compound.
1H-NMR
IS-MS, m/e 235.1 (M+1)

Intermediate G-1
1-(4-Methoxybenzoyl-D-phenylglycinyl)-4-hydroxypiperidine.

Method G-A

To a stirring solution of 1-[3-(dimethylamino)propyl]-3-ethylcarbodiimide hydrochloride (1.4 g, 7.4 mmol), 1-hydroxybenzotriazole hydrate (1.0 g, 7.4 mmol) and N,N-diisopropylethylamine (1.4 mL) in DMF (20 mL) was added a solution of 1-(D-phenylglycinyl)-4-hydroxypiperidine (2.0 g, 7.38 mmol) in DMF (10 mL), followed by a solution of 4-methoxybenzoic acid (1.0 g, 6.7 mmol) in DMF (10 mL). After stirring overnight at room temperature, the solvent was removed in vacuo and the residue was partitioned between ethyl acetate and water. The organic phase was washed again with water followed by satd aq. NaHCO$_3$ (2×) and brine, then dried with MgSO$_4$, filtered and concentrated in vacuo to give 2.4 g of off-white solid. A portion of this material (2.0 g) was dissolved in a minimal amount of dichloromethane and chromatographed over silica gel, eluting with a gradient of dichloromethane through 50% ethyl acetate:dichloromethane. The product-containing fractions were combined and concentrated in vacuo to give 1.3 g (60%) of a white foam.
1H-NMR
IS-MS, m/e 369.2 (M+1)

| Analysis for $C_{21}H_{24}N_2O_4$: | |
|---|---|
| Calcd: | C, 68.46; H, 6.57; N, 7.60; |
| Found: | C, 67.88; H, 6.73; N, 7.33. |
| HPLC Analysis (Method A): | 100%, $t_r$ = 24.24 min. |

Intermediate H-1
1-(4-Methoxybenzoyl-D-phenylglycinyl)-4-piperidinone.

Method H-A

To a stirring solution of oxalyl chloride (0.26 mL, 3 mmol) in dichloromethane (6.5 mL) at −50° C., was added a solution of DMSO (0.43 mL, 6 mmol) in dichloromethane (1.3 mL). After 3 min, a solution of 1-(4-methoxybenzoyl-D-phenylglycinyl)-4-hydroxypiperidine (1.0 g, 2.7 mmol) in dichloromethane (4 mL) was added and the solution was allowed to warm to −20° C. over 45 min. Triethylamine (2 mL) was then added and the solution was allowed to warm to room temperature. The solution was then diluted with dichloromethane and water, and the layers were separated. The organic phase was washed with brine, dried over MgSO$_4$, filtered and concentrated in vacuo. The residue was dissolved in a minimum amount of dichloromethane and chromatographed over silica gel, eluting with a gradient of dichloromethane through 50% ethyl acetate/dichloromethane. The product containing fractions were combined and concentrated in vacuo to give 0.77 g (78%) of a white foam.
1H-NMR
IS-MS, m/e 367.2 (M+1)

| Analysis for $C_{21}H_{22}N_2O_4$: | |
|---|---|
| Calcd: | C, 68.84; H, 6.05; N, 7.65; |
| Found: | C, 68.33; H, 6.01; N, 7.27. |
| HPLC Analysis (Method A): | 100% $t_r$ = 25.52 min. |

Intermediate I-1
1-(Boc-D-phenylglycinyl)-4-piperidinone.
Prepared from 1-(Boc-D-phenylglycinyl)-4-hydroxypiperidine using Method H-A.
1H-NMR
IS-MS, m/e 331.1 (M−1)

| Analysis for $C_{18}H_{24}N_2O_4$: | |
|---|---|
| Calcd: | C, 65.04; H, 7.28; N, 8.43; |
| Found: | C, 64.66; H, 7.29; N, 8.24. |

PREPARATION OF EXAMPLES 31–48

The following compounds were prepared according to the indicated method (Method 1-A or Method 1-B) from the indicated starting materials, unless otherwise described.

Example 31
1-(Indole-6-carbonyl-D-phenylglycinyl)-4-(pyridin-3-ylamino)piperidine.

Method 1-A

To a stirring solution of 1-D-phenylglycinyl-4-(pyridin-3-ylamino)piperidine (0.3 g, 0.97 mmol), indole-6-carboxylic acid (0.156 g, 0.97 mmol) and HOBt (0.13 g, 0.97 mmol) in DMF (10 mL), was added DCC (0.198 g, 0.97 mmol). After stirring overnight, the mixture was filtered and the filtrate was concentrated in vacuo. The residue was dissolved in ethyl acetate and washed with satd aq. NaHCO$_3$, followed by brine, then dried with MgSO$_4$, filtered and concentrated in vacuo. The residue was then dissolved in 1% acetic acid in methanol and loaded onto an SCX column. The column was then washed with methanol, then eluted with 30% (2 N ammonia/methanol) in dichloromethane. The product containing fractions were combined and concentrated in vacuo to give 0.41 g (93%) of the title compound as an off-white solid.
1H-NMR
IS-MS, m/e 454.3 (M+1)

| Analysis for $C_{27}H_{27}N_5O_2 \cdot 1.2\ H_2O$: | |
|---|---|
| Calcd: | C, 68.25; H, 6.24; N, 14.74; |
| Found: | C, 68.60; H, 6.13; N, 13.96. |
| HPLC Analysis (Method A): | 97.5% $t_r$ = 22.34 min. |

Example 32
1-(3-Methylindole-6-carbonyl-D-phenylglycinyl)-4-(pyridin-3-ylamino)piperidine.

Prepared from 3-methylindole-6-carboxylic acid and 1-D-phenylglycinyl-4-(pyridin-3-ylamino)piperidine using Method 1-A.
1H-NMR
IS-MS, m/e 468.5 (M+1)

| Analysis for $C_{28}H_{29}N_5O_2 \cdot 1.2\ H_2O$: | |
|---|---|
| Calcd: | C, 68.75; H, 6.57; N, 14.32; |
| Found: | C, 69.16; H, 6.59; N, 13.39. |
| HPLC Analysis (Method A): | 97.1% $t_r$ = 26.07 min. |

Example 33
1-(3-Chloroindole-6-carbonyl-D-phenylglycinyl)-4-(pyridin-3-ylamino)piperidine.

Prepared from 3-chloroindole-6-carboxylic acid and 1-D-phenylglycinyl-4-(pyridin-3-ylamino)piperidine using Method 1-A.
1H-NMR
IS-MS, m/e 488.2 (M+1)

| Analysis for $C_{27}H_{26}N_5O_2Cl \cdot 0.8\ H_2O$: | |
|---|---|
| Calcd: | C, 64.54; H, 5.54; N, 13.94; |
| Found: | C, 64.88; H, 5.54; N, 13.46. |
| HPLC Analysis (Method A): | 97% $t_r$ = 28.55 min. |

Example 34
1-(4-Methoxybenzoyl-D-phenylglycinyl)-4-(pyridin-3-ylamino)piperidine.

Method 1-B

To a stirring solution of 1-(4-methoxybenzoyl-D-phenylglycinyl)-4-piperidinone (0.1 g, 0.273 mmol) in 1,2-dichloroethane (5 mL) was added 3-aminopyridine (0.039 g, 0.41 mmol). After 3 h, NaBH(OAc)₃ (0.087 g, 0.41 mmol) was added and stirring continued overnight. The next morning, the solution was diluted with dichloromethane and washed with water, followed by brine, then dried over NaSO₄, filtered and concentrated in vacuo. The crude product was purified by chromatography over silica gel, eluting with 10 % (2 N ammonia/methanol) in dichloromethane. The product containing fractions were combined and concentrated to give 0.1 g (83%) of the title compound.
1H-NMR
IS-MS, m/e 445.2 (M+1)

| Analysis for $C_{26}H_{28}N_4O_3 \cdot H_2O$: | |
|---|---|
| Calcd: | C, 67.51; H, 6.54; N, 12.11; |
| Found: | C, 67.90; H, 6.63; N, 10.27. |
| HPLC Analysis (Method A): | 100% $t_r$ = 22.22 min. |

Example 35
1-[Indole-6-carbonyl-D,L-(pyridin-2-yl)glycinyl]-4-(pyridin-3-ylamino)piperidine Dihydrochloride.

Prepared from indole-6-carboxylic acid and 1-[D,L-(pyridin-2-yl)glycinyl]-4-(pyridin-3-ylamino)piperidine using Method 1-A.
1H-NMR
IS-MS, m/e 455.5 (M+1)

| Analysis for $C_{26}H_{26}N_6O_2 \cdot 2.3\ HCl \cdot 3.0\ H_2O$: | |
|---|---|
| Calcd: | C, 52.71; H, 5.84; N, 14.19; Cl, 13.77; |
| Found: | C, 52.87; H, 5.15; N, 13.65; Cl, 14.02. |
| HPLC Analysis (Method A): | 98.5% $t_r$ = 13.20 min. |

Example 36
1-[3-Methylindole-6-carbonyl-D,L-(pyridin-2-yl)glycinyl]-4-(pyridin-3-ylamino)piperidine.

Prepared from 3-methylindole-6-carboxylic acid and 1-[D,L-(pyridin-2-yl)glycinyl]-4-(pyridin-3-ylamino)piperidine using Method 1-A.
1H-NMR
IS-MS, m/e 469.5 (M+1)

| Analysis for $C_{27}H_{28}N_6O_2 \cdot 1.8\ H_2O$: | |
|---|---|
| Calcd: | C, 64.73; H, 6.36; N, 16.78; |
| Found: | C, 65.07; H, 6.01; N, 16.42. |
| HPLC Analysis (Method A): | 97.5% $t_r$ = 18.82 min. |

Example 37
1-[3-Chloroindole-6-carbonyl-D,L-(pyridin-2-yl)glycinyl]-4-(pyridin-3-ylamino)piperidine Dihydrochloride.

Prepared from 3-chloroindole-6-carboxylic acid and 1-[D,L-(pyridin-2-yl)glycinyl]-4-(pyridin-3-ylamino)piperidine using Method 1-A.
1H-NMR
IS-MS, m/e 489.5 (M+1)

| Analysis for $C_{26}H_{25}N_6O_2Cl \cdot 2.0\ HCl \cdot 3.5\ H_2O$: | |
|---|---|
| Calcd: | C, 49.97; H, 5.48; N, 13.45; Cl, 17.02; |
| Found: | C, 50.03; H, 4.69; N, 13.33; Cl, 16.92. |
| HPLC Analysis (Method A): | 97.6% $t_r$ = 18.96 min. |

Example 38
1-[4-Methoxybenzoyl-D,L-(pyridin-2-yl)glycinyl]-4-(pyridin-3-ylamino)piperidine.

Prepared from 4-methoxybenzoic acid and 1-[D,L-(pyridin-2-yl)glycinyl]-4-(pyridin-3-ylamino)piperidine using Method 1-A.

1H-NMR
IS-MS, m/e 446.3 (M+1)
HPLC Analysis (Method A): 100% $t_r$=12.07 min.

Example 39
1-(Indole-6-carbonyl-D-phenylglycinyl)-4-(pyridin-2-ylamino)piperidine.

Prepared from indole-6-carboxylic acid and 1-D-phenylglycinyl-4-(pyridin-2-ylamino)piperidine using Method 1-A.
$[\alpha]^{25}{}_D$=−90.7° (c 0.25, methanol)
Melting Point=128–134° C.
$^1$H NMR (CD$_3$OD)
HPLC Analysis (Method A):>95.2% $t_r$=14.7 min
APCI-MS, m/e=454 (M+1)

Example 39a
1-(Indole-6-carbonyl-D-phenylglycinyl)-4-(pyridin-2-ylamino)piperidine Hydrochloride.

1-(Indole-6-carbonyl-D-phenylglycinyl)-4-(pyridin-2-ylamino)piperidine (304 mg, 0.67 mmol) was dissolved in CH$_2$Cl$_2$ (6.5 mL), and the solution was cooled to 0° C. To this solution was added HCl in ether (2 N, 0.34 mL), the mixture was stirred for 20 min, and the solvent was removed under vacuum to give the title compound (295 mg; 90%).
$[\alpha]^{25}{}_D$=−99.0° C. (c 0.25, methanol).
Melting Point=182–185° C. (dec.)
$^1$H NMR (CD$_3$OD).
HPLC Analysis (Method A): 96.7% $t_r$=14.6 min

| Analysis for $C_{27}H_{27}N_5O_2$.1.1 HCl.1.1 H$_2$O: | |
| --- | --- |
| Calcd: | C, 63.16; H, 5.95; N, 13.64; Cl, 7.60; |
| Found: | C, 63.55; H, 5.92; N, 13.24; Cl, 7.50. |

APCI-MS, m/e = 454 (M + 1).

Example 40
1-(Indole-6-carbonyl-D-phenylglycinyl)-4-(pyridin-4-ylamino)piperidine.

Prepared from indole-6-carboxylic acid and 1-D-phenylglycinyl-4-(pyridin-4-ylamino)piperidine using Method 1-A.
Melting Point=154–170° C.
$^1$H NMR (CDCl$_3$)
HPLC Analysis (Method A): 97.2% $t_r$=14.56 min
API-MS, m/e=454 (M+1)

Example 40a
1-(Indole-6-carbonyl-D-phenylglycinyl)-4-(pyridin-4-ylamino)piperidine Hydrochloride.

Using methods substantially equivalent to those described in Example 39a, the title compound was prepared from 1-(indole-6-carbonyl)-D-phenylglycinyl-4-(pyridin-4-ylamino)piperidine (67%).
Melting Point=205–215° C.
$^1$H NMR (CD$_3$OD).
HPLC Analysis (Method A): 98.2% $t_r$=14.6 min
APCI-MS, m/e=454 ($C_{29}H_{28}N_6O_2$+1).
TLC $R_f$=0.44 (100:10:1 CH$_2$Cl$_2$:methanol:concentrated ammonium hydroxide).

Example 41
1-[Indole-6-carbonyl-D,L-(pyridin-2-yl)glycinyl]-4-(pyridin-2-yloxy)piperidine.

Prepared from indole-6-carboxylic acid and 1-(D,L-pyridin-2-yl)glycinyl-4-(pyridin-2-yloxy)piperidine using Method 1-A.

$^1$H NMR
IS-MS, m/e 456.5 (M+1)
HPLC Analysis (Method A): 98.6% $t_r$=18.79 min

Example 42
1-[3-Chloroindole-6-carbonyl-D,L-(pyridin-2-yl)glycinyl]-4-(pyridin-2-yloxy)piperidine.

Prepared from 3-chloroindole-6-carboxylic acid and 1-(D,L-pyridin-2-yl)glycinyl-4-(pyridin-2-yloxy)piperidine using Method 1-A.
$^1$H NMR
IS-MS, m/e=490.2 (M+1)

| Analysis for $C_{26}H_{24}N_5O_3Cl$.0.7 H$_2$O: | |
| --- | --- |
| Calcd: | C, 62.14; H, 5.09; N, 13.94; |
| Found: | C, 62.03; H, 5.13; N, 13.62. |
| HPLC Analysis (Method A): | 96.8% $t_r$ = 25.86 min |

Example 43
1-[3-Methylindole-6-carbonyl-D,L-(pyridin-2-yl)glycinyl]-4-(pyridin-2-yloxy)piperidine.

Prepared from 3-methylindole-6-carboxylic acid and 1-(D,L-pyridin-2-yl)glycinyl-4-(pyridin-2-yloxy)piperidine using Method 1-A.
$^1$H NMR
IS-MS, m/e=470.3 (M+1)

| Analysis for $C_{27}H_{27}N_5O_3$.0.75 H$_2$O: | |
| --- | --- |
| Calcd: | C, 67.13; H, 5.95; N, 14.49; |
| Found: | C, 67.03; H, 5.93; N, 13.88. |
| HPLC Analysis (Method A): | 97.5% $t_r$ = 23.22 min |

Example 44
1-[4-Methoxybenzoyl-D,L-(pyridin-2-yl)glycinyl]-4-(pyridin-2-yloxy)piperidine.

Prepared from 4-methoxybenzoic acid and 1-(D,L-pyridin-2-yl)glycinyl-4-(pyridin-2-yloxy)piperidine using Method 1-A.
$^1$H NMR
IS-MS, m/e=447.5 (M+1)

| Analysis for $C_{25}H_{26}N_4O_4$.0.5 H$_2$O: | |
| --- | --- |
| Calcd: | C, 65.92; H, 5.98; N, 12.30; |
| Found: | C, 65.77; H, 6.08; N, 12.45. |
| HPLC Analysis (Method A): | 95.0% $t_r$ = 17.78 min |

Example 45
1-[3-Chloroindole-6-carbonyl-D,L-(pyridin-2-yl)glycinyl]-4-(pyridin-4-yloxy)piperidine.

Prepared from 3-chloroindole-6-carboxylic acid and 1-(D,L-pyridin-2-yl)glycinyl-4-(pyridin-4-yloxy)piperidine using Method 1-A.

¹H NMR
IS-MS, m/e=490.5 (M+1)

Analysis for $C_{26}H_{24}N_5O_3Cl.1.75\ H_2O$:

| | |
|---|---|
| Calcd: | C, 59.88; H, 5.32; N, 13.43; |
| Found: | C, 60.10; H, 4.94; N, 12.96. |
| HPLC Analysis (Method A): | 98.5% $t_r$ = 20.92 min |

Example 46

1-[3-Methylindole-6-carbonyl-D,L-(pyridin-2-yl)glycinyl]-4-(pyridin-4-yloxy)piperidine.

Prepared from 3-methylindole-6-carboxylic acid and 1-(D,L-pyridin-2-yl)glycinyl-4-(pyridin-4-yloxy)piperidine using Method 1-A.
¹H NMR
IS-MS, m/e=470.5 (M+1)

Analysis for $C_{27}H_{27}N_5O_3.2.5\ H_2O$:

| | |
|---|---|
| Calcd: | C, 63.02; H, 6.27; N, 13.61; |
| Found: | C, 63.33; H, 5.68; N, 13.58. |
| HPLC Analysis (Method A): | 78.4% $t_r$ = 18.18 min |

Example 47

1-[Indole-6-carbonyl-D,L-(pyridin-2-yl)glycinyl]-4-(pyridin-4-yloxy)piperidine.

Prepared from indole-6-carboxylic acid and 1-(D,L-pyridin-2-yl)glycinyl-4-(pyridin-4-yloxy)piperidine using Method 1-A.
¹H NMR
IS-MS, m/e=456.2 (M+1)

Analysis for $C_{26}H_{25}N_5O_3.2.5\ H_2O$:

| | |
|---|---|
| Calcd: | C, 62.39; H, 6.04; N, 13.99; |
| Found: | C, 62.60; H, 5.14; N, 13.38. |
| HPLC Analysis (Method A): | 100% $t_r$ = 15.18 min |

Example 48

1-[4-Methoxybenzoyl-D,L-(pyridin-2-yl)glycinyl]-4-(pyridin-4-yloxy)piperidine.

Prepared from 4-methoxybenzoic acid and 1-(D,L-pyridin-2-yl)glycinyl-4-(pyridin-4-yloxy)piperidine using Method 1-A.
¹H NMR
IS-MS, m/e=447.5 (M+1)

Analysis for $C_{25}H_{26}N_4O_4.1.25\ H_2O$:

| | |
|---|---|
| Calcd: | C, 64.02; H, 6.13; N, 11.95; |
| Found: | C, 64.11; H, 5.60; N, 11.58. |
| HPLC Analysis (Method A): | 98.2% $t_r$ = 13.50 min |

Preparation of Examples 49–54

The following compounds were prepared according to the indicated method (Method 1-A, Method 1-B, Method 1-C or Method 1-D) from the indicated starting materials, unless otherwise described.

Example 49

1-[4-Methoxybenzoyl-D,L-(2-chlorophenyl)glycinyl]-4-(pyridin-4-yloxy)piperidine hydrochloride.

Method 1-C

To a stirring solution of 1-D,L-(2-chlorophenyl)glycinyl)-4-(pyridin-4-yloxy)piperidine (0.374 g, 1.08 mmol) in methylene chloride (5 mL) was added triethylamine (0.17 mL, 1.2 mmol), followed by 4-methoxybenzoyl chloride (0.203 g, 1.2 mmol). After 3 h, an additional 50 mg of 4-methoxybenzoyl chloride was added; and, after another 1 h, the solvent was removed in vacuo, and the residue was dissolved in 1% acetic acid and loaded onto an SCX column. The column was washed with methanol, and then the product was eluted from the column with 30% 2 N ammonia/methanol in methylene chloride. The product containing fractions were combined and concentrated in vacuo. The product was further purified by RP-HPLC (Vydac C18; 15% to 45% B in A over 150 min; A=0.1% HCl in $H_2O$, B=0.1% HCl in $CH_3CN$) to give 76 mg (14%) of the title compound.
¹NMR
IS-MS, m/e 479.9 (M+1)

Analysis for $C_{26}H_{26}N_3O_4Cl.0.9\ HCl.2.0\ H_2O$:

| | |
|---|---|
| Calcd: | C, 56.90; H, 5.68; N, 7.66; Cl, 12.27; |
| Found: | C, 56.99; H, 5.32; N, 7.62; Cl, 12.09. |
| HPLC Analysis (Method A): | 100% $t_r$ = 24.50 min. |

Example 50

1-[Indole-6-carbonyl-D,L-(2-chlorophenyl)glycinyl]-4-(pyridin-4-yloxy)piperidine Hydrochloride.

The free base of the title compound was prepared from 1-(D,L-2-chlorophenyl)glycinyl-4-(pyridin-4-yloxy)piperidine using Method 1-A. The compound was purified by chromatography over silica gel, eluting with a gradient of 0–5% 2 N ammonia/methanol in chloroform (IS-MS, m/e 488.9 (M+1)). The hydrochloride salt was then formed by treatment of the free base in methylene chloride with 1 equivalent of a 1 M solution of hydrochloric acid in diethyl ether. The solvents were removed in vacuo to give the title compound. ¹NMR
IS-MS, m/e 489.0 (M+1)

Analysis for $C_{27}H_{25}N_4O_3Cl.1.1\ HCl.1.0\ H_2O$:

| | |
|---|---|
| Calcd: | C, 59.27; H, 5.18; N, 10.24; Cl, 13.61; |
| Found: | C, 59.45; H, 5.11; N, 10.15; Cl, 14.06. |
| HPLC Analysis (Method A): | 99% $t_r$ = 26.44 min. |

Example 51

1-[Indole-6-carbonyl-D,L-(quinolin-8-yl)glycinyl]-4-(pyridin-4-yloxy)piperidine Hydrochloride.

Prepared from 1-[D,L-(quinolin-8-yl)glycinyl]-4-(pyridin-4-yloxy)piperidine and indole-6-carboxylic acid using Method 1-A, substituting dichloromethane for DMF. The product was purified by preparative RP-HPLC (Vydac $C_{18}$; 15% to 45% B in A over 150 min; A=0.1% HCl in $H_2O$, B=0.1% HCl in $CH_3CN$) to give the title compound.

$^1$NMR
IS-MS, m/e 506.1 (M+1)

| Analysis for C$_{30}$H$_{27}$N$_5$O$_3$.1.25 HCl.2.5 H$_2$O: |
|---|
| Calcd:   C, 60.43; H, 5.62; N, 11.75; Cl, 7.43;<br>Found:   C, 60.47; H, 5.13; N, 11.93; Cl, 7.48.<br>HPLC Analysis (Method A): 99% t$_r$ = 22.40 min. |

Example 52

1-(Indole-6-carbonyl-D-phenylglycinyl)-4-(6-methylpyridin-2-yloxy)piperidine Hydrochloride.

Prepared from indole-6-carboxylic acid and 1-(D-phenylglycinyl)-4-(6-methylpyridin-2-yloxy)piperidine using Method 1-A. The free base was purified using preparative thin layer chromatography, eluting with 5% 2 N ammonia/methanol in dichloromethane. The free base was then dissolved in dichloromethane, 1 equivalent of HCl (1 M HCl in diethyl ether) was added and the solvents were removed in vacuo to give the title compound.

$^1$NMR
IS-MS, m/e 469.0 (M+1)

| Analysis for C$_{28}$H$_{28}$N$_4$O$_3$.1.05 HCl.0.75 H$_2$O: |
|---|
| Calcd:   C, 64.63; H, 5.92; N, 10.77; Cl, 7.16;<br>Found:   C, 64.50; H, 6.19; N, 10.53; Cl, 7.25.<br>HPLC Analysis (Method A): 98.5% t$_r$ = 25.36 min. |

Example 53

1-(Indole-6-carbonyl-D-phenylglycinyl)-4-(2-cyanopyridin-4-yloxy)piperidine Hydrochloride.

Method 1-D

To a stirring solution of 1-D-phenylglycinyl-4-(2-cyanopyridin-4-yloxy)piperidine (0.2 g, 0.594 mmol) in dichloromethane (5 mL) was added indole-6-carboxylic acid (0.106 g, 0.654 mmol), followed by a few drops of DMF. After the solution clarified, the solution was cooled to 0° C. and DECP (0.099 mL, 0.654 mmol) was added dropwise. After stirring overnight, the solvent was removed in vacuo and the residue was dissolved in dichlormethane and washed with brine.

The organic phase was then dried with Na$_2$SO$_4$, filtered and concentrated in vacuo. The residue was then dissolved in a minimal amount of dichloromethane and chromatographed over silica gel, eluting with a gradient of 50–100% ethyl acetate in hexanes. The product containing fractions were combined and concentrated to give 0.091 g (32%) of the title compound.

$^1$NMR
IS-MS, m/e 478.0 (M−1)
HPLC Analysis (Method A): 95% t$_r$=35.07 min.

Example 54

1-[4-Methoxybenzoyl-D,L-(2-aminothiazol-4-yl)glycinyl]-4-(pyridin-4-yloxy)piperidine Dihydrochloride.

To a stirred solution of 4-methoxybenzoic acid (761 mg, 5.0 mmol), 1-(D,L-2-aminothiazol-4-ylglycinyl)-4-(pyridin-4-yloxy)piperidine (circa 5.0 mmol) and HOAt (750 mg, 5.5 mmol) in DMF (40 mL) was added EDCI (1.05 g, 5.5 mmol). The mixture was stirred at room temperature overnight and the solvent removed in vacuo. The residues taken up in chloroform: isopropyl alcohol (2:1) and washed with satd sodium bicarbonate. The aqueous phase was back extracted with chloroform: isopropyl alcohol (2:1) (×3) and the combined organic extracts were dried (MgSO$_4$) and concentrated in vacuo.

Half of the crude product was purified by preparative RPHPLC and the product fractions concentrated, taken up in chloroform: isopropyl alcohol (2:1), washed with satd sodium bicarbonate, dried (MgSO$_4$) and concentrated in vacuo. The free base thus obtained was dissolved in methanol and treated with 2 equivalents of HCl in ether and evaporated to dryness.

The residue was dissolved in water/acetonitrile and freeze dried. Yield 466 mg.

$^1$NMR
LCMS, m/e 467 (M+1)

The following compounds are prepared using similar procedures to those described above but using a starting material such as Boc-D-(2-chlorophenyl)glycine:

1-[Indole-6-carbonyl-D-(2-chlorophenyl)glycinyl]-4-(pyridin-4-ylamino)piperidine.
1-[Indole-6-carbonyl-D-(2-chlorophenyl)glycinyl]-4-(pyridin-2-ylamino)piperidine.

Assay Protocols

Enzyme Inhibition assays:

The ability of a test compound to inhibit factor Xa may be evaluated in one or more of the following Enzyme Inhibition assays, or in other standard assays known to those skilled in the art.

Enzyme Inhibition Assay 1

Enzyme assays were carried out at room temperature in 0.1M phosphate buffer, pH7.4 according to the method of Tapparelli et al (J. Biol. Chem. 1993,268,4734–4741). Purified human factor Xa, trypsin, thrombin and plasmin were purchased from Alexis Corporation, Nottingham, UK. Urokinase was purchased from Calbiochem, Nottingham, UK. Chromogenic substrates for these enzymes; pefachrome-FXA, pefachrome-TRY, pefachrome-TH, pefachrome-PL and pefachrome-UK were purchased from Pentapharm AG, Basel, Switzerland. Product (p-nitroaniline) was quantified by adsorption at 405 nm in 96 well microplates using a Dynatech MR5000 reader (Dynex Ltd, Billingshurst, UK). Km and Ki were calculated using SAS PROC NLIN (SAS Institute, Cary, N.C., USA, Release 6.11) K$_m$ values were determined as 100.9 μM for factor Xa/pefachrome-FXA and 81.6 μM for trypsin/pefachrome-TRY. Inhibitor stock solutions were prepared at 40 mM in Me2SO and tested at 500 μM, 50 μM and 5 μM. Accuracy of Ki measurements was confirmed by comparison with Ki values of known inhibitors of factor Xa and trypsin.

In agreement with published data, benzamidine inhibited factor Xa, trypsin, thrombin, plasmin and urokinase with Ki values of 155 μM, 21 μM, 330 nM, 200 nM and 100 nM respectively. NAPAP inhibited thrombin with a Ki value of 3 nM. Compounds of the invention were found to have activity in these assays.

Enzyme Inhibition Assay 2

Human factor Xa and human thrombin were purchased from Enzyme Research Laboratories (South Bend, Ind., USA). Other proteases were from other commercial sources. Chromogenic para-nitroanilide peptide protease substrates were purchased from Midwest Biotech (Fishers, Ind., USA).

The binding affinities for human factor Xa were measured as apparent association constants (Kass) derived from protease inhibition kinetics as described previously.[a,b,c,d] The apparent Kass values were obtained using automated (BioMek-1000) dilutions of inhibitors (Kass determinations are performed in triplicate at each of four-eight inhibitor concentrations) into 96-well plates and chromogenic substrate hydrolysis rates determined at 405 nm using a Thermomax plate reader from Molecular Devices (San Francisco). For factor Xa inhibition, the assay protocol was: 50 µl buffer (0.06 M tris, 0.3 M NaCl, pH 7.4); 25 µl inhibitor test solution (in MeOH); 25 µl human factor Xa (32 nM in 0.03 M tris, 0.15 M NaCl, 1 mg/ml HSA); finally, 150 µl BzIleGluGlyArgpNA (0.3 mM in water) added within 2 min to start hydrolysis. Final factor Xa was 3.2 nM. Free [Xa] and bound [Xa] were determined from linear standard curves on the same plate by use of SoftmaxPro software for each inhibitor concentration and apparent Kass calculated for each inhibitor concentration which produced hydrolysis inhibition between 20% and 80% of the control (3.2 nM factor Xa): apparent Kass=$[E:I]/[E_f][I_f]=[E_b]/[E_f][I°-I_b]$. The apparent Kass values so obtained are approximately the inverse of the Ki for the respective inhibitors [1/appKass= app Ki]. The variability of mean apparent Kass values determined at the single substrate concentration was +/−15%. The assay system Km was measured as 0.347+/−0.031 mM [n=4]; and Vmax was 13.11+/−0.76 µM/min.

Kass values were determined with thrombin and other proteases using the same protocol with the following enzyme and substrate concentrations: thrombin 5.9 nM with 0.2 mM BzPheValArgpNA; XIa 1.2 nM with 0.4 mM pyroGluProArgpNA; XIIa 10 nM with 0.2 mM HDProPheArgpNA; plasmin 3.4 nM with 0.5 mM HDValLeu-LyspNA; nt-PA 1.2 nM with 0.8 mM HDIleProArgpNA; and rokinase 0.4 nM with 0.4 mM pyroGluGlyArgpNA; aPC 3 nM with 0.174 mM pyroGluProArgpNA; plasma kallikrein 1.9 nM with D-ProPheArgpNA; bovine trypsin 1.4 nM with 0.18 mM BzPheValArgpNA.

Citations (a) Sall D J, J A Bastian, S L Briggs, J A Buben, N Y Chirgadze, D K Clawson, M L Denny, D D Giera, D S Gifford-Moore, R W Harper, K L Hauser, V J Klimkowski, T J Kohn, H-S Lin, J R McCowan, A D Palkowitz, G F Smith, M E Richett, K Takeuchi, K J Thrasher, J M Tinsley, B G Utterback, S-C B Yan, M Zhang. Dibasic Benzo[b]thiophenes Derivatives as a Novel Class of Active Site Directed Thrombin Inhibitors. 1. Determination of the Serine Protease Selectivity, Structure-Activity Relationships and Binding Orientation. J Med Chem 40 3489–3493 (1997).

(b) Smith G F, T J Craft, D S Gifford-Moore, W J Coffman, K D Kurz, E Roberts, R T Shuman, G E Sandusky, N D Jones, N Chirgadze, and C V Jackson. A Family of Arginal Thrombin Inhibitors Related to Efegatran. Sem. Thrombos. Hemost. 22, 173–183 (1996).

(c) Smith G F, D S Gifford-Moore, T J Craft, N Chirgadze, K J Ruterbories, T D Lindstrom, J H Satterwhite. Efegatran: A New Cardiovascular Anticoagulant. In New Anticoagulants for the Cardiovascular Patient. Ed. R Pifarre. Hanley & Belfus, Inc., Philadelphia (1997) pp 265–300.

(d) Sall D J, J A Bastian, N Y Chirgadze, M L Denny, M J Fisher, D S Gifford-Moore, R W Harper, V J Klimkowski, T J Kohn, H S Lin, J R McCowan, M E Richett, G F Smith, K Takeuchi, J E Toth, M Zhang. Diamino Benzo[b]thiophene Derivatives as a Novel Class of Active Site Directed Thrombin Inhibitors: 5. Potency, Efficacy and Pharmacokinetic Properties of Modified C-3 Side Chain Derivatives. In press, J Med Chem (1999).

In general, the compounds of formula (I) exemplified herein have been found to exhibit a Ki of 10 µM or less in Assay 1 and/or a Kass of at least $0.1\times10^6$ L/mole in Assay 2.

The ability of a test compound to elongate Partial Thromboplastin Time (Prothrombin Time) may be evaluated in the following test protocols.

Partial Thromboplastin Time (Prothrombin) Test Protocol

Venous blood was collected into 3.2% (0.109 m) trisodium citrate vacutainer tubes at 1 volume of anticoagulant to nine volumes of blood. The blood cells were separated by centrifugation at 700 g for ten minutes to yield plasma, which was frozen at 70° C. until required.

To perform the test, 100 µl of plasma was pipetted into in a glass test tube, 1 µl of test compound in DMSO was added, and allowed to warm to 37° over two minutes. 100 µl of warm (37°) Manchester (tissue thromboplasin) reagent (Helena Biosciences, UK) was added, allowed to equilibrate for two minutes. 100 µl of warm (37°) 25 mM calcium chloride solution was added to initiate clotting. The test tube was tilted three times through a 90° angle every five seconds to mix the reagents and the time to clot formation recorded. Data from a series of observations and test compound concentrations are analysed by a SAS statistical analysis program and a CT2 (Concentration required to double clotting time) for each compound is generated.

Compounds of the invention were found to significantly elongate the partial thromboplastin time (Prothrombin time).

Alternative Prothrombin Time and APTT Protocols

Coagulation Determinations. Prothrombin Times and APTT values were determined in HUMAN PLASMA with a STA instrument (Stago). BioPT is a special non-plasma clotting assay triggered with human tissue factor (Innovin). Possible binding to albumen or to lipid was assessed by comparing the BioPT effects in the presence/absence of 30 mg/ml human albumen (HSA) and 1 mg/ml phosphatidyl choline (PC). Inhibitors were delivered in 50% MeOH vehicle.

APTT ASSAY

75 µl plasma Citrol Baxter-Dade Citrated Normal Human Plasma

25 µl test sol'n

75 µl Actin Baxter-Dade Activated Cephaloplastin incubate 2 min min. @ 37°

75 µl CaCl$_2$ (0.02 M)

PT ASSAY

75 µl plasma

25 µl test sol'n

75 µl saline incubate 1 min. @ 37° C.

75 µl Innovin Baxter-Dade Recombinant Human Tissue Factor

Compounds of the invention were found to be potent inhibitors of factor Xa.

What is claimed is:

1. A serine protease inhibitor compound of formula (I)

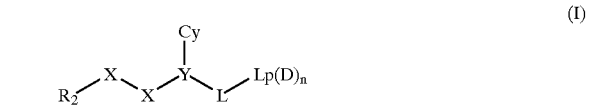

wherein:

R$_2$ is a 5 or 6 membered aromatic carbon ring optionally interrupted by a nitrogen, oxygen or sulphur ring atom, optionally being substituted in the 3 and/or 4 position (in relation to the point of attachment of X—X) by halo, nitro, thiol, haloalkoxy, hydrazido, alkylhydrazido, amino, cyano, haloalkyl, alkylthio, alkenyl, alkynyl, acylamino, tri or difluoromethoxy, carboxy, acyloxy, MeSO$_2$— or R$_1$, or the substituents at the 3 and 4 positions taken together form a fused ring which is a 5 or 6 membered carbocyclic or heterocyclic ring optionally substituted by halo, haloalkoxy, haloalkyl, cyano, nitro, amino, hydrazido, alkyithio, alkenyl, alkynyl or $R_{ij}$, and optionally substituted in the position alpha to the X—X group (i.e. 6 position for a six membered aromatic ring etc) by amino, hydroxy, halo, alkyl, carboxy, alkoxycarbonyl, cyano, amido, aminoalkyl, alkoxy or alkylthio with the proviso that $R_2$ cannot be aminoisoquinolyl;

each X independantly is a C, N, O or S atom or a CO, $CR_{1a}$, $C(R_{1a})_2$ or $NR_{1a}$ group, at least one X being C, CO, $CR_{1a}$ or $C(R_{1a})_2$;

each $R_{1a}$ independently represents hydrogen, hydroxyl, alkoxy, alkyl, aminoalkyl, hydroxyalkyl, alkoxyalkyl, alkoxycarbonyl, alkylaminocarbonyl, alkoxycarbonylamino, acyloxymethoxycarbonyl or alkylamino optionally substituted by hydroxy, alkylamino, alkoxy, oxo, aryl or cycloalkyl;

$R_1$ is as defined for $R_{1a}$, provided that $R_1$ is not unsubstituted aminoalkyl;

Y (the α-atom) is a nitrogen atom or a $CR_{1b}$ group;

Cy is a saturated or unsaturated, mono or poly cyclic, homo or heterocyclic group, optionally substituted by groups $R_{3a}$ or $R_{3i}X_i$;

each $R_{3a}$ independently is $R_{1c}$, amino, halo, cyano, nitro, thiol, alkylthio, alkylsulphonyl, alkylsulphenyl, triazolyl, imidazolyl, tetrazolyl, hydrazido, alkylimdazolyl, thiazolyl, alkylthiazolyl, alkyloxazolyl, oxazolyl, alkylsulphonamido, alkylaminosulphonyl, aminosulphonyl, haloalkoxy, haloalkyl, a group of the formula —$C(X^3)N(R_{11})R_{12}$ (wherein $X^3$ is O or S; and $R^{11}$ an $R^{12}$ are independantly selected from hydrogen, methyl or ethyl or together with the nitrogen atom to which they are attached form a pyrrolidin-1-yl, piperdin-1-yl or morpholino group), or —$OCH_2O$— which is bonded to two adjacent ring atoms in Cy;

$X_1$ is a bond, O, Nh or $CH_2$;

$R_{3i}$ is phenyl, pyridyl or pyrimidinyl optionally substtuted by $R_{3a}$; and $R_{1b}$, $R_{1c}$ and $R_{1j}$ are as defined for $R_{1a}$, L is CO; and -Lp(D)$_n$ is of the formula:

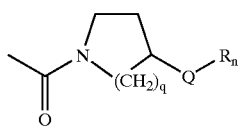

wherein:

q is 2;

Q is —O— or —NH—;

and $R_q$ is $R_c$ which is pyridyl, pyrimidin-4-yl, pyridazin-3-yl, pyridazin-4-yl or phenyl (which phenyl or pyridyl group may bear a fluoro, chloro, alkyl, $CONH_2$, $SO_2NH_2$, dialkylaminosulphonyl, methoxy, methylthio, alkylsulphonyl, alkylaminosulphonyl, alkylaminocarbonyl, amino, alkoxycarbonyl, acetylamino, cyano, ethoxy, nitro, hydroxy, alkylsulphonylamino, triazolyl or tetrazolyl substituent);

or a physiologically-tolerable salt thereof.

2. A serine protease inhibitor compound according to claim 1 wherein:

$R_2$ is a 5 or 6 membered aromatic carbon ring optionally interrupted by a nitrogen, oxygen or sulphur ring atom, optionally being substituted in the 3 and/or 4 position (in relation to the point of attachment of X—X) by halo, nitro, thiol, haloalkoxy, hydrazido, alkylhydrazido, amino, cyano, haloalkyl, alkyithio, alkyenyl, alkynyl, acylamino, tri or difluoromethoxy, carboxy, acyloxy, $MeSO_2$— or $R_1$, or the substituents at the 3 and 4 positions, taken together form a fused ring which is a 5 or 6 membered carbocyclic or heterocyclic ring optionally substituted by halo, haloalkoxy, haloalkyl, cyano, nitro, amino, hydrazido, alkythio, alkenyl, alkynyl or $R_{1j}$, and optionally substituted in the position alpha to the X—X group (i.e. 6 position for a six membered aromatic ring etc) by amino, hydroxy, halo, alkyl, carboxy, alkoxycarbonyl, cyano, amido, aminoalkyl, alkoxy or alkylthio with the proviso that $R_2$ cannot be aminosoquinolyl;

each X independently in a C, N, O or S atom or a CO, $CR_{1a}$, $C(R_{1a})_2$ or $NR_{1a}$ group, at least one X being C, CO, $CR_{1a}$ or $C(R_{1a})_2$;

each $R_{1a}$ independently represents hydrogen, hydroxyl, alkoxy, alkyl, aminoalkyl, hydroxyalkyl, alkoxyalkyl, alkoxycarbonyl, alkylaminocarbonyl, alkoxycarbonylamino, acyloxymethoxycarbonyl or alkylamino optionally substituted by hydroxy, alkylamino, alkoxy, oxo, aryl or cycloalkyl;

$R_1$ is as defined for $R_{1a}$, provided that $R_1$ is not unsubstituted aminoalkyl;

Y (the α-atom) is a nitrogen atom or a $CR_{1b}$ group;

Cy is a saturated or unsaturated, mono or poly cyclic, homo or heterocyclic group, preferably containing 5 to 10 ring atoms and optionally substituted by groups $R_{3a}$ or phenyl optionally substituted by $R_{3a}$;

each $R_{3a}$ independently is $R_{1c}$, amino, halo, cyano, nitro, thiol, alkylthio, alkylsulphonyl, alkylsulphenyl, triazolyl, imidazolyl, tetrazolyl, hydrazido, alkyl imdazolyl, thiazolyl, alkyl thiazolyl, alkyl oxazolyl, oxazolyl, alkylsulphonamido, alkylaminosulphonyl, aminosulphonyl, haloalkoxy, haloalkyl; and $R_{1b}$, $R_{1c}$ and $R_{1j}$ are as defined for $R_{1a}$, L is CO; and -Lp(D)$_n$ is of the formula:

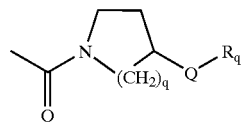

wherein:

q is 2;

Q is —O— or —NH—;

and $R_q$ is $R_c$ which is pyridyl, or phenyl (which phenyl may bear a fluoro, chloro, alkyl, $CONH_2$, $SO_2NH_2$, methylaminosulphonyl, dimethylaminosulphonyl, methylsulphonylamino, methoxy or methylsulphonyl substituent);

or a physiologically-tolerable salt thereof.

3. A compound according to claim 2 wherein -Lp(D)n is selected from the following formulae:

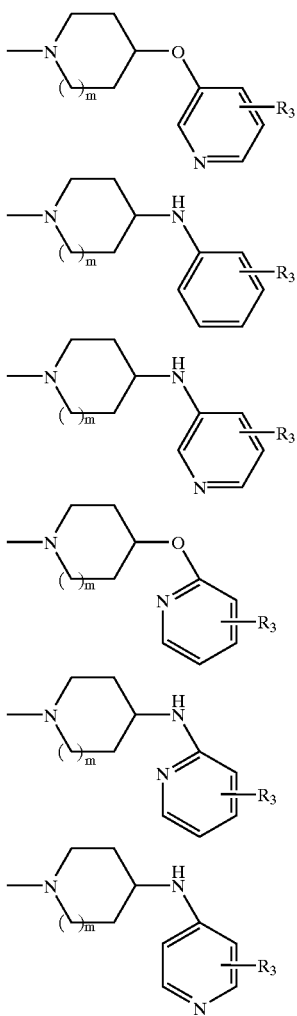

wherein:

m represents 1; and when R$_3$ is present as a substituent on an aromatic ring, it is selected from hydrogen, alkylsulphonyl, aminosulphonyl, alkylaminosulphonyl, alkylaminocarbonyl, amino, amido, alkoxycarbonyl, acetylamino, chloro, fluoro, cyano, methoxy, ethoxy, nitro, hydroxy, alkylsulphonylamino, triazolyl and tetrazolyl.

4. A compound according to claim 2 wherein -Lp(D)n is selected from the following formulae:

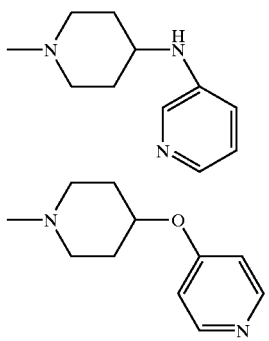

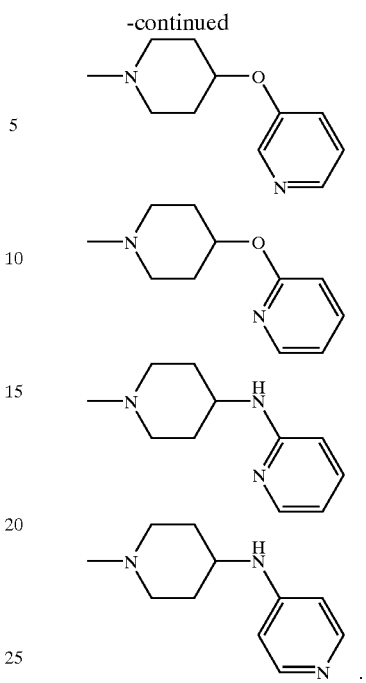

5. A compound according to claim 1, wherein Q is —NH—.

6. A compound according to claim 1 wherein Rc is pyrid-2-yl, pyrid-3-yl, pyrid-4-yl, pyridazin-3-yl, pyridazin-4-yl, pyrimid-4-yl or phenyl.

7. A compound according to claim 1, wherein Rc is phenyl, 2-fluorophenyl, 3-fluorophenyl, 4-fluorophenyl, 3-methoxyphenyl, 4-methoxyphenyl, 2-methylsulfonylphenyl, 2-methylthiophenyl, pyrid-2-yl, pyrid-3-yl or pyrid-4-yl.

8. A compound according to claim 1 wherein R$_2$ is phenyl, thien-2-yl, naphthyl, indol-2-yl, indol-6-yl, benzo[b]furan-5-yl, benzo[b]thiophen-2-yl or benzimidazol-2-yl (each of which is optionally substituted as defined in claim 1).

9. A compound according to claim 1 wherein optional substituents for R$_2$ are selected from: fluoro, chloro, bromo, iodo, nitro, thiol, difluoromethoxy, trifluoromethoxy, hydrazido, methylhydrazido, amino, cyano, trifluoromethyl, methylthio, vinyl, ethynyl, acetylamino, carboxy, acetoxy, hydroxy, methyl, ethyl, amido (CONH$_2$), aminomethyl, methoxy and ethoxy.

10. A compound according to claim 1 wherein R$_2$ is selected from one of the formula (A') to (H'):

(A')

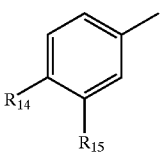

(B')

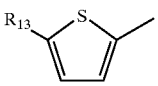

(C')

-continued

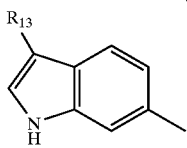
(D')

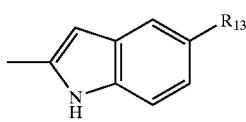
(E')

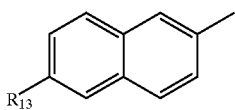
(F')

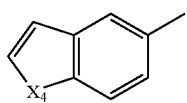
(G')

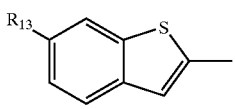
(H')

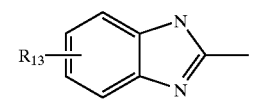

wherein X₄ is O or S, R₁₃ is selected from hydrogen, chloro or methyl and R₁₄ is selected from hydrogen, methyl, ethyl, fluoro, chloro, and methoxy and R₁₅ is selected from hydrogen, methyl, fluoro, chloro and amino.

11. A compound according to claim 10, wherein R₂ is 4-methoxyphenyl, 5-chloroindol-2-yl, 3-chloroindol-6-yl, indol-6-yl, or 3-methylindol-6-yl.

12. A compound according to claim 1 wherein —X—X— is —CONH—.

13. A compound according to claim 1 wherein Cy is an optionally $R_{3a}$ substituted: phenyl, pyridyl, thienyl, thiazolyl, napthyl, piperdinyl, furanyl, pyrrolyl, isoxazolyl, isothiazolyl, pyrazolyl, oxzolyl, imidazolyl, 1,2,4-thiadiazolyl, 1,3,4-thiadiazolyl, pyrimidinyl, pyridazinyl, quinolyl, isoquinolyl, benzofuryl, benzothienyl or cycloalkyl group, or a phonyl group substituted by $R_{3i}X_i$ in which $X_i$ is a bond, O, NH or CH₂ and $R_{3i}$ is phenyl or pyridyl optionally substituted by $R_{3a}$.

14. A compound according to claim 2, wherein Cy is an optionally $R_{3a}$ substituted: phenyl, pyridyl, thienyl, thiazolyl, napthyl, piperidinyl or cycloalkyl group.

15. A compound according to claim 1 wherein $R_{3a}$ is selected from hydrogen, hydroxyl, methoxy ethoxy, methyl, ethyl, methylaminomethyl, dimethylaminomethyl, hydroxymethyl, carboxy, methoxymethyl, methoxycarbonyl, ethoxycarbonyl, methylaminocarbonyl, dimethylaminocarbonyl, aminomethyl, COHN₂, CH₂CONH₂, acetylamino, methoxycarbonylamino, ethoxycarbonylamino, t-butoxycarbonylamino, amino, fluoro, chloro, bromo, cyano, nitro, thiol, methylthio, methylsulphonyl, ethylsulphonyl, methylsulphenyl, methylsulphonylamido, ethylsulphonylamido, methylaminosulphonyl, ethylaminosulphonyl, aminosulphonyl, trifluoromethoxy, trifluoromethyl, bromo, pyrrolidin-1-ylcarbonyl, piperidin-1-ylcarbonyl, morpholin-1-ylcarbonyl and —OCH₂O— (which is bonded to two adjacent ring atoms in Cy).

16. A compound according to claim 2 wherein $R_{3a}$ is selected from hydrogen, hydroxyl, methoxy, ethoxy, methyl, ethyl, methylaminomethyl, dimethylaminomethyl, hydroxymethyl, carboxy, methoxymethyl, methoxycarbonyl, ethoxycarbonyl, methylaminocarbonyl, dimethylaminocarbonyl, aminomethyl, COHN₂, CH₂CONH₂, acetylamino, methoxycarbonylamino, ethoxycarbonylamino, t-butoxycarbonylamino, amino, fluoro, chloro, bromo, cyano, nitro, thiol, methylthio, methylsulphonyl, ethylsulphonyl, methylsulphenyl, methylsulphonylamido, ethylsulphonylamido, methylaminosulphonyl, ethylaminosulphonyl, aminosulphonyl, trifluoromethoxy, trifluoromethyl.

17. A compound according to claim 1 wherein Cy is selected from:

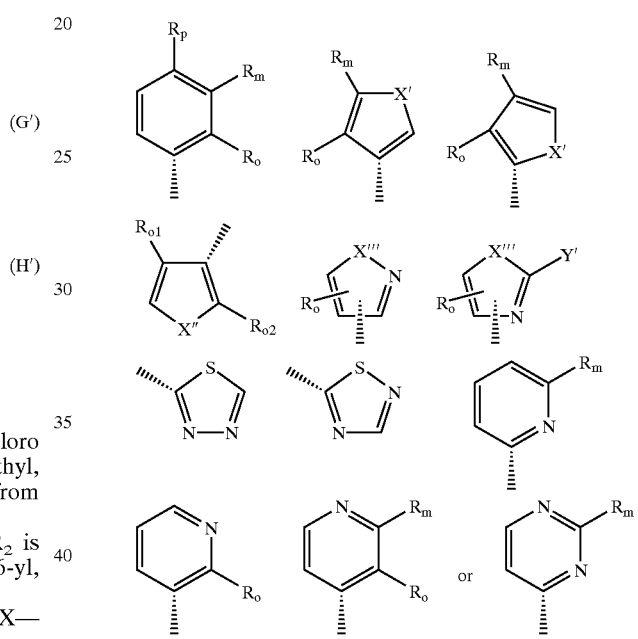

wherein:
X' is selected from O, S and NMe;
X" is selected from O and S;
X'" is selected from O, S, NH and NMe;
Y' is selected from hydrogen, amino, and methyl;
$R_o$ is selected from hydrogen, methyl, fluoro, chloro, trifluoromethyl, methoxy, methylthio, methylsulphinyl and methylsulphonyl;
$R_m$ is selected from hydrogen, methyl, fluoro, chloro, trifluoromethyl, methoxy, methylthio, methylsulphinyl, methylsulphonyl, carboxy, methoxycarbonyl and a group of the formula —C(X³)N(R₁₁)R₁₂ (wherein X³ is O or S, and R₁₁ and R₁₂ are independently selected from hydrogen, methyl or ethyl or together with the nitrogen atom to which they are attached form a pyrrolidin-1-yl, piperidin-1-yl, or morpholino group);
$R_p$ is selected from hydrogen and fluoro; or
$R_o$ and $R_m$ or $R_m$ and $R_p$ form an —OCH2O— group; or
$R_o$ and $R_m$ together with the ring to which they are attached form a 5 or 6 membered aryl or heteroaryl ring (wherein the heteroary ring contains 1 or 2 heteroatoms selected from nitrogen, oxygen and sulfur); and one of $R_{o1}$ and $R_{o2}$ is hydrogen and the other is $R_o$.

18. A compound according to claim 1 wherein Cy is selected from phenyl, 2-chlorophenyl, 2-methoxyphenyl, 4-carbamoylphenyl, pyrid-2-yl, pyrid-3-yl, pyrid-4-yl, thien-2-yl, thien-3-yl, furan-2-yl, furan-3-yl, imidazol-2-yl, thiazol-2-yl, thiazol-4-yl, 2-amino-thiazol-4-yl, thiazol-5-yl, naph-1-thyl, isoquinolin-5-yl, isoquinolin-8-yl, quinolin-4-yl, quinolin-5-yl and quinolin-8-yl.

19. A compound according to any one of claims 1 to 18 wherein Y is CH.

20. A compound as claimed in claim 1, which is selected from 1-(indol-6-carbonyl-D-phenylglycinyl)-4-(4-pyridoxy)piperidine; 1-[indole-6-carbonyl-D,L-(2-chlorophenyl)glycinyl]-4-(pyridin-4-yloxy)piperidine, and physiologically-tolerable salts thereof.

21. A compound according to claim 19, in which the alpha atom in Y is carbon and has the conformation that would result from construction from D-α-aminoacid $NH_2$—$CR_{1b}$(Cy)-COOH where the $NH_2$ represents part of X—X.

22. A compound as claimed in claim 1, in which $R_2$ is selected from one of the formula (A') to (H'):

(A')

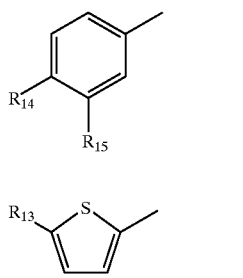

(B')

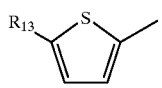

(C')

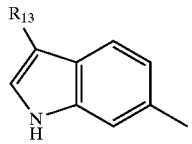

(D')

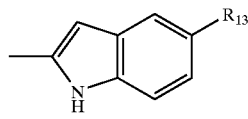

(E')

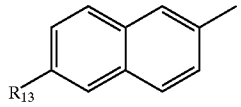

(F')

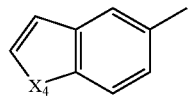

(G')

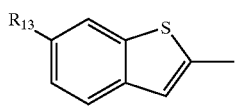

(H')

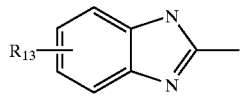

wherein $X_4$ is O or S, $R_{13}$ is selected from hydrogen, chloro or methyl and $R_{14}$ is selected from hydrogen, methyl, ethyl, fluoro, chloro, and methoxy and $R_{15}$ is selected from hydrogen, methyl, fluoro, chloro, and amino;

—X—X— is —CONH—;

Y is CH and has the conformation that would result from construction from a D-α-aminoacid $NH_2$—$CR_{1b}$(Cy)-COOH where the $NH_2$ represents part of X—X; and Cy is selected from:

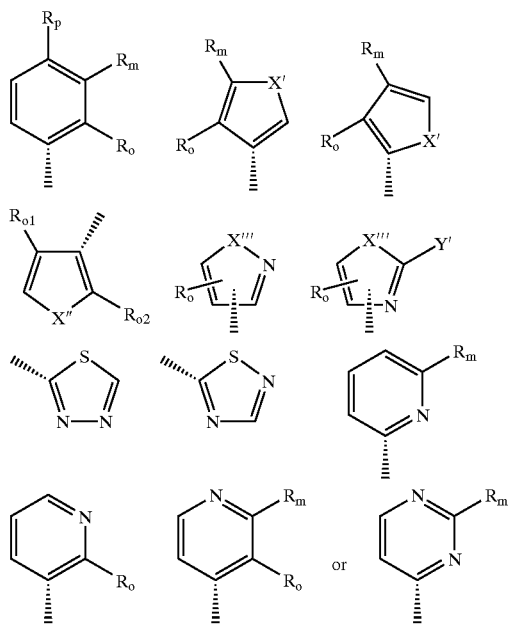

wherein:

X' is selected from O, S, and NMe;

X" is selected from O and S;

X'" is selected from O, S, NH and NMe;

Y' is selected from hydrogen, amino, and methyl;

$R_o$ is selected from hydrogen, methyl, fluoro, chloro, trifluoromethyl, methoxy, methylthio, methylsulphinyl and methylsulphonyl;

$R_m$ is selected from hydrogen, methyl, fluoro, chloro, trifluoromethyl, methoxy, methylthio, methylsulphinyl, methylsulphonyl, carboxy, methoxycarbonyl and a group of the formula —$C(X^3)N(R_{11})R_{12}$ (wherein $X^3$ is O or S, and $R_{11}$ and $R_{12}$ are independently selected from hydrogen, methyl or ethyl or together with the nitrogen atom to which they are attached form a pyrrolidin-1-yl, piperidin-1-yl, or morpholino group);

$R_p$ is selected from hydrogen and fluoro; or $R_o$ and $R_m$ or $R_m$ and $R_p$ form an —OCH2O— group; or $R_o$ and $R_m$ together with the ring to which they are attached form a 5 or 6 membered aryl or heteroaryl ring (wherein the heteroary ring contains 1 or 2 heteroatoms selected from nitrogen, oxygen and sulfur); and one of $R_{o1}$ and $R_{o2}$ is hydrogen and the other is $R_o$.

23. A compound according to claim 22, in which

R₂ is 4-methoxyphenyl, 5-chloroindol-2-yl, 3-chloroindol-6-yl, indol-6-yl, 3-methylindol-6-yl;

Cy is selected from phenyl, 2-chlorophenyl, 2-methoxyphenyl, 4-carbamoylphenyl, pyrid-2-yl, pyrid-3-yl, pyrid-4-yl, thien-2-yl, thien-3-yl, furan-2-yl, furan-3-yl, imidazol-2-yl, thiazol-2-yl, thiazol-4-yl, 2-amino-thiazol-4-yl, thizol-5-yl, naph-1-thyl, isoquinolin-5-yl, isoquinolin-8-yl, quinolin-4-yl, quinolin-5-yl, and quinolin-8-yl; and R_c is phenyl, 2-fluorophenyl, 3-fluorophenyl, 4-fluorophenyl, 3-methoxyphenyl, 4-methoxyphenyl, 2-methylsulfonylphenyl, 2-methylthiophenyl, pyrid-2-yl, pyrid-3-yl or pyrid-4-yl.

24. A compound according to claim 2, in which

R₂ represents:

(i) phenyl optionally being substituted in the 3 and/or 4 position by fluoro, chloro, bromo, iodo, nitro, difluoromethoxy, trifluoromethoxy, amino, cyano, trifluoromethyl, methylthio, vinyl, carboxy, acetoxy, MeSO₂—, hydroxy, methoxy, ethoxy, methyl, methoxycarbonyl, methylamino, ethylamino or amido, and optionally substituted at the 6 position by amino, hydroxy, fluoro, methoxycarbonyl, cyano or aminomethyl;

(ii) naphth-2-yl, optionally substituted at the 6, position by hydroxy and optionally substituted at the 3 position by amino or hydroxy;

(iii) isoquinolin-7-yl, indol-5yl, indol-6-yl, indazol-5-yl, indazol-6-yl, benzothiazol-6-yl, or benzisoxazol-5-yl optionally substituted at the 3 position by chloro, bromo, amino, methyl or methoxy;

(iv) benzimidazol-5-yl or benzothiozol-6-yl optionally substituted at the 2 position by amino;

(v) thien-2-yl or thien-3-yl optionally substituted at the 4 or 5 position by methylthio, methyl or acetyl;

(vi) 3,4-methylenedioxyphenyl, 2,3-dihydroindol-6-yl, 3,3-dichloro-2-oxo-indol-6-yl or 1-methyl-3-aminoindazol-5-yl;

(vii) benzothiazol-2-yl, imidazo[1,2-a]pyrimidin-2-yl or tetrahydroimidazo[1,2-a]pyrimidin-2-yl;

(viii) pyrazol-2-yl substituted at the 5 position by methyl;

(ix) pyrid-2-yl optionally substituted at the 6 position by chloro;

(x) pyrid-3-yl optionally substituted at the 4 position by chloro;

(xi) benzofur-2-yl optionally substituted at the 3 position by chloro, methyl or methoxy, at the 5 or 6 position by methyl and at the 6 position by methoxy;

(xii) indol-2-yl, optionally substituted on the indole nitrogen atom by methyl and optionally substituted at the 5 or 6 position by fluoro, chloro, bromo, methyl or methoxy;

(xiii) indol-6-yl substituted at the 5 position by chloro, fluoro or hydroxy and optionally substituted at the 3 position by chloro or methyl; or (xiv) benzo[b]thiophen-2-yl optionally substituted at the 3 position by fluoro, chloro or methyl, and optionally substituted at the 5 or 6 position by fluoro, chloro, methyl, hydroxy, or methoxy;

—X—X— is —CONH—;

Y is CH and has the conformation that would result from construction from a D-α-aminoacid NH₂—CR_{1b}(Cy)-COOH where the NH₂ represents part of X—X; and Cy is selected from phenyl, 4-aminophenyl, 4-amidophenyl, 4-(N-methyl)amidophenyl, 4-(N,N-dimethyl)amidophenyl, 2-chlorophenyl, 2-methylphenyl, 2-fluorophenyl, 3-fluorophenyl, 4-fluorophenyl, 4-hydroxyphenyl, 2-methoxyphenyl, 4-methoxyphenyl, 4-carboxyphenyl, 3,-ethylsulphonylaminophenyl, thien-2-yl, thien-3-yl, thiazol-4-yl, thiazol-5-yl, 2-methylthiazol-4-yl, pyrid-2-yl, pyrid-3-yl, pyrid-4-yl, piperidin-4-yl, 1-methylpiperidin-4-yl, cyclohexyl and naphth-1-yl.

25. A compound according to claim 24, in which -Lp(D)n is selected from the following formulae:

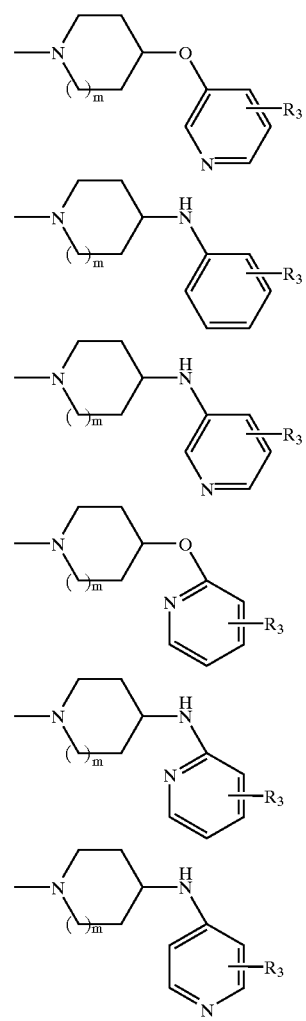

wherein:

m represents 1; and when R₃ is present as a substituent on an aromatic ring, it is selected from hydrogen, alkylsulphonyl, aminosulphonyl, alkylaminosulphonyl, alkylaminocarbonyl, amino, amido, alkoxycarbonyl, acetylamino, chloro, fluoro, cyano, methoxy, ethoxy, nitro, hydroxy, alkylsulphonylamino, triazol and tetrazolyl.

26. A compound according to claim 24, in which -Lp(D)n is selected from the following formulae:

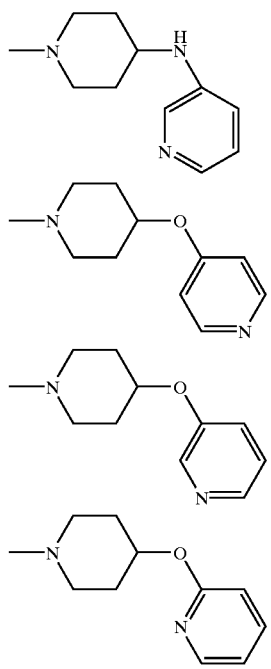

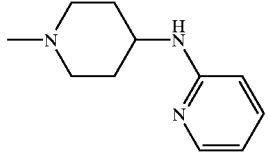

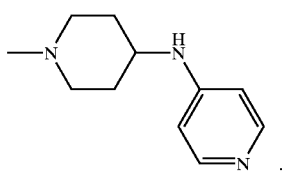

27. A pharmaceutical composition, which comprises a compound as claimed in claim 1 together with at least one pharmaceutically acceptable carrier or excipient.

28. A method of treatment of the human or non-human animal body to combat a thrombotic disorder, said method comprising administering to said body an effective amount of a compound according to claim 1.

* * * * *